US006423716B1

(12) United States Patent
Matsuno et al.

(10) Patent No.: US 6,423,716 B1
(45) Date of Patent: *Jul. 23, 2002

(54) NITROGENOUS HETEROCYCLIC COMPOUNDS

(75) Inventors: Kenji Matsuno; Yuji Nomoto, both of Shizuoka; Michio Ichimura, Mishima; Shin-ichi Ide, Numadzu; Shoji Oda, Yokohama, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/647,490
(22) PCT Filed: Mar. 31, 1999
(86) PCT No.: PCT/JP99/01665
§ 371 (c)(1),
(2), (4) Date: Sep. 29, 2000
(87) PCT Pub. No.: WO99/51582
PCT Pub. Date: Oct. 14, 1999

(30) Foreign Application Priority Data

Mar. 31, 1998 (JP) .............................. 10-87514

(51) Int. Cl.[7] ...................... A61K 31/50; A61K 31/497; C07D 257/12; C07D 253/00; C07D 401/00
(52) U.S. Cl. ............ 514/252.02; 514/242; 514/252.13; 514/252.16; 514/252.17; 544/179; 544/182; 544/234; 544/235; 544/250; 544/254; 544/257; 544/264; 544/284; 544/344; 544/349; 544/353; 544/359
(58) Field of Search ............................ 514/242, 252.02, 514/252.13, 252.16, 252.17; 544/182, 179, 234, 235, 250, 254, 257, 264, 284, 344, 349, 353, 359

(56) References Cited

U.S. PATENT DOCUMENTS

| 3,843,638 A | * 10/1974 | Nicki et al. ................. 260/243 |
| 5,409,930 A | 4/1995 | Spada et al. ................. 514/248 |
| 5,521,184 A | 5/1996 | Zimmermann ............... 514/252 |
| 5,656,643 A | 8/1997 | Spada et al. ................. 514/312 |
| 5,679,683 A | 10/1997 | Bridges et al. ............. 514/267 |
| 5,686,457 A | 11/1997 | Traxler et al. ............. 514/258 |
| 5,981,533 A | 11/1999 | Traxler et al. ............. 514/258 |
| 6,096,749 A | 8/2000 | Traxler et al. ............. 514/258 |

FOREIGN PATENT DOCUMENTS

| EP | 520 722 | 12/1992 |
| EP | 860 433 | 8/1998 |
| GB | 1277566 | 6/1972 |
| JP | 46-10543 | 3/1971 |
| JP | 6-247942 | 9/2000 |
| WO | WO 92/20642 | 11/1992 |
| WO | WO 96/09294 | 3/1996 |
| WO | WO 96/40142 | 12/1996 |
| WO | WO 97/02266 | 1/1997 |
| WO | WO 97/13771 | 4/1997 |
| WO | WO 97/27199 | 7/1997 |
| WO | WO 98/14431 | 4/1998 |
| ZA | 67-6512 | 10/1967 |

OTHER PUBLICATIONS

Agrawal, V.K. and Sharma, S., "Antiparasitic Agents: Part VI", Indian J. of Chemistry, (1987) vol. 26B, pp. 550–555.
Khimiko–Farmatsveticheskij Zhurnal (1982), pp. 1338–1343 (Chemical Abstracts, vol. 98 No. LO7247 (1983)).
Pharmacology Biochemistry and Behavior, vol. 53, No. 1 (1996), pp. 87–97.
Eur J. Med. Chem, vol. 31 (1996), pp. 417–425.
Indian Journal of Chemistry, vol. 26B (1987), pp. 550–595.
Cancer Research, vol. 54 (1994), pp. 6106–6114.
J. Med. Chem., vol. 40 (1997), pp. 2296–2303.
J. Med. Chem., vol. 40 (1997), pp. 413–426.
J. Med. Chem., vol. 39 (1996), pp. 1823–1835.
J. Med. Chem., vol. 40 (1997), pp. 1820–1826.
J. Med. Chem., vol. 40 (1997), pp. 1519–1529.

* cited by examiner

Primary Examiner—Mukund J. Shah
Assistant Examiner—Tamthom N. Truong
(74) Attorney, Agent, or Firm—Fitzpatrick, Cella, Harper & Scinto

(57) ABSTRACT

The present invention relates to nitrogen-containing heterocyclic compounds represented by formula (I):

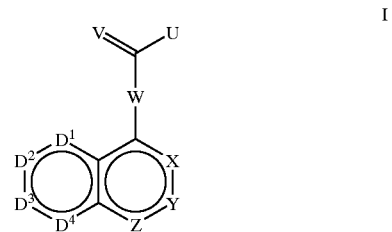

wherein W represents 1,4-piperazinediyl, etc.; U represents $NR^1R^2$ (wherein $R^1$ represents a hydrogen atom, a substituted or unsubstituted alkyl group, etc.; and $R^2$ represents a hydrogen atom, etc. ), $OR^4$, or $SR^5$; V represents an oxygen atom, a sulfur atom, $N-R^6$, or $CR^7R^8$, at least one of X, Y and Z represents a nitrogen atom, and the others are the same or different, and each represents a nitrogen atom or $C-R^A$; and $D^1$, $D^2$, $D^3$ and $D^4$ each independently represent $C-R^B$, a nitrogen atom, an oxygen atom, a sulfur atom, etc., optional adjoining two among $D^1$ to $D^4$ are combined to represent a nitrogen atom, $N-R^{2A}$, an oxygen atom, a sulfur atom, etc., or optional adjoining two selected from $D^1$ to $D^4$ represent $C-R^{B"}$ (wherein two $R^{B"}$s are combined to represent substituted or unsubstituted alicyclic alkene, substituted or unsubstituted pyrrole, substituted or unsubstituted pyrazole, etc.; or pharmaceutically acceptable salts thereof.

24 Claims, No Drawings

NITROGENOUS HETEROCYCLIC COMPOUNDS

TECHNICAL FIELD

The present invention relates to nitrogen-containing heterocyclic compounds or pharmaceutically acceptable salts thereof which have an activity of inhibiting phosphorylation of a platelet-derived growth factor (PDGF) receptor and are useful in treating cell proliferative diseases, such as arteriosclerosis, vascular re-obstruction disease, cancers, glomerulonephritis, and the like.

BACKGROUND ART

It is known that PDGF functions as an advancing factor upon cell proliferative diseases, such as arteriosclerosis, vascular re-obstruction after percutaneous transluminal coronary angioplasty or bypass angioplasty, cancers, glomerulonephritis, glomerulosclerosis, psoriasis, articular rheumatism, and the like [*Cell*, 46: 155–169 (1986), *Science*, 253: 1129–1132 (1991), *Nihon Rinsho*, 50: 3038–3045 (1992), *Nephrol Dial Transplant*, 10: 787–795 (1995), *Kidney International*, 43 (Suppl. 39): 86–89 (1993), *Journal of Rheumatology*, 21: 1507–1511 (1994), *Scandinavian Journal of Immunology*, 27: 285–294 (1988), etc.].

Regarding nitrogen-containing heterocyclic compounds useful as medicaments, for example, N,N-dimethyl-4-(6,7-dimethoxy- 4-quinazolinyl)-1-piperazine carboxamide is disclosed as a bronchodilator in South African Patent 67 06512 (1968). Also, pyrrolo[3,2-d]pyrimidine derivatives are disclosed in *Khimiko-Farmatsveticheskij Zhurnal*, 16: 1338–1343 (1982) as antibacterial agents, quinoline derivatives having benzodiazepine receptor agonistic activity are disclosed in *Pharmacology Biochemistry and Behavior*, 53: 87–97 (1996) and *European Journal of Medicinal Chemistry*, 31: 417–425 (1996), and quinoline derivatives useful as anti-parasitic agents are disclosed in *Indian Journal of Chemistry*, 26B: 550–555 (1987).

Also, regarding PDGF receptor phosphorylation inhibitors, bismono- and bicyclic aryl and heteroaryl compounds are disclosed in WO 92/20642, and quinoxaline derivatives in *Cancer Research*, 54: 6106 (1994), pyrimidine derivatives in Japanese Published Unexamined Patent Application No. 87834/94, quinoline derivatives and quinazoline derivatives in WO 97/17329, pyrido[2,3-d]pyrimidine derivatives in *J. Med. Chem.*, 40: 2296 (1997), etc. and selenium derivatives in *J. Med. Chem.*, 40: 413 (1997).

Inhibitors of phosphorylation of epidermal growth factor (EGF) receptor family are disclosed, for example, in Japanese Published Unexamined Patent Application No. 208911/93, WO 96/09294, WO 96/31510 and WO 97/13771. Tricyclic system nitrogen-containing heterocyclic compounds disclosed in WO 95/19970 and pyridopyrimidine derivatives disclosed in *J. Med. Chem.*, 39: 1823 (1996), for example, are known as compounds having the activity inhibiting phosphorylation of a receptor of EGF which is a tyrosine kinase. Also, as inhibitors of phosphorylation of an EGF receptor or EGF receptor family, pyrimidopyrimidine derivatives are disclosed in *J. Med. Chem.*, 40: 1820 (1997), pyrrolo- and pyrazoloquinazoline derivatives are disclosed in *J. Med. Chem.*, 40: 1519 (1997), and pyrrolopyrimidine derivatives are disclosed in WO 96/40142, WO 97/02266, WO 97/27199, EP 682027, etc. In addition, inhibitors of phosphorylation of EGF receptor family are disclosed in Japanese Published Unexamined Patent Application No. 208911/93, WO 96/09294, WO 96/31510, WO 97/13771, etc. All of these compounds are ring-fused pyrimidine derivatives and have a structure in which a simple amino group such as a substituted anilino group, an alkoxy group or the like are linked to the 4-position of the pyrimidine ring.

On the other hand, in the compounds disclosed in the present invention, a structure, such as urea, thiourea, guanidine, amidine, or the like, is linked to a position corresponding to the 4-position of pyrimidine, via substituted or unsubstituted piperazine or homopiperazine, and such a structure is not known as to substances having the activity of inhibiting phosphorylation of EGF receptors and the like.

DISCLOSURE OF THE INVENTION

The present invention relates to a nitrogen-containing heterocyclic compound represented by formula (I):

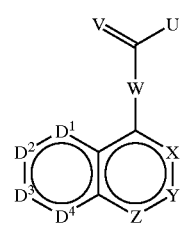

wherein W represents 1,4-piperazinediyl or 1,4-homopiperazinediyl in which carbon atoms on the ring may be substituted with 1 to 4 alkyl groups which are the same or different;

U represents $NR^1R^2$ (wherein $R^1$ represents a hydrogen atom, a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group; and $R^2$ represents a hydrogen atom, a substituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, a substituted or unsubstituted heteroarylalkyl group, $CQR^{1A}$ (wherein Q represents an oxygen atom or a sulfur atom; and $R^{1A}$ has the same meaning as $R^1$ described above), or $SO_2R^3$ (wherein $R^3$ represents a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group)), $OR^4$ (wherein $R^4$ has the same meaning as $R^3$ described above), or $SR^5$ (wherein $R^5$ has the same meaning as $R^3$ described above);

V represents an oxygen atom, a sulfur atom, N—$R^6$ (wherein $R^6$ has the same meaning as $R^1$ described above or represents a cyano group, a hydroxyl group, a nitro group, a carbamoyl group, $COOR^{3A}$ (wherein $R^{3A}$ has the same meaning as $R^3$ described above), $CQ^A R^{1B}$ (wherein $Q^A$ has the same meaning as Q described above, and $R^{1B}$ has the same meaning as $R^1$ described above), or $SO_2 R^{3B}$ (wherein $R^{3B}$ has the same meaning as $R^3$ described above)), or $CR^7 R^8$ (wherein $R^7$ and $R^8$ are the same or different and each represents a hydrogen atom, a cyano group, a nitro group, $COOR^{3C}$ (wherein $R^{3C}$ has the same meaning as $R^3$ described above), or $SO_2 R^{3D}$ (wherein $R^{3D}$ has the same meaning as $R^3$ described above)), with the proviso that, when $R^1$ is hydrogen, $R^6$ and $R^2$ may be exchanged, V may represent $N-R^2$ (wherein $R^2$ has the same meaning as defined above), and $R^2$ may represent $R^6$ (wherein $R^6$ has the same meaning as defined above), and when U is $OR^4$ or $SR^5$, V represents $N-R^6$ or $CR^7 R^8$, at least one of X, Y and Z represents a nitrogen atom, and the others are the same or different, and each represents a nitrogen atom or $C-R^A$ <wherein $R^A$ has the same meaning as $R^1$ defined above, or represents a halogen atom, a cyano group, a nitro group, $NR^9 R^{10}$ {wherein $R^9$ and $R^{10}$ are the same or different, and each has the same meaning as $R^1$ described above, or represents $SO_2 R^{3E}$ (wherein $R^{3E}$ has the same meaning as $R^3$ described above) or $CQ^B R^{11}$ (wherein $Q^b$ has the same meaning as Q described above; and $R^{11}$ has the same meaning as $R^1$ described above, or represents $OR^{3F}$ (wherein $R^{3F}$ has the same meaning as $R^3$ described above) or $NR^{1C} R^{1D}$ (wherein $R^{1C}$ and $R^{1D}$ are the same or different, and each has the same meaning as $R^1$ described above, or $R^{1C}$ and $R^{1D}$ are combined to represent a substituted or unsubstituted nitrogen-containing heterocyclic group)), or $R^9$ and $R^{10}$ are combined to represent a substituted or unsubstituted nitrogen-containing heterocyclic group}, $CQ^C R^{11A}$ (wherein $Q^C$ has the same meaning as Q described above; and $R^{11A}$ has the same meaning as $R^{11}$ described above), $OR^{12}$ {wherein $R^{12}$ has the same meaning as $R^1$ described above, or represents $CQ^D R^{13}$ (wherein $Q^D$ has the same meaning as Q described above; and $R^{13}$ has the same meaning as $R^1$ described above, or represents $OR^{3G}$ (wherein $R^{3G}$ has the same meaning as $R^3$ described above), $SR^{3H}$ (wherein $R^{3H}$ has the same meaning as $R^3$ described above), or $NR^{1E} R^{1F}$ (wherein $R^{1E}$ and $R^{1F}$ are the same or different, and each has the same meaning as $R^1$ described above, or $R^{1E}$ and $R^{1F}$ are combined to represent a substituted or unsubstituted nitrogen-containing heterocyclic group)), or $SO_2 R^{3I}$ (wherein $R^{3I}$ has the same meaning as $R^3$ described above)}, $SR^{1G}$ (wherein $R^{1G}$ has the same meaning as $R^1$ described above), $SOR^{3J}$ (wherein $R^{3J}$ has the same meaning as $R^3$ described above) or $SO_2 R^{14}$ (wherein $R^{14}$ has the same meaning as $R^3$ described above, or represents $OR^{1H}$ (wherein $R^{1H}$ has the same meaning as $R^1$ described above) or $NR^{1I} R^{1J}$ (wherein $R^{1I}$ and $R^{1J}$ are the same or different, and each has the same meaning as $R^1$ described above, or $R^{1I}$ and $R^{1J}$ are combined to represent a substituted or unsubstituted nitrogen-containing heterocyclic group))>, and (1) when V represents $N-R^6$ or $CR^7 R^8$, and U represents $NR^1 R^2$, $OR^4$, or $SR^5$, $D^1$, $D^2$, $D^3$ and $D^4$ each independently represent $C-R^B$ (wherein $R^B$ has the same meaning as $R^A$ described above), a nitrogen atom, an oxygen atom, or a sulfur atom; or optional adjoining two among $D^1$ to $D^4$ may be combined to represent a nitrogen atom, $N-R^{2A}$ (wherein $R^{2A}$ has the same meaning as $R^2$ described above, or represents an alkyl group or $CQ^E NHR^{3K}$ (wherein $Q^E$ has the same meaning as Q described above; and $R^{3K}$ has the same meaning as $R^3$ described above)), an oxygen atom, or a sulfur atom, and the remains among $D^1$ to $D^4$ may represent $C-R^{B'}$ (wherein $R^{B'}$ has the same meaning as $R^A$ described above), $N-R^{2A'}$ (wherein $R^{2A'}$ has the same meaning as $R^{2A}$ described above), or a nitrogen atom; and in these two cases, the optional adjoining two selected from $D^1$ to $D^4$ may represent $C-R^{B''}$ (wherein two $R^{B''}$s, together with the two adjoining carbon atoms, represent substituted or unsubstituted alicyclic alkene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted thiophene, substituted or unsubstituted oxazole, substituted or unsubstituted oxadiazole, substituted or unsubstituted isoxazole, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), and (2) when V represents an oxygen atom or a sulfur atom, and U represents $NR^1 R^2$, (2-1)

at least one of $D^1$ to $D^4$ represents a nitrogen atom, an oxygen atom or a sulfur atom; optional adjoining two among $D^1$ to $D^4$ are combined to represent a nitrogen atom, $N-R^{2B}$ (wherein $R^{2B}$ has the same meaning as $R^2$ described above), or an oxygen atom; or $D^2$ and $D^3$ are combined to represent a sulfur atom; and in these three cases, the remains among $D^1$ to $D^4$ represent a nitrogen atom, $N-R^{2B'}$ (wherein $R^{2B'}$ has the same meaning as $R^2$ described above), an oxygen atom, a sulfur atom, or $C-R^C$ (wherein the $R^C$s each independently have the same meaning as $R^A$ described above, or optional two $R^C$s' adjoining carbon atoms of which are adjacent, together with the two adjoining carbon atoms, may represent substituted or unsubstituted alicyclic alkene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted oxazole, substituted or unsubstituted oxadiazole, substituted or unsubstituted isoxazole, substituted or unsubstituted thiophene, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), (2-2)

$D^1$ and $D^2$ are combined to represent a sulfur atom; $D^3$ represents $C-R^{C'}$ (wherein $R^{C'}$ has the same meaning as $R^A$ described above); and $D^4$ represents a nitrogen atom, or $D^3$ and $D^4$ represent C—$R^{C'''}$ (wherein $R^{C'''}$s, together with two adjoining carbon atoms, represent substituted or unsubstituted alicyclic alkene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted oxazole, substituted or unsubstituted oxadiazole, substituted or unsubstituted isoxazole, substituted or unsubstituted thiophene, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), (2-3)

$D^3$ and $D^4$ are combined to represent a sulfur atom; $D^2$ represents C—$R^{C'''}$ (wherein $R^{C'''}$ has the same meaning as $R^A$ described above); and $D^1$ represents a nitrogen atom, or $D^1$ and $D^2$ represent C—$R^{C'''}$ (wherein $R^{C'''}$ has the same meaning as $R^{C'''}$ described above), or (2-4)

$D^1$, $D^2$, $D^3$ and $D^4$ represent C—$R^D$ (wherein in $R^D$s, optional two $R^D$s' adjoining carbon atoms of which are adjacent, together with the two adjoining carbon atoms, represent substituted or unsubstituted alicyclic alkene, substituted or unsubstituted pyrrole, substituted or unsubstituted pyrazole, substituted or unsubstituted furan, substituted or unsubstituted thiophene, substituted or unsubstituted oxadiazole, substituted or unsubstituted isoxazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, or substituted or unsubstituted tetrazine, and each of the remaining $R^D$S independently represents the same meaning as $R^A$ described above), or a pharmaceutically acceptable salt thereof.

Hereinafter, the compound represented by formula (I) is called compound (I). Compounds represented by other formula numbers are also called in the same manner.

In the definition of each group of formula (I), examples of the alkyl group include straight or branched alkyl groups having from 1 to 16 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, hexadecyl, and the like; examples of the alicyclic alkyl group include monocyclic groups having from 3 to 12 carbon atoms, such as cyclopropyl, cyclobutyl, cyclopentyl, cyclohexyl, cycloheptyl, cyclooctyl and cyclododecyl and polycyclic groups including pinanyl, 1,7,7-trimethylbicyclo[2.2.1]heptyl, adamantyl, hexahydro-4,7-methano-1H-indenyl, 4-hexylbicyclo[2.2.2]octyl, and the like; examples of the alicyclic heterocyclic group include tetrahydrofuryl, tetrahydropyranyl, pyrrolidinyl, piperidyl, piperazinyl, morpholinyl, thiomorpholinyl, and the like; examples of the nitrogen-containing heterocyclic group include pyrrolidinyl, piperidino, piperidinyl, homopiperidino, homopiperidinyl, piperazinyl, homopiperazinyl, morpholino, morpholinyl, thiomorpholino, thiomorpholinyl, pyrrolyl, imidazolyl, pyrazolyl, triazolyl, tetrazolyl, indolyl, indazolyl, benzimidazolyl, benzotriazolyl, and the like; examples of the alkenyl group include straight or branched alkenyl groups having from 2 to 16 carbon atoms, such as vinyl, allyl, 1-propenyl, isopropenyl, methacryl, butenyl, crotyl, pentenyl, hexenyl, heptenyl, decenyl, dodecenyl, hexadecenyl, and the like; examples of the alkynyl group include straight or branched alkynyl groups having from 2 to 16 carbon atoms, such as ethynyl, propargyl, butynyl, pentynyl, hexynyl, heptynyl, decynyl, dodecynyl, hexadecynyl, and the like; examples of the aryl group include phenyl, naphthyl, anthryl, pyrenyl, and the like; examples of the aralkyl group include those having from 7 to 15 carbon atoms, such as benzyl, phenethyl, phenylpropyl, phenylbutyl, benzhydryl, trityl, naphthylmethyl, naphthylethyl, and the like; and examples of the heteroaryl group include pyridyl, pyrimidinyl, pyrazinyl, pyridazinyl, triazinyl, quinolyl, isoquinolyl, quinazolinyl, phthalazinyl, quinoxalinyl, naphthyridinyl, cinnolinyl, thienyl, furyl, pyrrolyl, imidazolyl, pyrazolyl, triazolyl, tetrazolyl, oxazolyl, thiazolyl, thiadiazolyl, benzothienyl, benzofuryl, indolyl, indazolyl, benzimidazolyl, benzotriazolyl, benzoxazolyl, benzothiazolyl, purinyl, and the like. The heteroaryl moiety of the heteroarylalkyl group has the same meaning as the heteroaryl group described above, and its alkyl moiety has the same meaning as the alkyl group described above. Examples of the alicyclic alkene include those having from 4 to 12 carbon atoms, such as cyclobutene, cyclopentene, cyclohexene, cycloheptene, cyclooctene, cyclododecene, and the like. The halogen atom means any atom of fluorine, chlorine, bromine and iodine.

The substituents of the substituted alkyl group, substituted alkenyl group, substituted alkynyl group, substituted alicyclic alkyl group, substituted alicyclic heterocyclic group and substituted alicyclic alkene are the same or different and includes 1 to 3 substituents, such as a nitro group, a cyano group, a hydroxyl group, an oxo group, a halogen atom, an alicyclic alkyl group, an aryl group, an alicyclic heterocyclic group, a carboxyl group, a formyl group, $G^1$—$J^1$—$R^{15}$ {wherein $G^1$ represents a single bond, an oxygen atom, or a sulfur atom; $J^1$ represents CO, CS, or $SO_2$; and $R^{15}$ represents an alkyl group, an alicyclic alkyl group, an alicyclic heterocyclic group, an alkenyl group, an alkynyl group, an $R^{16}$-substituted aryl group (wherein $R^{16}$ represents an alkyl group, a nitro group, a cyano group, a hydroxyl group, a halogen atom, or $NR^{17}R^{18}$ (wherein $R^{17}$ and $R^{18}$ are the same or different, and each represents a hydrogen atom, an alkyl group, an alicyclic alkyl group, an alicyclic heterocyclic group, an alkenyl group, an alkynyl group, an aryl group, an aralkyl group, a heteroaryl group, or a heteroarylalkyl group, or $R^{17}$ and $R^{18}$ are combined to represent a nitrogen-containing heterocyclic group)) or an unsubstituted aryl group, an aralkyl group, a heteroaryl group, a heteroarylalkyl group, an alkoxy group, a trifluoromethyl group, a trifluoromethoxy group, an alicyclic alkoxy group, an O-alicyclic hetero ring-substituted hydroxyl group, an alkenyloxy group, an alkynyloxy group, an $R^{16}$-substituted aryloxy group (wherein $R^{16}$ has the same meaning as defined above) or an unsubstituted aryloxy group, an aralkyloxy group, a heteroaryloxy group, a heteroarylalkoxy group, an amino group, an alkylamino group, an alicyclic alkylamino group, an $R^{19}$-substituted N-alicyclic hetero ring-substituted amino group (wherein $R^{19}$ represents a hydroxyl group, an oxo group, or $NR^{20}R^{21}$ (wherein $R^{20}$ and $R^{21}$ are the same or different, and each represents a hydrogen atom, an alkyl group, an alicyclic alkyl group, an alicyclic heterocyclic group, an alkenyl group, an alkynyl group, an aryl group, an aralkyl group, a heteroaryl group, or a heteroarylalkyl group, or $R^{20}$ and $R^{21}$ are combined to represent a nitrogen-containing heterocyclic group)) or an unsubstituted N-alicyclic hetero ring-substituted amino group, an alkenylamino group, an alkynylamino group, an $R^{16}$-substituted arylamino group (wherein $R^{16}$ has the same meaning as defined above) or an unsubstituted arylamino group, an aralkylamino group, a heteroarylamino group, or a heteroarylalkylamino group}, $NR^{22}R^{23}$ (wherein $R^{22}$ and $R^{23}$ are the same or different, and each represents a hydrogen atom, an alkyl group, an alicyclic alkyl group, an alicyclic heterocyclic group, an alkenyl group, an alkynyl group, an $R^{16}$-substituted aryl group (wherein $R^{16}$ has the same meaning as defined above) or an unsubstituted aryl group, an aralkyl group, a heteroaryl group, a heteroarylalkyl group, an alkanoyl group, an alicyclic alkanoyl group, an alicyclic heteroring-carbonyl group, an alkenoyl group, an alkynoyl group, an $R^{16}$-substituted aroyl group (wherein $R^{16}$ has the same meaning as defined above) or an unsubstituted aroyl group, an aralkylcarbonyl group, a heteroarylcarbonyl group, a heteroarylalkylcarbonyl group, an alkoxycarbonyl group, an alicyclic alkoxycarbonyl group, an O-alicyclic hetero ring-substituted hydroxycarbonyl group, an alkenyloxycarbonyl group, an alkynyloxycarbonyl group, an $R^{16}$-substituted aryloxycarbonyl group (wherein $R^{16}$ has the same meaning as defined above) or an unsubstituted aryloxycarbonyl group, an aralkyloxycarbonyl group, a heteroaryloxycarbonyl group, a heteroarylalkoxycarbonyl group, an alkylsulfonyl group, an alicyclic alkylsulfonyl group, an alicyclic heteroring-sulfonyl group, an alkenylsulfonyl group, an alkynylsulfonyl group, an $R^{16}$-substituted arylsulfonyl group (wherein $R^{16}$ has the same meaning as defined above) or an unsubstituted arylsulfonyl group, an aralkylsulfonyl group, a heteroarylsulfonyl group, a heteroarylalkylsulfonyl group, or $-CQ^F NR^{17A}R^{18A}$ (wherein $Q^F$ represents an oxygen atom or a sulfur atom; and $R^{17A}$ and $R^{18A}$ have the same meanings as $R^{17}$ and $R^{18}$ defined above), or $R^{22}$ and $R^{23}$ are comb nitrogen-containing heterocyclic group), an alkoxy group, an alicyclic alkoxy group, an O-alicyclic hetero ring-substituted hydroxyl group, an alkenyloxy group, an alkynyloxy group, an $R^{16}$-substituted aryloxy group (wherein $R^{16}$ has the same meaning as defined above) or an unsubstituted aryloxy group, an aralkyloxy group, a heteroaryloxy group, a heteroarylalkoxy group, a sulfo group, a trifluoromethylthio group, an alkylthio group, an alicyclic alkylthio group, an alicyclic heteroring-thio group, an alkenylthio group, an alkynylthio group, an $R^{16}$-substituted arylthio group (wherein $R^{16}$ has the same meaning as defined above) or an unsubstituted arylthio group, an aralkylthio group, a heteroarylthio group, a heteroarylalkylthio group, a trifluoromethylsulfinyl group, an alkylsulfinyl group, an alicyclic alkylsulfinyl group, an alicyclic heteroring-sulfinyl group, an alkenylsulfinyl group, an alkynylsulfinyl group, an $R^{16}$-substituted arylsulfinyl group (wherein $R^{16}$ has the same meaning as defined above) or an unsubstituted arylsulfinyl group, an aralkylsulfinyl group, a heteroarylsulfinyl group, a heteroarylalkylsulfinyl group, and the like.

The substituents of the substituted nitrogen-containing heterocyclic group, substituted aryl group, substituted aralkyl group, substituted heteroaryl group, substituted heteroarylalkyl group, substituted pyrrole, substituted pyrazole, substituted imidazole, substituted imidazol-2-one, substituted imidazole-2-thione, substituted triazole, substituted furan, substituted 1,3-dioxole, substituted 1,4-dioxene, substituted thiophene, substituted oxazole, substituted oxadiazole, substituted isoxazole, substituted thiazole, substituted isothiazole, substituted thiadiazole, substituted pyridine, substituted pyrazine, substituted pyrimidine, substituted pyridazine, substituted triazine, substituted tetrazine and substituted phenyl are the same or different, and includes 1 to 3 substituents, such as a nitro group, a cyano group, a hydroxyl group, a halogen atom, a methylenedioxy group, $(OCH_2CH_2)_nO$ (wherein n is an integer of 1 to 6), a trimethylene group, a trifluoromethyl group, a difluoromethoxy group, a trifluoromethoxy group, an azido group, a thiocyanato group, an $R^{19}$-substituted alkyl group (wherein $R^{19}$ has the same meaning as defined above) or an unsubstituted alkyl group, an $R^{16}$-substituted alicyclic alkyl group (wherein $R^{16}$ has the same meaning as defined above) or an unsubstituted alicyclic alkyl group, an alicyclic heterocyclic group, an alkenyl group, an alkynyl group, an aryl group, an aralkyl group, a heteroaryl group, a heteroarylalkyl group, a carboxyl group, a formyl group, $G^1-J^1-R^{15}$ (wherein $G^1$, $J^1$ and $R^{15}$ have the same meanings as defined above), $NR^{22}R^{23}$ (wherein $R^{22}$ and $R^{23}$ have the same meanings as defined above), an alkoxy group, an alicyclic alkoxy group, an O-alicyclic hetero ring-substituted hydroxyl group, an alkenyloxy group, an alkynyloxy group, an $R^{16}$-substituted aryloxy group (wherein $R^{16}$ has the same meaning as defined above) or an unsubstituted aryloxy group, an aralkyloxy group, a heteroaryloxy group, a heteroarylalkoxy group, a sulfo group, a trifluoromethylthio group, an alkylthio group, an alicyclic alkylthio group, an alicyclic-heteroring-thio group, an alkenylthio group, an alkynylthio group, an $R^{16}$-substituted arylthio group (wherein $R^{16}$ has the same meaning as defined above) or an unsubstituted arylthio group, an aralkylthio group, a heteroarylthio group, a heteroarylalkylthio group, a trifluoromethylsulfinyl group, an alkylsulfinyl group, an alicyclic alkylsulfinyl group, an alicyclic heteroring-sulfinyl group, an alkenylsulfinyl group, an alkynylsulfinyl group, an $R^{16}$-substituted arylsulfinyl group (wherein $R^{16}$ has the same meaning as defined above) or an unsubstituted arylsulfinyl group, an aralkylsulfinyl group, a heteroarylsulfinyl group, a heteroarylalkylsulfinyl group, an $R^{16}$-substituted arylazo group (wherein $R^{16}$ has the same meaning as defined above) or an unsubstituted arylazo group, a heteroarylazo group, and the like.

In the above definition of each substituent, the alkyl moiety of the alkoxy group, alkylamino group, alkanoyl group, alkoxycarbonyl group, alkylthio group and alkylsulfinyl group has the same meaning as the alkyl group described above; the alicyclic alkyl moiety of the alicyclic alkoxy group, alicyclic alkylamino group, alicyclic alkanoyl group, alicyclic alkoxycarbonyl group, alicyclic alkylsulfonyl group, alicyclic alkylthio group and alicyclic alkylsulfinyl group has the same meaning as the alicyclic alkyl group described above; the alicyclic hetero ring moiety of the O-alicyclic hetero ring-substituted hydroxyl group, N-alicyclic hetero ring-substituted amino group, alicyclic heteroring-carbonyl group, O-alicyclic hetero ring-substituted hydroxycarbonyl group, alicyclic heteroring-sulfonyl group, alicyclic heteroring-thio group and alicyclic heteroring-sulfinyl group has the same meaning as the alicyclic heterocyclic group described above; the alkenyl moiety of the alkenyloxy group, alkenylamino group, alkenoyl group, alkenyloxycarbonyl group, alkenylsulfonyl group, alkenylthio group and alkenylsulfinyl group has the same meaning as the alkenyl group described above; the alkynyl moiety of the alkynyloxy group, alkynylamino group, alkynoyl group, alkynylsulfonyl group, alkynylthio group and alkynylsulfinyl group has the same meaning as the, alkynyl group described above; the aryl moiety of the aryloxy group, arylamino group, aroyl group, aryloxycarbonyl group, arylsulfonyl group, arylthio group, arylsulfinyl group and arylazo group has the same meaning as the aryl group described above; the aralkyl moiety of the aralkyloxy group, aralkylamino group, aralkylcarbonyl group, aralkyloxycarbonyl group, aralkylsulfonyl group, aralkylthio group and aralkylsulfinyl group has the same meaning as the aralkyl group described above; the heteroaryl moiety of the heteroaryloxy group, heteroarylamino group, heteroarylcarbonyl group, heteroaryloxycarbonyl group, heteroarylsulfonyl group, heteroarylthio group, heteroarylsulfinyl group and heteroarylazo group has the same meaning as the heteroaryl group described above; and the heteroarylalkyl moiety of heteroarylalkoxy group, heteroarylalkylamino group, heteroarylalkylcarbonyl group, heteroarylalkoxycarbonyl group, heteroarylalkylsulfonyl group, heteroarylalkylthio group and heteroarylalkylsulfinyl group has the same meaning as the heteroarylalkyl group described above. Also, the alicyclic alkyl group, aryl group, alicyclic heterocyclic group, alkyl group, alkenyl group, alkynyl group, halogen atom, aralkyl group, heteroaryl group, heteroarylalkyl group and nitrogen-containing heterocyclic group have the same meanings as described above, respectively.

As preferred embodiments of the present invention, nitrogen-containing heterocyclic compounds wherein W represents 1,4-piperazinediyl or pharmaceutically acceptable salts thereof can be exemplified. Particularly, compounds wherein at least one of X and Z represents a nitrogen atom, and Y represents C—$R^A$ (wherein $R^A$ has the same meaning as defined above) are preferred, and compounds wherein X and Z represent nitrogen atoms, and $R^A$ represents a hydrogen atom or $NR^9R^{10}$ (wherein $R^9$ and $R^{10}$ have the same meanings as defined above) are preferred. Further, nitrogen-containing heterocyclic compounds wherein U is $NR^1R^2$ (wherein $R^1$ and $R^2$ have the same meanings as defined above) or pharmaceutically acceptable salts thereof are preferred.

Among these nitrogen-containing heterocyclic compounds or pharmaceutically acceptable salts thereof, in preferred compounds, $R^1$ represents a hydrogen atom; and $R^2$ represents a hydrogen atom, a substituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group, and more preferably, $R^2$ represents a substituted or unsubstituted aryl group, a substituted or unsubstituted aralkyl group, a substituted or unsubstituted heteroaryl group, or a substituted or unsubstituted heteroarylalkyl group.

In addition, the following nitrogen-containing heterocyclic compounds or pharmaceutically acceptable salts thereof are excellent among the above preferred embodiments.

Preferred examples include nitrogen-containing heterocyclic compounds or pharmaceutically acceptable salts thereof, wherein V represents N—$R^6$ (wherein $R^6$ has the same meaning as defined above); and 1) $D^1$ and $D^2$ are combined to represent N—$R^{2A}$ (wherein $R^{2A}$ has the same meaning as defined above); and $D^3$ and $D^4$ each independently represents C—$R^{B'}$ (wherein $R^{B'}$ has the same meaning as defined above), 2) $D^1$ and $D^2$ each independently represents C—$R^{B'}$ (wherein $R^{B'}$ has the same meaning as defined above); and $D^3$ and $D^4$ are combined to represent N—$R^{2A}$ (wherein $R^{2A}$ has the same meaning as defined above), 3) $D^1$ and $D^4$ each independently represents C—$R^{B'}$ (wherein $R^{B'}$ has the same meaning as defined above); and $D^2$ and $D^3$ are combined to represent N—$R^{2A}$ (wherein $R^{2A}$ has the same meaning as defined above), 4) $D^1$ represents C—$R^{B'}$ (wherein $R^{B'}$ has the same meaning as defined above); $D^2$ and $D^3$ are combined to represent a nitrogen atom; and $D^4$ represents N—$R^{2A'}$ (wherein $R^{2A'}$ has the same meaning as defined above), 5) $D^4$ represents C—$R^{B'}$ (wherein $R^{B'}$ has the same meaning as defined above); $D^2$ and $D^3$ are combined to represent a nitrogen atom; and $D^1$ represents N—$R^{2A'}$ (wherein $R^{2A'}$ has the same meaning as defined above), 6) $D^1$ and $D^2$ are combined to represent N—$R^{2A}$ (wherein $R^{2A}$ has the same meaning as defined above); $D^3$ represents C—$R^{B'}$ (wherein $R^{B'}$ has the same meaning as defined above); and $D^4$ represents a nitrogen atom, 7) $D^1$ and $D^2$ are combined to represent a nitrogen atom; $D^3$ represents C—$R^{B'}$ (wherein $R^{B'}$ has the same meaning as defined above); and $D^4$ represents N—$R^{2A'}$ (wherein $R^{2A'}$ has the same meaning as defined above), 8) $D^1$, $D^2$ and $D^3$ each independently represents C—$R^B$ (Wherein $R^B$ has the same meaning as defined above); and $D^4$ represents a nitrogen atom, 9) $D^1$, $D^2$ and $D^4$ each independently represents C—$R^B$ (wherein $R^B$ has the same meaning as defined above); and $D^3$ represents a nitrogen atom, 10) $D^1$, $D^3$ and $D^4$ each independently represents C—$R^B$ (wherein $R^B$ has the same meaning as defined above); and $D^2$ represents a nitrogen atom, 11) $D^2$, $D^3$ and $D^4$ each independently represents C—$R^B$ (wherein $R^B$ has the same meaning as defined above); and $D^1$ represents a nitrogen atom, 12) $D^1$ and $D^3$ represent nitrogen atoms; and $D^2$ and $D^4$ each independently represents C—$R^B$ (wherein $R^B$ has the same meaning as defined above), 13) $D^1$ and $D^3$ each independently represents C—$R^B$ (wherein $R^B$ has the same meaning as defined above); and $D^2$ and $D^4$ represent nitrogen atoms, 14) $D^1$ and $D^2$ each independently represents C—$R^B$ (wherein $R^B$ has the same meaning as defined above); and $D^3$ and $D^4$ represent nitrogen atoms, 15) $D^1$ and $D^4$ each independently represents C—$R^B$ (wherein $R^B$ has the same meaning as defined above); and $D^2$ and $D^3$ represent nitrogen atoms, 16) $D^3$ and $D^4$ each independently represent C—$R^B$ (wherein $R^B$ has the same meaning as defined above); and $D^1$ and $D^2$ represent nitrogen atoms, 17) $D^2$ and $D^3$ each independently represents C—$R^B$ (wherein $R^B$ has the same meaning as defined above); and $D^1$ and $D^4$ represent nitrogen atoms, 18) $D^1$, $D^2$, $D^3$ and $D^4$ each independently represents C—$R^B$ (wherein $R^B$ has the same meaning as defined above), 19) $D^1$ and $D^2$ each independently represents C—$R^{B'}$ (wherein $R^{B'}$ has the same meaning as defined above); and $D^3$ and $D^4$ are combined to represent a sulfur atom, 20) $D^1$ and $D^4$ each independently represents C—$R^{B'}$ (wherein $R^{B'}$ has the same meaning as defined above); and $D^2$ and $D^3$ are combined to represent a sulfur atom, or 21) $D^3$ and $D^4$ each independently represents C—$R^{B'}$ (wherein $R^{B'}$ has the same meaning as defined above); and $D^1$ and $D^2$ are combined to represent a sulfur atom.

Also, preferred examples include nitrogen-containing heterocyclic compounds or pharmaceutically acceptable salts thereof, wherein V represents an oxygen atom or a sulfur atom; and 1) $D^1$ and $D^2$ are combined to represent N—$R^{2B}$ (wherein $R^{2B}$ has the same meaning as defined above); and $D^3$ and $D^4$ each independently represents C—$R^C$ (wherein $R_C$ has the same meaning as defined above), 2) $D^1$ and $D^2$ each independently represents C—$R^C$ (wherein $R^C$ has the same meaning as defined above); and $D^3$ and $D^4$ are combined to represent N—$R^{2B}$ (wherein $R^{2B}$ has the same meaning as defined above), 3) $D^1$ and $D^4$ each independently represents C—$R^C$ (wherein $R^C$ has the same meaning as defined above); and $D^2$ and $D^3$ are combined to represent N—$R^{2B}$ (wherein $R^{2B}$ has the same meaning as defined above), 4) $D^1$ represents C—$R^C$ (wherein $R^C$ has the same meaning as defined above); $D^2$ and $D^3$ are combined to represent a nitrogen atom; and $D^4$ represents N—$R^{2B'}$ (wherein $R^{2B'}$ has the same meaning as defined above), 5) $D^4$ represents C—$R^C$ (wherein $R^C$ has the same meaning as defined above); $D^2$ and $D^3$ are combined to represent a nitrogen atom; and $D^1$ represents N—$R^{2B'}$ (wherein $R^{2B'}$ has the same meaning as defined above), 6) $D^1$ and $D^2$ are combined to represent N—$R^{2B}$ (wherein $R^{2B}$ has the same meaning as defined above); $D^3$ represents C—$R^C$ (wherein $R^C$ has the same meaning as defined above); and $D^4$ represents a nitrogen atom, 7) $D^1$ and $D^2$ are combined to represent a nitrogen atom; $D^3$ represents C—$R^C$ (wherein $R^C$ has the same meaning as defined above); and $D^4$ represents N—$R^{2B'}$ (wherein $R^{2B'}$ has the same meaning as defined above), 8) $D^1$, $D^2$ and $D^3$ each independently represents C—$R^C$ (wherein $R^C$ has the same meaning as defined above); and $D^4$ represents a nitrogen atom, 9) $D^1$, $D^2$ and $D^4$ each independently represents C—$R^C$ (wherein $R^C$ has the same meaning as defined above); and $D^3$ represents a nitrogen atom, 10) $D^1$, $D^3$ and $D^4$ each independently represents C—$R^C$ (wherein $R^C$ has the same meaning as defined above); and $D^2$ represents a nitrogen atom, 11) $D^2$, $D^3$ and $D^4$ each independently represents C—$R^C$ (wherein $R^C$ has the same meaning as defined above); and $D^1$ represents a nitrogen atom, 12) $D^1$ and $D^3$ represent nitrogen atoms; and $D^2$ and $D^4$ each independently represents C—$R^C$ (wherein $R^C$ has the same meaning as defined above), 13) $D^1$ and $D^3$ each independently represents C—$R^C$ (wherein $R^C$ has the same meaning as defined above); and $D^2$ and $D^4$ are nitrogen atoms, 14) $D^1$ and $D^2$ each independently represents C—$R^C$ (wherein $R^C$ has the same meaning as defined above); and $D^3$ and $D^4$ are nitrogen atoms, 15) $D^1$ and $D^4$ each independently represents C—$R^C$ (wherein $R^C$ has the same meaning as defined above); and $D^2$ and $D^3$ are nitrogen atoms, 16) $D^3$ and $D^4$ each independently represents C—$R^C$ (wherein $R^C$ has the same meaning as defined above); and $D^1$ and $D^2$ are nitrogen atoms, 17) $D^2$ and $D^3$ each independently represents C—$R^C$ (wherein $R^C$ has the same meaning as defined above); and $D^1$ and $D^4$ are nitrogen atoms, 18) $D^1$, $D^2$, $D^3$ and $D^4$ each independently represents C—$R^D$ (wherein $R^D$ has the same meaning as defined above), 19) $D^1$ and $D^2$ each independently represents C—$R^{C''''}$ (wherein $R^{C''''}$ has the same meaning as defined above); and $D^3$ and $D^4$ are combined to represent a sulfur atom, 20) $D^1$ and $D^4$ each independently represents C—$R^C$ (wherein $R^C$ has the same meaning as defined above); and $D^2$ and $D^3$ are combined to represent a sulfur atom, or 21) $D^3$ and $D^4$ each independently represents C—$R^{C''}$ (wherein $R^{C''}$ has the same meaning as defined above); and $D^1$ and $D^2$ are combined to represent a sulfur atom.

Also, preferred examples include nitrogen-containing heterocyclic compound or pharmaceutically acceptable salts thereof, wherein V represents N—CN; and 1) $D^1$ and $D^2$ are combined to represent a nitrogen atom; $D^3$ represents C—$R^{B'}$ (wherein $R^{B'}$ has the same meaning as defined above); and $D^4$ represents N—$R^{2A'}$ (wherein $R^{2A'}$ has the same meaning as defined above), 2) $D^1$, $D^2$ and $D^4$ each independently represents C—$R^B$ (wherein $R^B$ has the same meaning as defined above); and $D^3$ represents a nitrogen atom, or 3) $D^1$, $D^2$, $D^3$ and $D^4$ each independently represents C—$R^B$ (wherein $R^B$ has the same meaning as defined above).

Also, preferred examples include nitrogen-containing heterocyclic compounds or pharmaceutically acceptable salts thereof, wherein V represents N—CN; and $D^1$ and $D^2$ each independently represents C—$R^{B'}$ (wherein $R^{B'}$ has the same meaning as defined above); and $D^3$ and $D^4$ are combined to represent N—$R^{2A}$ (wherein $R^{2A}$ has the same meaning as defined above).

Also, preferred examples include nitrogen-containing heterocyclic compounds or pharmaceutically acceptable salts thereof, wherein V represents N—CN; and 1) $D^1$, $D^2$ and $D^3$ each independently represents C—$R^B$ (wherein $R^B$ has the same meaning as defined above); and $D^4$ represents a nitrogen atom, 2) $D^1$, $D^2$ and $D^4$ each independently represents C—$R^B$ (wherein $R^B$ has the same meaning as defined above); and $D^3$ represents a nitrogen atom, 3) $D^1$, $D^3$ and $D^4$ each independently represents C—$R^B$ (wherein $R^B$ has the same meaning as defined above); and $D^2$ represents a nitrogen atom, or 4) $D^2$, $D^3$ and $D^4$ each independently represents C—$R^B$ (wherein $R^B$ has the same meaning as defined above); and $D^1$ represents a nitrogen atom.

Also, preferred examples include nitrogen-containing heterocyclic compounds or pharmaceutically acceptable salts thereof, wherein V represents N—CN; and 1) $D^1$ and $D^3$ represent nitrogen atoms; and $D^2$ and $D^4$ each independently represents C—$R^B$ (wherein $R^B$ has the same meaning as defined above), or 2) $D^1$ and $D^3$ each independently represents C—$R^B$ (wherein $R^B$ has the same meaning as defined above); and $D^2$ and $D^4$ represent nitrogen atoms.

Also, preferred examples include nitrogen-containing heterocyclic compounds or pharmaceutically acceptable salts thereof, wherein V represents an oxygen atom or a sulfur atom; and 1) $D^1$ and $D^2$ are combined to represent a nitrogen atom; $D^3$ represents C—$R^C$ (wherein $R^C$ has the same meaning as defined above); and $D^4$ represents N—$R^{2B'}$ (wherein $R^{2B'}$ has the same meaning as defined above), 2) $D^1$, $D^2$ and $D^4$ each independently represents C—$R^C$ (wherein $R^C$ has the same-meaning as defined above); and $D^3$ represents a nitrogen atom, or 3) $D^1$, $D^2$, $D^3$ and $D^4$ each independently represents C—$R^D$ (wherein $R^D$ has the same meaning as defined above).

Also, preferred examples include nitrogen-containing heterocyclic compounds or pharmaceutically acceptable salts thereof, wherein V represents an oxygen atom or a sulfur atom; and $D^1$ and $D^2$ each independently represents C—$R^{B'}$ (wherein $R^{B'}$ has the same meaning as defined above); and $D^3$ and $D^4$ are combined to represent N—$R^{2A}$ (wherein $R^{2A}$ has the same meaning as defined above).

Also preferred examples include nitrogen-containing heterocyclic compounds or pharmaceutically acceptable salts thereof, wherein V represents an oxygen atom or a sulfur atom; and 1) $D^1$, $D^2$ and $D^3$ each independently represents C—$R^B$ (wherein $R^B$ has the same meaning as defined above); and $D^4$ represents a nitrogen atom, 2) $D^1$, $D^2$ and $D^4$ each independently represents C—$R^B$ (wherein $R^B$ has the same meaning as defined above); and $D^3$ represents a nitrogen atom, 3) $D^1$, $D^3$ and $D^4$ each independently represents C—$R^B$ (wherein $R^B$ has the same meaning as defined above); and $D^2$ represents a nitrogen atom, or 4) $D^2$, $D^3$ and $D^4$ each independently represents C—$R^B$ (wherein $R^B$ has the same meaning as defined above); and $D^1$ represents a nitrogen atom.

Also, preferred examples include nitrogen-containing heterocyclic compounds or pharmaceutically acceptable salts thereof, wherein V represents an oxygen atom or a sulfur atom; and 1) $D^1$ and $D^3$ represent nitrogen atoms; and $D^2$ and $D^4$ each independently represents C—$R^B$ (wherein $R^B$ has the same meaning as defined above), or 2) $D^1$ and $D^3$ each independently represents C—$R^B$ (wherein $R^B$ has the same meaning as defined above); and $D^2$ and $D^4$ represent nitrogen atoms.

Also, preferred examples include nitrogen-containing heterocyclic compounds or pharmaceutically acceptable salts thereof, wherein V represents an oxygen atom or a sulfur atom; $D^1$, $D^2$, $D^3$ and $D^4$ represent C—$R^D$ (wherein $R^D$ has the same meaning as defined above); and optional two $R^D$s' adjoining carbon atoms of which are adjacent, together with the two adjoining carbon atoms, represent substituted or unsubstituted pyrrole, substituted or unsubstituted pyrazole, substituted or unsubstituted pyridine, substituted or unsubstituted pyrimidine, substituted or unsubstituted pyridazine, or substituted or unsubstituted pyrazine.

In order to explain preferred embodiments of the present invention more specifically, some chemical structures in Compound (I) are exemplified below. The present invention is characterized by the substituent, W(C=V)U (wherein W, V and U have the same meanings as defined above, respectively) of Compound (I) as a matter of course, and this substituent binds to a bicyclic or tricyclic hetero ring represented by $D^1$, $D^2$, $D^3$, $D^4$, X, Y, Z and two carbon atoms, which is also a characteristic of the present invention, at the position shown in formula (I). Compounds in which X and Z each represents a nitrogen atom are one of the preferred embodiments, and compounds in which corresponding quinazoline or pyrimidine forms a condensed polycyclic hetero ring system are exemplified as group names below.

Examples of the group showing a preferred ring structure include pyrrolo[3,2-g]quinazolinyl, pyrazino[2,3-g] quinazolinyl, benzothieno[3,2-d]pyrimidinyl, thiazolo[5', 4';4,5]thieno[3,2-d]pyrimidinyl, pyrido[2',3';4,5]thieno[3,2-d]pyrimidinyl, indolo[3,2-d]pyrimidinyl, indolo[2,3-d] pyrimidinyl, benzofurano[3,2-d]pyrimidinyl, pyrimido[4,5-f]quinazolinyl, benzothieno[2,3-d]pyrimidinyl, thieno[2', 3';4,5]thieno[3,2-d]pyrimidinyl, thieno[3',2';4,5]thieno[2,3-d]pyrimidinyl, imidazo[5',4';4,5]thieno[3,2-d]pyrimidinyl, pyrido[3',2';4,5]thieno[3,2-d]pyrimidinyl, pyrrolo[2,3-d] pyrimidinyl, pyrazolo[3,4-d]pyrimidinyl, purinyl, pyrido[2, 3-d]pyrimidinyl, pyrido[3,4-d]pyrimidinyl, pyrido[4,3-d] pyrimidinyl, pyrido[3,2-d]pyrimidinyl, pyrimidino[5,4-d] pyrimidinyl, pyrimidino[4,5-d]pyrimidinyl, pyrrolo[3,2-g] quinazolinyl, pyrrolo[2,3-f]quinazolinyl, pyrazolo[4,3-g] quinazolinyl, pyrazolo[3,4-g]quinazolinyl, furo[2,3-d] pyrimidinyl, furo[3,4-d]pyrimidinyl, furo[3,2-d] pyrimidinyl, triazolo[4,5-d]pyrimidinyl, and the like, though preferred ring structures of the present invention are not limited thereto.

Examples of the pharmaceutically acceptable salt of Compound (I) include pharmaceutically acceptable acid addition salts, metal salts, ammonium salts, organic amine addition salts, amino acid addition salts, and the like. Examples of the pharmaceutically acceptable acid addition salt of Compound (I) include inorganic acid salts, such as hydrochloride, sulfate, phosphate, and the like, and organic acid salts, such as acetate, maleate, fumarate, tartrate, citrate, methanesulfonate, and the like; examples of the pharmaceutically acceptable metal salt include alkali metal salts, such as sodium salt, potassium salt, and the like, alkaline earth metal salts, such as magnesium salt, calcium salt, and the like, aluminum salt, zinc salt, and the like; examples of the pharmaceutically acceptable ammonium salt include salts such as ammonium, tetramethylammonium, and the like; examples of the pharmaceutically acceptable organic amine addition salt include addition salts of morpholine, piperidine, and the like; and examples of the pharmaceutically acceptable amino acid addition salt include addition salts of lysine, glycine, phenylalanine, and the like.

Next, processes for producing Compound (I) are described.

Production Process 1

Compound (I-a), wherein U represents $NHR^2$; and V represents an oxygen atom or a sulfur atom, can be produced according to the following reaction step.

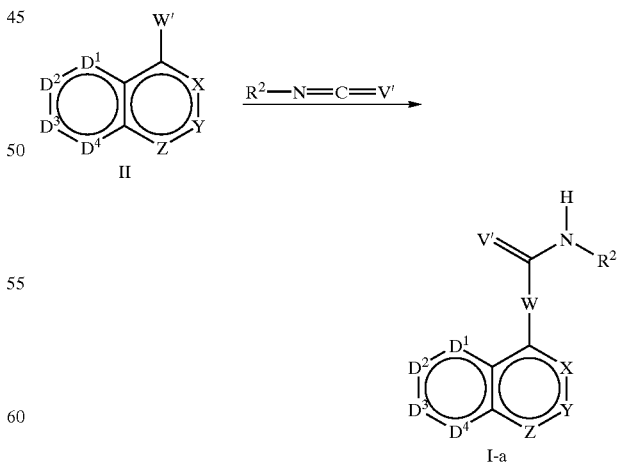

(In the formulae, $D^1$, $D^2$, $D^3$, $D^4$, $R^2$, W, X, Y and Z have the same meanings as defined above, respectively; V' represents an oxygen atom or a sulfur atom; and W' represents 1-piperazinyl or 1-homopiperazinyl in which carbons on the ring may be substituted with 1 to 4 alkyl groups which are the same or different.)

Compound (I-a) can be obtained by allowing Compound (II) to react with an isocyanate ($R^2$—N=C=O) which is commercially available or can be obtained by a known process [for example, *Organic Functional Group Preparations*, S. R. Sandler et al., 1: 305, Academic Press Inc., New York and London (1968), *Synthetic Organic Chemistry*, R. B. Wagner et al., 3rd ed., p. 640, John Wiley (1961), etc.] or with an isothiocyanate ($R^2$—N=C=S) [e.g., *Organic Functional Group Preparations*, S. R. Sandler et al., 1: 312, Academic Press Inc., New York and London (1968), *Synthetic Organic Chemistry*, R. B. Wagner et al., 3rd ed., p. 829, John Wiley (1961), etc.] at a temperature between −20° C. and the boiling point of a used solvent for 10 minutes to 48 hours in an appropriate inert solvent, for example, a halogenated hydrocarbon, such as chloroform, dichloromethane, etc., an aromatic hydrocarbon, such as benzene, toluene, etc., an ether solvent,, such as diethyl ether, tetrahydrofuran (THF), 1,4-dioxane, etc., a lower alcohol, such as methanol, ethanol, isopropanol, etc., an aprotic polar solvent, such as dimethylformamide, N-methylpyrrolidone, dimethyl sulfoxide, pyridine, etc., or a mixed solvent thereof, optionally in the presence of a base, for example, an organic base, such as triethylamine, pyridine, etc., an inorganic base, such as potassium carbonate, sodium. hydroxide, sodium hydride, etc., a metal alkoxide, such as sodium methoxide, potassium tert-butoxide, etc., or the like.

Compound (II) as the starting material can be obtained by the process disclosed in Japanese Published Unexamined Patent Application No. 104074/89, South African Patent 67 06512, *Ind. J. Chem.*, 26B: 550–555 (1987), or the like, or a modified process thereof, or can also be obtained by a process of the following reaction scheme.

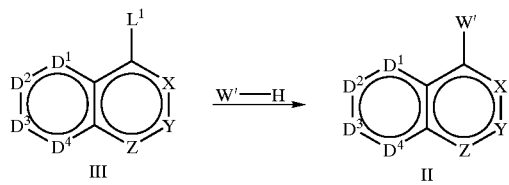

(In the formulae, $D^1$, $D^2$, $D^3$, $D^4$, W', X, Y and Z have the same meanings as defined above, respectively; and $L^1$ represents a leaving group.)

Examples of the leaving group in the definition of $L^1$ include halogen atoms, substituted or unsubstituted alkoxy groups, substituted or unsubstituted aryloxy groups, substituted or unsubstituted alkylthio groups, substituted or unsubstituted alkylsulfinyl groups, substituted or unsubstituted alkylsulfonyl groups, substituted or unsubstituted alkylsulfonyloxy groups, substituted or unsubstituted arylsulfonyloxy groups, and the like. The halogen atom, alkoxy group, aryloxy group, alkylthio group and alkylsulfinyl group have the same meanings as defined above, respectively, the alkyl moiety of the alkylsulfonyl group and alkylsulfonyloxy group has the same meaning as the alkyl group defined above, and the aryl moiety of the arylsulfonyloxy group has the same meaning as the aryl defined above. Examples of the substituent include halogen atoms, alkyl groups, a nitro group, and the like, and the halogen atom has the same meaning as the halogen atom defined above.

Compound (II) can be obtained by allowing Compound (III) to react with a compound W'—H at a temperature between room temperature and the boiling point of a used solvent for 10 minutes to 48 hours in an appropriate inert solvent, for example, a lower alcohol, such as methanol, ethanol, isopropanol, etc., a halogenated hydrocarbon, such as chloroform, dichloromethane, etc., an aromatic hydrocarbon, such as benzene, toluene, etc., an ether solvent, such as diethyl ether, THF, 1,4-dioxane, etc., an aprotic polar solvent, such as dimethylformamide, N-methylpyrrolidone, dimethyl sulfoxide, pyridine, etc., or a mixed solvent thereof, optionally in the presence of a base. Examples of the base include organic bases, such as triethylamine, pyridine, etc., inorganic bases, such as potassium carbonate, sodium hydroxide, sodium hydride, etc., metal alkoxides, such as sodium methoxide, potassium tert-butoxide, etc., and the like.

When the group defined in the above production process changes under conditions of the practical process or is inappropriate for carrying out the process, the objective compound can be obtained by introducing the compound W'—H, after its protection excluding the reaction point, into Compound (III) and then carrying out deprotection. Examples of the protecting group include protecting groups disclosed in *Protective Groups in Organic Synthesis*, T. W. Green, John Wiley & Sons Inc. (1981) and the like, such as ethoxycarbonyl, tert-butoxycarbonyl, acetyl, benzyl, and the like. Introduction and elimination of the protecting group can be carried out by a process commonly used in the synthetic organic chemistry (e.g., a process disclosed in the above *Protective Groups in Organic Synthesis* can be referred to).

A commercially available compound can be used as Compound (III) as the starting material, or Compound (III) as the starting material can be produced by the process disclosed in WO 95/19970, *J. Med. Chem.*, 38: 3780–3788 (1995), *J. Med. Chem.*, 39: 918–928 (1996), *J. Med. Chem.*, 39: 1823– 1835 (1996), *J. Med. Chem.*, 40: 1519–1529 (1997), *J. Med. Chem.*, 40: 1820–1826 (1997), *Bioorg. Med. Chem. Lett.*, 5: 2879–2884 (1995), *J. Chem. Soc.*, pp. 890–899 (1947), *J. Chem. Soc.*, pp. 561–572 (1962), *J. Chem. Soc., B*, pp. 449–454 (1967), *J. Indian Chem. Soc.*, 36: 787–791 (1959), *J. Org. Chem.*, 17: 1571–1575 (1952), *J. Med. Chem.*, 14: 1060–1066 (1971), French Patent 1388756, *J. Am. Chem. Soc.*, 68: 1204–1208 (1946), *Ind. J. Chem.*, 26B: 550–555 (1987), Japanese Published Unexamined Patent Application No. 120872/85, South African Patent 67 06512, or the like, the process described in Reference Examples, or a modified process thereof.

Production Process 2

Compound (I) can be produced according to the following reaction step.

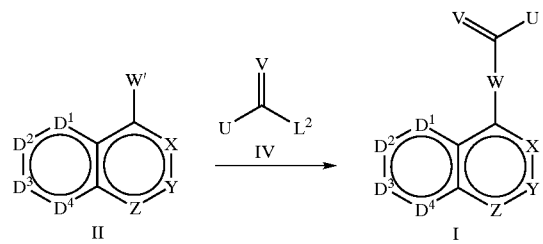

(In the formulae, $L^2$ has the same meaning as $L^1$ described above; and $D^1$, $D^2$, $D^3$, $D^4$, U, V, W, W', X, Y and Z have the same meanings as defined above, respectively.)

Compound (I) can be produced by allowing Compound (II) to react with Compound (IV) at a temperature between −20° C and the boiling point of a used solvent for 10 minutes to 48 hours in an appropriate inert solvent, for example, a halogenated hydrocarbon, such as chloroform, dichloromethane, etc., an aromatic hydrocarbon, such as benzene, toluene, etc., an ether solvent, such as diethyl ether, THF, 1,4-dioxane, etc., a lower alcohol, such as methanol, ethanol, isopropanol, etc., an aprotic polar solvent, such as dimethylformamide, N-methylpyrrolidone, dimethyl sulfoxide, pyridine, etc., or a mixed solvent thereof, optionally in the presence of a base. Examples of the base include organic. bases, such as triethylamine, pyridine, etc., inorganic bases, such as potassium carbonate, sodium hydroxide, sodium hydride, etc., metal alkoxides, such as sodium methoxide, potassium tert-butoxide, etc., and the like.

A commercially available product can be used as Compound (IV) as the starting material, or Compound (IV) as the starting material can be produced by the process described in *Beilstein*, 4: 73 (1922), *Beilstein*, 4: 75 (1922), *Bioorg. Med. Chem. Lett.*, 17: 3095–3100 (1997), *J. Med. Chem.*, 38: 3236–3245 (1995), Japanese Published Unexamined Patent Application No. 18557/78, *Jikken Kagaku Koza 20—Yuki Gosei II*, 4th ed., p. 355, The Chemical Society of Japan, Maruzen (Tokyo) (1992), *Methoden der Organischen Chemie*, vol. E11, *Organische Schwefel-Verbindungen*, Dieter Klamann, p. 263, Georg Thieme Verlag (Stuttgart, New York) (1985), or the like, or a modified process thereof.

Production Process 3

Compound (I) can also be produced according to the following reaction step.

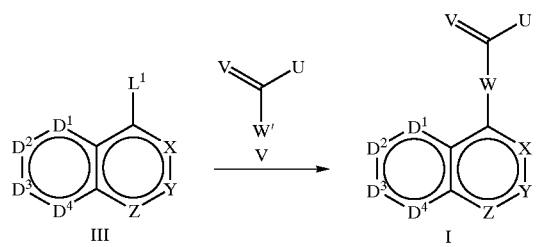

(In the formulae, $L^1$, $D^1$, $D^2$, $D^3$, $D^4$, U, V, W, W', X, Y and Z have the same meanings as defined above, respectively.)

Compound (I) can be produced by allowing Compound (III) to react with Compound (V) at a temperature between room temperature and the boiling point of a used solvent for 10 minutes to 48 hours in an appropriate inert solvent, for example, a halogenated hydrocarbon, such as chloroform, dichloromethane, etc., an aromatic hydrocarbon, such as benzene, toluene, etc., an ether solvent, such as diethyl ether, THF, 1,4-dioxane, etc., a lower alcohol, such as methanol, ethanol, isopropanol, etc., an aprotic polar solvent, such as dimethylformamide, N-methylpyrrolidone, dimethyl sulfoxide, pyridine, etc., or a mixed solvent thereof, optionally in the presence of a base. Examples of the base include organic bases, such as triethylamine, pyridine, etc., inorganic bases, such as potassium carbonate, sodium hydroxide, sodium hydride, etc., metal alkoxides, such as sodium methoxide, potassium tert-butoxide, etc., and the like.

Compound (V) as the starting material can be produced by the process disclosed in Examples or Reference Examples or a modified process thereof.

Production Process 4

Compound (I) can also be produced according to the following reaction step.

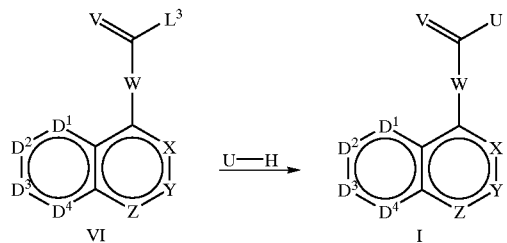

(In the formulae, $L^3$ has the same meaning as $L^1$ described above; and $D^1$, $D^2$, $D^3$, $D^4$, U, V, W, X, Y and Z have the same meanings as defined above, respectively.)

Compound (I) can be produced by allowing Compound (VI) to react with a compound U-H at a temperature between room temperature and the boiling point of a used solvent for 10 minutes to 48 hours in an appropriate inert solvent, for example, a halogenated hydrocarbon, such as chloroform, dichloromethane, etc., an aromatic hydrocarbon, such as benzene, toluene, etc., an ether solvent, such as diethyl ether, THF, 1,4-dioxane, etc., a lower alcohol, such as methanol, ethanol, isopropanol, etc., an aprotic polar solvent, such as dimethylformamide, N-methylpyrrolidone, dimethyl sulfoxide, pyridine, etc., or a mixed solvent thereof, optionally in the presence of a base. Examples of the base include organic bases, such as triethylamine, pyridine, etc., inorganic bases, such as potassium carbonate, sodium hydroxide, sodium hydride, etc., metal alkoxides, such as sodium methoxide, potassium tert-butoxide, etc., and the like.

Compound (VI) as the starting material can be produced by the process disclosed in South African Patent 67 06512, U.S. Pat. No. 3,723,434, Japanese Published Unexamined Patent Application No. 18557/78, or the like, or a modified process thereof.

Production Process 5

Compound (I-b), wherein U represents $NHR^2$; and V represents $N—R^6$, can also be produced according to the following reaction step.

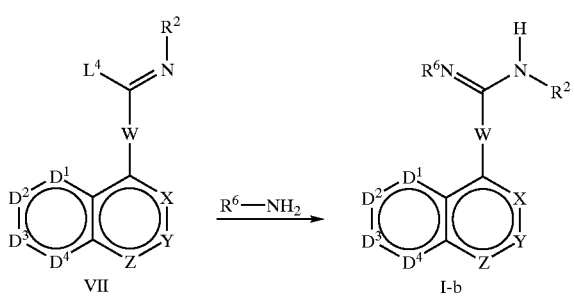

(In the formulae, $L^4$ has the same meaning as $L^1$ defined above; and $D^1$, $D^2$, $D^3$, $D^4$, $R^2$, $R^6$, W, X, Y and Z have the same meanings as defined above, respectively.)

Compound (I-b) can be produced by allowing Compound (VII) to react with a compound $R^6—NH_2$ at a temperature between room temperature and the boiling point of a used solvent for 10 minutes to 48 hours in an appropriate inert solvent, for example, a halogenated hydrocarbon, such as chloroform, dichloromethane, etc., an aromatic hydrocarbon, such as benzene, toluene, etc., an ether solvent, such as diethyl ether, THF, 1,4-dioxane, etc., a lower alcohol, such as methanol, ethanol, isopropanol, etc., an aprotic polar solvent, such as pyridine, dimethylformamide, N-methylpyrrolidone, dimethyl sulfoxide, etc., or a mixed solvent thereof; optionally in the presence of a base. Examples of the base include organic bases, such as triethylamine, pyridine, etc., inorganic bases, such as potassium carbonate, sodium hydroxide, sodium hydride, etc., metal alkoxides, such as sodium methoxide, potassium tert-butoxide, etc., and the like.

Compound (VII) as the starting material can be obtained by the process disclosed in Japanese Published Unexamined Patent Application No. 19671/77, *Organic Functional Group Preparations*, S. R. Sandler et al., 2: 166–185, Academic Press Inc., New York and London (1971), or the like, or a modified process thereof.

Production Process 6

Compound (I-c), wherein U represents $NR^1R^2$; and V represents N—CN, can also be produced according to the following reaction step.

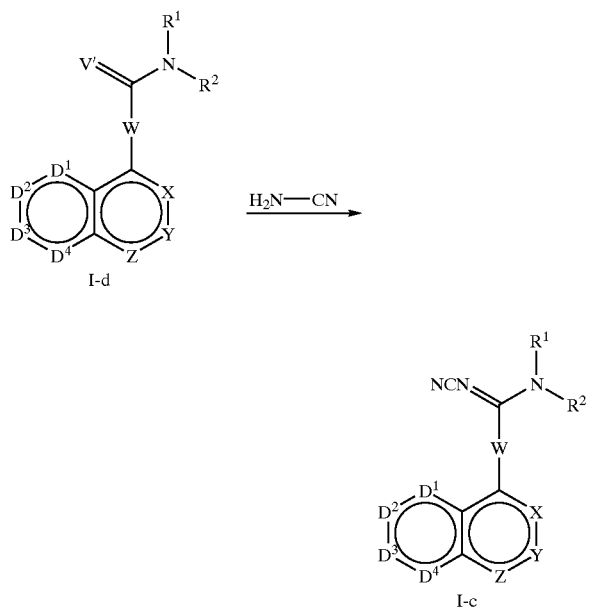

(In the formulae, $D^1$, $D^2$, $D^3$, $D^4$, $R^1$, $R^2$, V', W, X, Y and Z have the same meanings as defined above, respectively.)

Compound (I-c) can be produced by allowing Compound (I-d) to react with cyanamide at a temperature between room temperature and the boiling point of a used solvent for 10 minutes to 48 hours in an appropriate inert solvent, for example, a halogenated hydrocarbon, such as chloroform, dichloromethane, etc., an aromatic hydrocarbon, such as benzene, toluene, etc., an ether solvent, such as diethyl ether, THF, 1,4-dioxane, etc., a lower alcohol, such as methanol, ethanol, isopropanol, etc., an aprotic polar solvent, such as pyridine, dimethylformamide, N-methylpyrrolidone, dimethyl sulfoxide, pyridine, acetonitrile, etc., or a mixed solvent thereof, in the presence of an appropriate condensing agent, such as 1,3-dicyclohexylcarbodiimide, 1-ethyl-3-(3-dimethylaminopropyl)carbodiimide or the like, and optionally in the presence of a base. Examples of the base include organic bases, such as triethylamine, pyridine, etc., inorganic bases, such as potassium carbonate, sodium hydroxide, sodium hydride, etc., metal alkoxides, such as sodium methoxide, potassium tert-butoxide, etc., and the like.

Furthermore, Compound (I-b) can also be obtained by allowing Compound (II) to react with various carbodiimide compounds under conditions similar to those in Production Process 1. In addition to the commercially available product, the carbodiimide used in the reaction can be produced by the process disclosed in *Shin-Jikken Kagaku Koza 14— Yukikagobutu no Gosei to Hanno* (III), The Chemical Society of Japan, pp. 1644–1652, Maruzen (Tokyo) (1978), *Synthetic Communications*, 25: 43–47 (1995), or the like, or a modified process thereof.

When the group defined in each of the above production processes changes under conditions of the practical process or is inappropriate for carrying out the process, the objective compound can be produced by using protecting group introduction and elimination processes commonly used in the synthetic organic chemistry [e.g., see *Protective Groups in Organic Synthesis*, T. W. Greene, John Wiley & Sons Inc. (1981)]. Furthermore, a conversion of the functional group contained in each substituent can also be carried out by a commonly known process [e.g., *Comprehensive Organic Transformations*, R. C. Larock (1989), etc.] in addition to the production processes described above, and novel Compound (I) can also be derived by using some of Compounds (I) as a synthetic intermediate.

The intermediate and the objective compound in each of the above production processes can be isolated and purified by subjecting them to purification processes ordinary used in the synthetic organic chemistry, such as neutralization, filtration, extraction, washing, drying, concentration, recrystallization, various chromatography, and the like. Furthermore, the intermediates can also be used in the subsequent reaction without carrying out particular purification.

Regio isomers, geometrical isomers, optical isomers or tautomers may be present for some of Compounds (I), and all possible isomers including them and mixtures thereof are included in the scope of the present invention.

In production of a salt of Compound, (I), when Compound (I) is produced in a salt form, it can be purified as such, and when it is produced in its free form, its salt can be formed in the usual way by dissolving or suspending it in an appropriate organic solvent and adding thereto an acid or a base.

In addition, Compound (I) or a pharmaceutically acceptable salt thereof may be present in the form of addition products with water or various solvents, and these addition products are also included in the scope of the present invention.

Examples of Compound (I) obtained by the above production processes are shown in Table 1.

TABLE 1-1
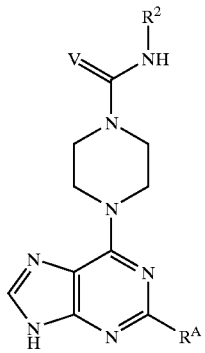
| Compound No. | V | $R^A$ | $R^2$ |
|---|---|---|---|
| 1 | O | H | 4-phenoxyphenyl |
| 2 | O | H | 4-nitrophenyl |
| 3 | S | H | -CH$_2$-phenyl |
| 4 | S | H | -CH$_2$-(3-pyridyl) |
| 5 | O | NH$_2$ | 4-phenoxyphenyl |
TABLE 1-1-continued
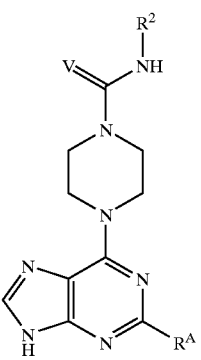
| Compound No. | V | $R^A$ | $R^2$ |
|---|---|---|---|
| 6 | O | NH$_2$ | 4-nitrophenyl |
| 7 | S | NH$_2$ | -CH$_2$-phenyl |
| 8 | S | NH$_2$ | -CH$_2$-(3-pyridyl) |
TABLE 1-2
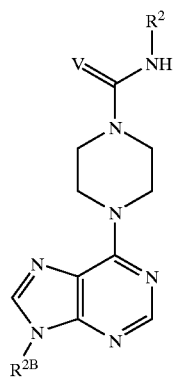
| Compound No. | V | $R^{2B'}$ | $R^2$ |
|---|---|---|---|
| 9 | O | CH$_3$ |  |

TABLE 1-2-continued

| Compound No. | V | R²ᴮ' | R² |
|---|---|---|---|
| 10 | O | 2-tetrahydropyranylmethyl | 4-phenoxyphenyl |
| 11 | S | thiocarbonyl-NH-CH₂-(pyridin-3-yl) | CH₂-(pyridin-3-yl) |

TABLE 1-3

| Compound No. | V | R² |
|---|---|---|
| 12 | O | 4-phenoxyphenyl |

TABLE 1-4

| Compound No. | V | R²ᴮ' | R² |
|---|---|---|---|
| 13 | O | CH₃ | 4-phenoxyphenyl |

TABLE 1-4-continued
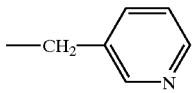
| Compound No. | V | R^{2B'} | R^2 |
|---|---|---|---|
| 14 | S | CH$_3$ | —CH$_2$-(3-pyridyl) |
| 15 | S | CH$_3$ | —CH$_2$-phenyl |
| 16 | O | phenyl- | -phenyl-O-phenyl (4-phenoxyphenyl) |
| 17 | S | phenyl- | —CH$_2$-(3-pyridyl) |
TABLE 1-5
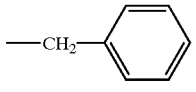
| Compound No. | V | R$^2$ |
|---|---|---|
| 18 | O | 4-phenoxyphenyl |
| 19 | S | —CH$_2$-(4-chlorophenyl) |
TABLE 1-6
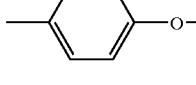
| Compound No. | V | R$^2$ |
|---|---|---|
| 20 | O | 4-phenoxyphenyl |
| 21 | S | —CH$_2$-phenyl |
TABLE 1-7
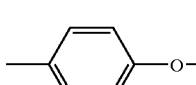
| Compound No. | Z | R$^A$ | R$^C$ |
|---|---|---|---|
| 22 | N | H | F |
| 23 | CH | NH$_2$ | H |

TABLE 1-8
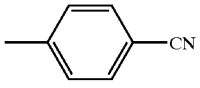
| Compound No. | V | R² |
|---|---|---|
| 24 | O | 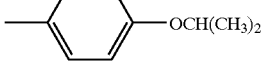 |
| 25 | O | 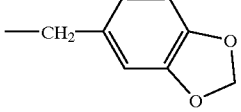 |
| 26 | S | 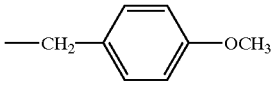 |
| 27 | S | 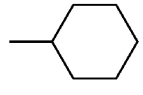 |
TABLE 1-9
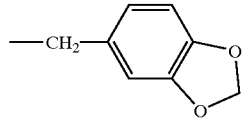
| Compound No. | R^E |
|---|---|
| 28 | H |
| 29 | 2-Cl |
| 30 | 3-Cl |
| 31 | 4-Cl |
| 32 | 4-F |
| 33 | 4-Br |
| 34 | 4-CH₃ |
| 35 | 4-CH(CH₃)₂ |
| 36 | 4-OCH₃ |
TABLE 1-9-continued
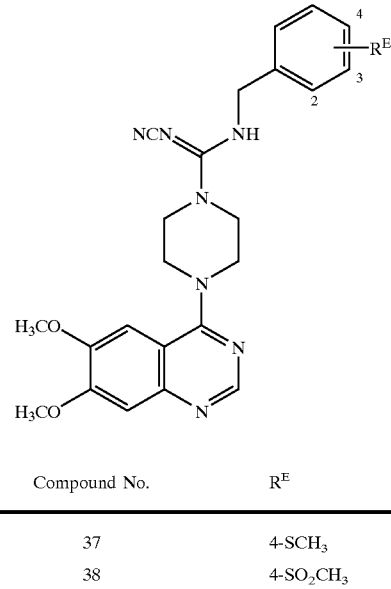
| Compound No. | R^E |
|---|---|
| 37 | 4-SCH₃ |
| 38 | 4-SO₂CH₃ |
TABLE 1-10
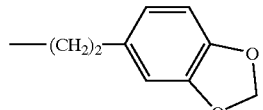
| Compound No. | R² |
|---|---|
| 39 | —(CH₂)₃CH₃ |
| 40 | (cyclohexyl) |
| 41 | —CH₂-(benzodioxole) |
| 42 | —(CH₂)₂-(benzodioxole) |

TABLE 1-11
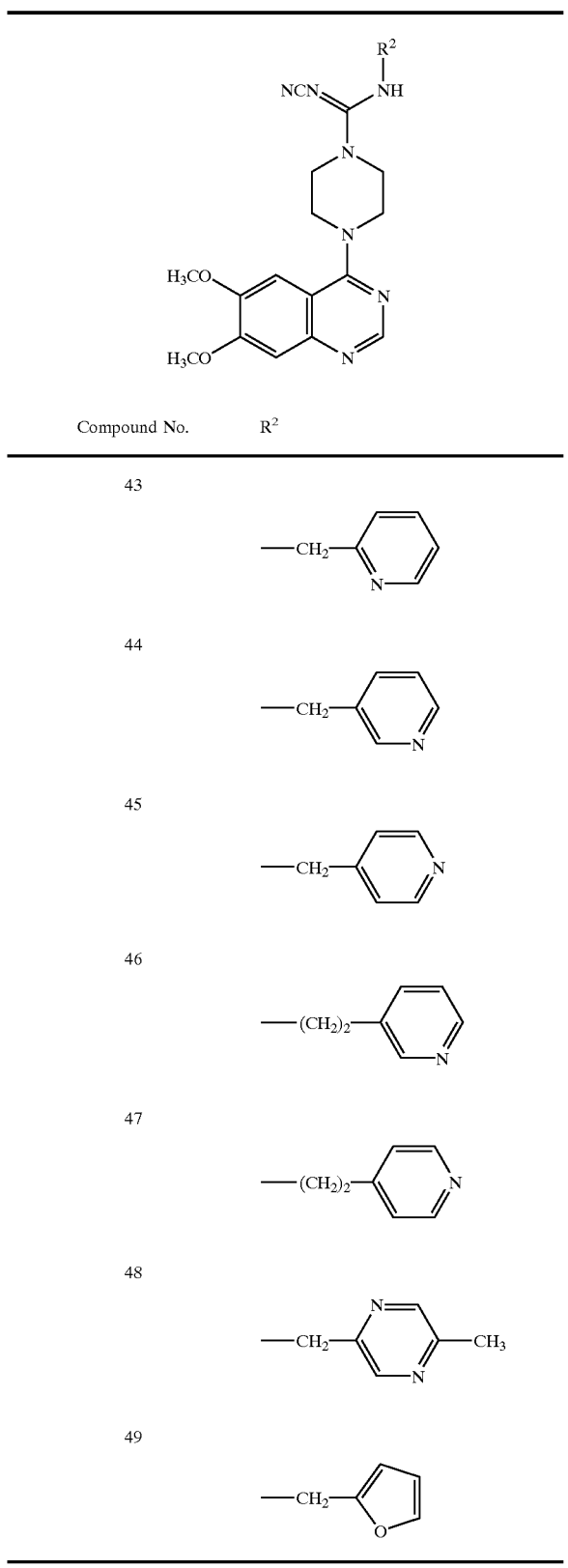
| Compound No. | R² |
|---|---|
| 43 | —CH₂-(2-pyridyl) |
| 44 | —CH₂-(3-pyridyl) |
| 45 | —CH₂-(4-pyridyl) |
| 46 | —(CH₂)₂-(3-pyridyl) |
| 47 | —(CH₂)₂-(4-pyridyl) |
| 48 | —CH₂-(5-methylpyrazin-2-yl) |
| 49 | —CH₂-(2-furyl) |
TABLE 1-12
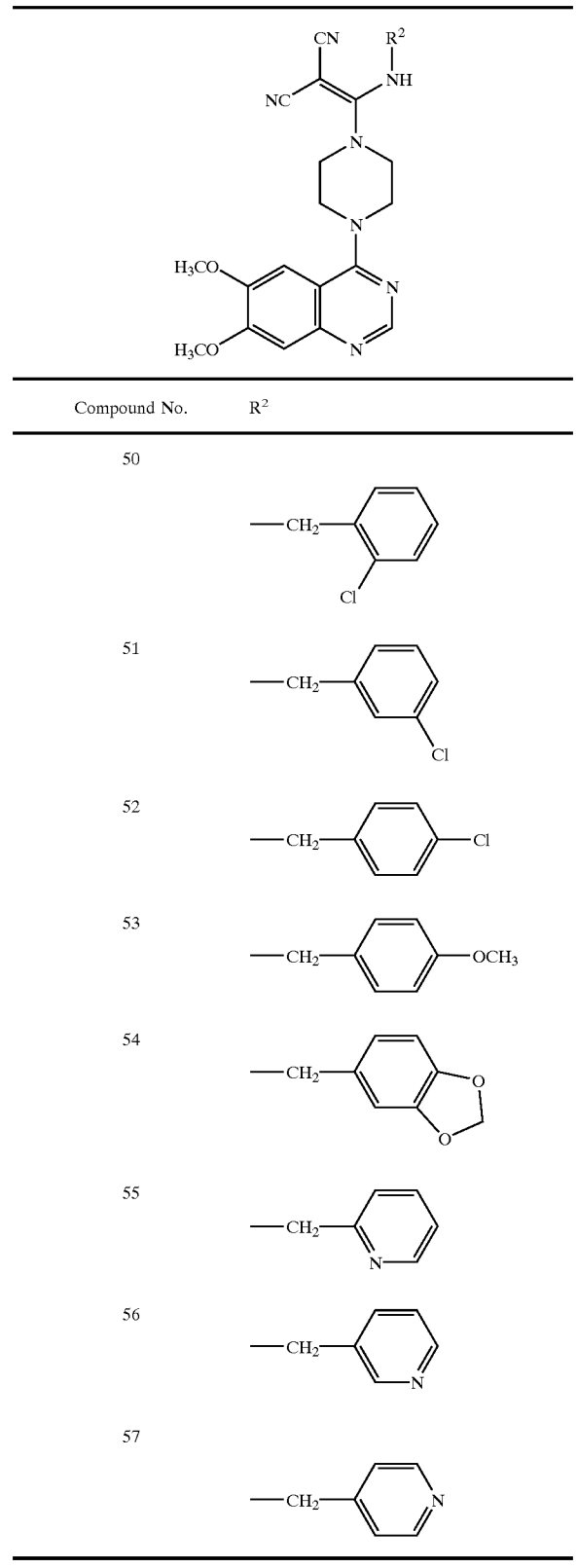
| Compound No. | R² |
|---|---|
| 50 | —CH₂-(2-chlorophenyl) |
| 51 | —CH₂-(3-chlorophenyl) |
| 52 | —CH₂-(4-chlorophenyl) |
| 53 | —CH₂-(4-methoxyphenyl) |
| 54 | —CH₂-(benzo[1,3]dioxol-5-yl) |
| 55 | —CH₂-(2-pyridyl) |
| 56 | —CH₂-(3-pyridyl) |
| 57 | —CH₂-(4-pyridyl) |

TABLE 1-13

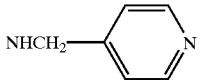

| Compound No. | V | U |
|---|---|---|
| 58 | CH(NO$_2$) | SCH$_3$ |
| 59 | CH(NO$_2$) | NHCH$_2$-(4-pyridyl) |
| 60 | CH(NO$_2$) | NHCH$_2$-(benzodioxole) |
| 61 | N-cyclohexyl | NH-cyclohexyl |
| 62 | N-SO$_2$-C$_6$H$_4$-CH$_3$ | SCH$_3$ |
| 63 | N-SO$_2$-C$_6$H$_4$-CH$_3$ | NHCH$_2$-(benzodioxole) |
| 64 | C(CN)$_2$ | SCH$_3$ |

TABLE 1-14

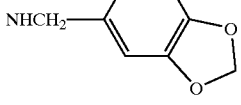

| Compound No. | V | U |
|---|---|---|
| 65 | NCN | SCH$_3$ |
| 66 | NCN | OCH$_2$CH$_3$ |

TABLE 1-14-continued

| Compound No. | V | U |
|---|---|---|
| 67 | NCN | O-C$_6$H$_5$ |
| 68 | NCN | HN-C$_6$H$_3$(OCH$_3$)$_2$ |

TABLE 1-15

| Compound No. | A |
|---|---|
| 69 | 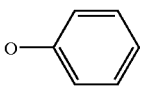 |
| 70 | 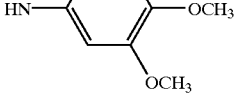 |

Next, the pharmacological activity of the compounds of the present invention are specifically explained by test examples.

Test Example 1
PDGF Receptor Phosphorylation Inhibition Test

This test was carried out according to the process disclosed in a literature [*J. Biol. Chem.*, 266: 413–418 (1991)]. In this case, Chinese hamster ovary (CHO) cells to which human β-PDGF receptor cDNA had been inserted and in which it had been expressed were used in the test. The test results were represented by a concentration at which the test compound inhibits 50% of the PDGF receptor phosphorylation (IC$_{50}$).

The results are shown in Table 2.

TABLE 2

| | PDGF receptor phosphorylation inhibition IC$_{50}$ ($\mu$M) |
|---|---|
| Compound 1 | 0.29 |
| Compound 3 | 0.89 |
| Compound 5 | 0.20 |
| Compound 31 | 0.38 |
| Compound 41 | 0.19 |

Test results on Compounds 22, 50, 52, 63 and 66 were represented by a ratio (%) of inhibiting phosphorylation of the PDGF receptor at 10 $\mu$M, with the results shown in Table 3.

TABLE 3

| | PDGF receptor phosphorylation inhibition (%) |
|---|---|
| Compound 22 | 66 |
| Compound 51 | 82 |
| Compound 53 | 87 |
| Compound 64 | 82 |
| Compound 67 | 95 |

Although Compound, (I) or a pharmaceutically acceptable salt thereof can be administered directly as such, generally, it is preferred to provide it in various forms of pharmaceutical preparations. Further, such pharmaceutical preparations are used for animals and humans.

As their route of administration, it is preferred to use the most effective way in carrying out the treatment, and examples include oral administration and parenteral administration, such as rectal, buccal, subcutaneous, intramuscular, intravenous, and the like.

Examples of the dosage form include capsules, tablets, granules, powders, syrups, emulsions, suppositories, injections, and the like.

Liquid preparations suitable for oral administration, such as emulsions or syrups, can be produced using water, saccharides, such as sucrose, sorbitol, fructose, etc., glycols, such as polyethylene glycol, polypropylene glycol, etc., oils, such as sesame oil, olive oil, soybean oil, etc., antiseptics, such as p-hydroxybenzoic acid esters, etc., flavors, such as strawberry flavor, peppermint, etc., and the like. Furthermore, capsules, tablets, powders, granules and the like can be produced using excipients, such as lactose, glucose, sucrose, mannitol, etc., disintegrators, such as starch, sodium alginate, etc., lubricants, such as magnesium stearate, talc, etc., binders, such as polyvinyl alcohol, hydroxypropylcellulose, gelatin, etc., surfactants, such as fatty acid esters, etc., plasticizers, such as glycerol, etc., and the like.

Preparations suitable for parenteral administration preferably comprise an aqueous sterile preparation containing the active compound which is isotonic with blood of the recipient. For example, in the case of injections, a solution for injection is prepared using a carrier, such as a salt solution, a glucose solution, or a mixture of a brine and a glucose solution, or the like.

Topical preparations are produced by dissolving or suspending the active compound in at least one of media, such as mineral oil, petroleum, polyhydric alcohol, and the like, or in other bases usually used in topical pharmaceutical preparations.

Preparations for rectal administration are produced using usual carriers, such as cacao butter, hydrogenated fat, hydrogenated fat carboxylic acid, and the like, and are provided as suppositories.

Furthermore, at least one auxiliary component selected from the glycols, oils, flavors, antiseptics (including antioxidants), excipients, disintegrators, lubricants, binders, surfactants, plasticizers, and the like which are exemplified in the oral preparations can also be added to these parenteral preparations.

An effective dose and frequency of administration of Compound (I) or a pharmaceutically acceptable salt thereof may vary depending on the dosage form, age and body weight of each patient, properties or seriousness of the symptoms to be treated and the like; however, the dose is generally 0.01 to 1,000 mg/man, preferably 5 to 500 mg/man, per day, and as to the administration frequency, it is preferred to administer it once a day or by dividing the daily dose.

The compounds of the present invention can be directly applied to a therapeutic use as kinase inhibitors, particularly as those which are related to tyrosine kinase, for controlling kinase-dependent diseases in mammals. Compounds having an IC$_{50}$ value between 10 nM and 10 $\mu$M are particularly preferred. It is possible to select a specific compound of the present invention which has the ability of inhibiting selectively one of the three protein kinase (a kinase which phosphorylates tyrosine, a kinase which phosphorylates tyrosine and threonine, and a kinase which phosphorylates threonine). The tyrosine kinase-dependent diseases include over-proliferative malfunctions which are initiated/maintained by abnormal tyrosine kinase enzyme activity. Examples include psoriasis, pulmonary fibrosis, glomerulonephritis, cancers, atherosclerosis, and anti-angiogenesis (e.g., tumor proliferation or diabetic retinopathy). Although relationships of other classes of kinase to specific diseases are not well known, it is considered that a selective tyrosine kinase-inhibiting compound has a useful therapeutic effect. Also, it is understood that other classes of kinase have their own useful therapeutic effects. Quercetin, genistein and staurosporin which are tyrosine kinase inhibitors inhibit many other protein kinase in addition to the tyrosine kinase, and have strong cytotoxicity as a result of the lack of specificity for them. Accordingly, tyrosine kinase inhibitors (or inhibitors of other kinase) which are apt to induce undesirable side effects due to lack of selectivity can be identified using a usual test for measuring cytotoxicity.

Examples, Reference Examples and Formulation Examples of the present invention are shown below; however, the present invention is not limited thereto.

BEST MODE FOR CARRYING OUT THE INVENTION

EXAMPLE 1

N-(4-Phenoxyphenyl)-4-(6-purinyl)-1-piperazinecarboxamide (Compound 1)

To a methylene chloride solution (50 mL) of 4-[N-(4-phenoxyphenyl)carbamoyl]-1-piperazinecarboxylic acid tert-butyl ester (4.57 g, 11.51 mmol) produced in Reference Example 1, trifluoroacetic acid (60 mL) was added under ice-cooling, followed by stirring at the same temperature for 2.5 hours. After concentration of the reaction solution, the resulting residue was dissolved in a mixed solvent of dimethylformamide (24 mL) and triethylamine (8 mL), and 6-chloropurine (2.58 g, 16.69 mmol) was added thereto, followed by stirring in argon atmosphere at room temperature overnight. The reaction solution was poured into water, and the precipitated crystals were recovered by filtration, washed with water, dried, and then purified by silica gel column chromatography to give the target compound (3.41 g, 8.22 mmol) as colorless crystals.

Yield: 71%

Melting point: 250–251° C.

$^1$H-NMR (DMSO-$d_6$) δ (ppm): 13.20 (1H, br), 8.65 (1H, brs), 8.25 (1H, s), 8.17 (1H, s), 7.49 (2H, d, J=8.9 Hz), 7.39–7.33 (2H, m), 7.08 (1H, m), 6.96–6.93 (4H, m), 4.27 (4H, m), 3.60–3.58 (4H, m).

FAB-Mass: 416 ((M+1)$^+$)

IR (KBr tablet method) ν (cm$^{-1}$): 1637, 1579, 1535, 1506, 1489, 1423, 1227, 1022, 996, 937, 851, 748, 644.

EXAMPLE 2

N-(4-Nitrophenyl)-4-(6-purinyl)-1-piperazinecarboxamide (Compound 2)

To a methylene chloride solution (10 mL) of 4-(6-purinyl)-1-piperazinecarboxylic acid tert-butyl ester (500 mg, 1.64 mmol) disclosed in Japanese Published Unexamined Patent Application No. 104074/89, trifluoroacetic acid (10 mL) was added under ice-cooling, followed by stirring at the same temperature for 1 hour. After concentration of the reaction solution, the resulting residue was subjected to an azeotropic treatment with toluene, and dissolved in a mixed solvent of dimethylformamide (10 mL) and triethylamine (1.21 mL, 8.68 mmol), and 4-nitrophenyl isocyanate (290 mg, 1.77 mmol) was added thereto, followed by stirring overnight at room temperature in argon atmosphere. The reaction solution was poured into water, and the precipitated crystals were recovered by filtration, washed with water, dried, and then purified by silica gel column chromatography to give the target compound (410 mg, 1.11 mmol) as colorless crystals.

Yield: 68%

Melting point: 270–275° C. (decomposed)

$^1$H-NMR (DMSO-$d_6$) δ (ppm): 13.09 (1H, br), 9.34 (1H, brs), 8.26 (1H, s), 8.18 (1H, s), 8.17 (2H, d, J=9.2 Hz), 7.76 (2H, d, J=9.2 Hz), 4.29 (4H, m), 3.65–3.63 (4H, m).

FAB-Mass: 369 ((M+1)$^+$)

IR (KBr tablet method) ν (cm$^{-1}$): 1668, 1581, 1541, 1500, 1417, 1329, 1296, 1240, 1174, 1111, 990, 939, 847.

EXAMPLE 3

N-Benzyl-4-(6-purinyl)-1-piperazinethiocarboxamide (Compound 3)

The target compound was produced in the same manner as in Example 2, except that 4-nitrophenyl isocyanate was replaced with benzyl isothiocyanate.

Yield: 70%

Melting point: 255–260° C.

$^1$H-NMR (DMSO-$d_6$) δ (ppm): 13.09 (1H, br), 8.33 (1H, brt, J=5.3 Hz), 8.25 (1H, s), 8.17 (1H, s), 7.32–7.20 (5H, m), 4.84 (2H, d, J=5.3 Hz), 4.27 (4H, m), 4.03–3.99 (4H, m).

FAB-Mass: 354 ((M+1)$^+$)

IR (KBr tablet method) ν (cm$^{-1}$): 1585, 1527, 1321, 1259, 1207.

EXAMPLE 4

4-(6-Purinyl)-N-(3-pyridylmethyl)-1-piperazinethiocarboxamide dihydrochloride (Compound 4)

A free form of the target compound was produced in the same manner as in Example 2, except that 4-nitrophenyl isocyanate was replaced with 3-pyridylmethyl isothiocyanate. To an ethyl acetate suspension (20 mL) of the free form (443 mg, 1.25 mmol), a 4 N hydrogen chloride-ethyl acetate solution (6.25 mL, 25 mmol) was added under ice-cooling, followed by stirring at the same temperature for 15 minutes. Crystals obtained by filtering the reaction solution were washed with ethyl acetate, and dried to give the target compound (471 mg, 1.21 mmol).

Yield: 73%

Melting point (hydrochloride): 178–185° C.

$^1$H-NMR (free form, DMSO-$d_6$) δ (ppm): 13.06 (1H, br), 8.55 (1H, d, J=2.3 Hz), 8.45 (1H, dd, J=4.6 Hz, 1.7 Hz), 8.38 (1H, brt, J=5.3 Hz), 8.26 (1H, s), 8.17 (1H, s), 7.74 (1H, ddd, J=7.9 Hz, 2.3 Hz, 1.7 Hz), 7.34 (1H, dd, J=7.9 Hz, 4.6 Hz), 4.85 (2H, d, J=5.3 Hz), 4.29 (4H, m), 4.04–4.00 (4H, m).

FAB-Mass: 355 ((M+1)$^+$)

IR (hydrochloride, KBr tablet method) ν (cm$^{-1}$): 1633, 1539, 1410, 1257, 1007, 930.

In the following Examples 5 to 7, the target compounds were produced in the same manner as in Example 2, except that 4-(6-purinyl)-1-piperazinecarboxylic acid tert-butyl ester was replaced with 4-(2-amino-6-purinyl)-1-piperazinecarboxylic acid tert-butyl ester produced in Reference Example 2, and that 4-nitrophenyl isocyanate was replaced with a corresponding isocyanate or isothiocyanate.

EXAMPLE 5

4-(2-Amino-6-purinyl)-N-(4-phenoxyphenyl)-1-piperazinecarboxamide (Compound 5)

Yield: 95%

Melting point: 244–258° C.

$^1$H-NMR (DMSO-$d_6$) δ (ppm): 12.23 (1H, br), 8.63 (1H, brs), 7.72 (1H, s), 7.48 (2H, d, J=9.2 Hz), 7.39–7.33 (2H, m), 7.08 (1H, m), 6.98–6.93 (4H, m), 5.80 (2H, brs), 4.22–4.13 (4H, m), 3.59–3.54 (4H, m).

FAB-Mass: 431 ((M+1)$^+$)

IR (KBr tablet method) ν (cm$^{-1}$): 1641, 1601, 1568, 1508, 1489, 1414, 1230, 997, 933, 835, 785, 743, 690, 635.

EXAMPLE 6

4-(2-Amino-6-purinyl)-N-(4-nitrophenyl)-1-piperazinecarboxamide (Compound 6)

Yield: 28%

Melting point: 208–214° C.

$^1$H-NMR (DMSO-$d_6$) δ (ppm): 9.31 (1H, brs), 8.17 (2H, d, J=9.2 Hz), 7.74 (2H, d, J=9.2 Hz), 7.73 (1H, s), 5.80 (2H, brs), 4.20–4.19 (4H, m), 3.60–3.58 (4H, m).

FAB-Mass: 384 ((M+1)$^+$)

IR (KBr tablet method) ν (cm$^{-1}$): 1662, 1610, 1572, 1489, 1329, 1301, 1244, 1113, 997, 752.

EXAMPLE 7

4-(2-Amino-6-purinyl)-N-benzyl-1-piperazinethiocarboxamide (Compound 7)

Yield: 37%

Melting point: 242–245° C.

$^1$H-NMR (DMSO-$d_6$) δ (ppm): 12.23 (1H, brs), 8.31 (1H, brt, J=5.3 Hz), 7.71 (1H, s), 7.32–7.20 (5H, m), 5.81 (2H, brs), 4.84 (2H, d, J=5.3 Hz), 4.17 (4H, m), 3.96 (4H, m).

FAB-Mass: 369 ((M+1)$^+$)

IR (KBr tablet method) ν (cm$^{-1}$): 1614, 1578, 1527, 1491, 1450, 1398, 1304, 1248, 1192, 1000, 944.

EXAMPLE 8

4-(2-Amino-6-purinyl)-N-(3-pyridylmethyl)-1-piperazinethiocarboxamide dihydrochloride (Compound 8)

The target compound was produced in the same manner as in Example 4, except that 4-(6-purinyl)-1-piperazinecarboxylic acid tert-butyl ester was replaced with 4-(2-amino-6-purinyl)-1-piperazinecarboxylic acid tert-butyl ester produced in Reference Example 2.

Yield: 39%

Melting point (hydrochloride): 180–185° C. (decomposed)

$^1$H-NMR (free form, DMSO-d$_6$) δ (ppm): 12.22 (1H, br), 8.53 (1H, d, J=1.7 Hz), 8.44 (1H, dd, J=4.6 Hz, 1.7 Hz), 8.34 (1H, brt, J=5.0 Hz), 7.72 (1H, m), 7.71 (1H, s), 7.34 (1H, dd, J=7.6 Hz, 4.6 Hz), 5.80 (2H, brs), 4.83 (2H, d, J=5.0 Hz), 4.21–4.14 (4H, m), 3.97–3.93 (4H, m).

FAB-Mass: 370 ((M+1)$^+$)

IR (hydrochloride, KBr tablet method) ν (cm$^{-1}$): 1653, 1618, 1541, 1527, 1524, 1000.

EXAMPLE 9

4-(9-Methyl-6-purinyl)-N-(4-phenoxyphenyl)-1-piperazinecarboxamide (Compound 9)

The target compound was produced in the same manner as in Example 2, except that 4-(6-purinyl)-1-piperazinecarboxylic acid tert-butyl ester was replaced with 4-(9-methyl-6-purinyl)-1-piperazinecarboxylic acid tert-butyl ester disclosed in Japanese Published Unexamined Patent Application No. 104074/89, and that 4-nitrophenyl isocyanate was replaced with 4-phenoxyphenyl isocyanate.

Yield: 91%

Melting point: 168–169° C.

$^1$H-NMR (CDCl$_3$) δ (ppm): 8.39 (1H, s), 7.73 (1H, s), 7.36–7.27 (4H, m), 7.05 (1H, m), 6.98–6.95 (4H, m), 6.59 (1H, brs), 4.38 (4H, m), 3.82 (3H, s), 3.68–3.64 (4H, m).

FAB-Mass: 430 ((M+1)$^+$)

IR (KBr tablet method) ν (cm$^{-1}$): 1637, 1587, 1537, 1506, 1489, 1425, 1252, 1227, 1001, 851, 748, 642.

EXAMPLE 10

(dl) -4-[9-(2-Tetrahydropyranyl)-6-purinyl]-N-(4-phenoxyphenyl)-1-piperazinecarboxamide (Compound 10)

The target compound was produced in the same manner as in Example 1, except that 6-chloropurine was replaced with commercially available (dl )-6-chloro-9-(2-tetrahydropyranyl)purine.

Yield: 74%

Melting point: 227–228° C.

$^1$H-NMR (CDCl$_3$) δ (ppm): 8.38 (1H, s), 7.98 (1H, s), 7.35–7.24 (4H, m), 7.12–6.90 (5H, m), 6.48 (1H, brs), 5.74 (1H, dd, J=9.9 Hz, 2.5 Hz), 4.39 (4H, m), 4.17 (1H, m), 3.83–3.61(5H, m), 2.12–1.95 (2H, m), 1.81–1.67 (4H, m).

FAB-Mass: 500 ((M+1)$^+$)

IR (KBr tablet method) ν (cm$^{-1}$): 1630, 1587, 1533, 1508, 1473, 1425, 1248, 1221, 995.

EXAMPLE 11

N-(3-Pyridylmethyl)-4-{9-[N-(3-pyridylmethyl)thiocarbamoyl]-6-purinyl}-1-piperazinethiocarboxamide (Compound 11)

To a dimethylformamide solution (10 mL) of 6-(1-piperazinyl)purine (335 mg, 1.64 mmol) produced in Reference Example 3, triethylamine (0.92 mL, 6.60 mmol) and 3-picolyl isothiocyanate hydrobromide (916 mg, 3.96 mmol) were added, followed by stirring overnight at room temperature. The reaction solution was poured into water, sodium chloride was added thereto, and the precipitated crystals were recovered by filtration, washed with water, dried, and purified by silica gel column chromatography to give the target compound (204 mg, 0.40 mmol).

Yield: 25%

Melting point: 143–144° C.

$^1$H-NMR (CDCl$_3$) δ (ppm): 11.93 (1H, brt, J=5.6 Hz), 8.93 (1H, d, J=5.6 Hz), 8.69 (1H, d, J=2.3 Hz), 8.57 (1H, m), 8.54–8.45 (2H, m), 8.28 (1H, s), 7.81–7.76 (2H, m), 7.35–7.25 (2H, m), 6.44 (1H, brt, J=5.3 Hz), 5.07 (2H, d, J=5.6 Hz), 4.95 (2H, d, J=5.3 Hz), 4.57–4.15 (4H, br), 4.10–4.07 (4H, m).

FAB-Mass: 505 ((M+1)$^+$)

IR (KBr tablet method) ν (cm$^{-1}$): 1728, 1601, 1560, 1477, 1425, 1379, 1325, 1254, 789, 712.

EXAMPLE 12

4-(5-Carbamoyl-1,3-dimethyl-4-1H-pyrazolo[3,4-b]pyridyl)-N-(4-phenoxyphenyl)-1-piperazinecarboxamide (Compound 12)

The target compound was produced in the same manner as in Example 2, except that 4-(6-purinyl)-1-piperazinecarboxylic acid tert-butyl ester was replaced with 4-(5-carbamoyl-1,3-dimethyl-4-1H-pyrazolo[3,4-b]pyridyl)-1-piperazinecarboxylic acid tert-butyl ester produced in Reference Example 4, and that 4-nitrophenyl isocyanate was replaced with 4-phenoxyphenyl isocyanate.

Yield: quantitative

Melting point: 248–250° C.

$^1$H-NMR (DMSO-d$_6$) δ (ppm): 8.69 (1H, s), 8.26 (1H, s), 7.99 (1H, brs), 7.58 (1H, brs), 7.49 (2H, d, J=8.9 Hz), 7.36 (2H, m), 7.08 (1H, m), 6.96–6.93 (4H, m), 3.92 (3H, s), 3.66 (4H, m), 3.30 (4H, m), 2.64 (3H, s).

FAB-Mass: 486 ((M+1)$^+$)

IR (KBr tablet method) ν (cm$^{-1}$): 1649, 1583, 1558, 1508, 1489, 1417, 1381, 1248, 1228.

EXAMPLE 13

4-(1-Methyl-4-1H-pyrazolo[3,4-d]pyrimidinyl)-N-(4-phenoxyphenyl)-1-piperazinecarboxamide (Compound 13)

To a dimethylformamide solution (10 mL) of 1-methyl-4-(1-piperazinyl)-1H-pyrazolo[3,4-d]pyrimidine (482 mg, 2.21 mmol) produced in Reference Example 5, 4-phenoxyphenyl isocyanate (0.47 mL, 2.23 mmol) was added, followed by stirring overnight at room temperature. The reaction solution was poured into water, and the precipitated crystals were recovered by filtration, washed with water, dried, and then purified by silica gel column chromatography to give the target compound (770 mg, 1.79 mmol) as colorless crystals.

Yield: 81%

Melting point: 155–156° C.

$^1$H-NMR (CDCl$_3$) δ (ppm): 8.39 (1H, s), 7.93 (1H, s), 7.35–7.25 (4H, m), 7.06 (1H, m), 6.97–6.93 (4H, m), 6.75 (1H, brs), 4.12–4.08 (4H, m), 4.03 (3H, s), 3.79–3.75 (4H, m).

FAB-Mass: 430 ((M+1)$^+$)

IR (KBr tablet method) ν (cm$^{-1}$): 1664, 1578, 1506,1489, 1416, 1342, 1292, 1230, 993, 924, 750.

In the following Examples 14 and 15, the target compounds were produced in the same manner as in Example 13, except that 4-phenoxyphenyl isocyanate was replaced with a corresponding isothiocyanate.

EXAMPLE 14

N-Benzyl-4-(1-methyl -4-1H-pyrazolo[3,4-d] pyrimidinyl)-1-piperazinethiocarboxamide (Compound 15)

Yield: 78%

Melting point: 175–176° C.

$^1$H-NMR (CDCl$_3$) δ (ppm): 8.36 (1H, m), 7.91 (1H, s), 7.35–7.29 (5H, m), 5.86 (1H, brt, J=5.0 Hz), 4.88 (2H, d, J=5.0 Hz), 4.17 (8H, m), 4.01 (3H, s).

FAB-Mass: 368 ((M+1)$^+$)

IR (KBr tablet method) ν (cm$^{-1}$) 1581, 1558, 1541, 1525, 1408, 1383, 1336.

EXAMPLE 15

4-(1-Methyl-4-1H-pyrazolo[3,4-d]pyrimidinyl)-N-(3-pyridylmethyl)-1-piperazinethiocarboxamide (Compound 14)

Yield: 92%

Melting point: 210–211° C.

$^1$H-NMR (CDCl$_3$) δ (ppm): 8.39 (2H, m) , 8.33 (1H, s), 7.91 (1H, s), 7.77 (1H, d, J=7.9 Hz), 7.24 (1H, dd, J=7.9 Hz, 5.0 Hz), 7.14 (1H, brt, J=5.3 Hz), 4.91 (2H, d, J=5.3 Hz), 4.18–4.16 (8H, m), 3.99 (3H, s).

FAB-Mass: 369 ((M+1)$^+$)

IR (KBr tablet method) ν (cm$^{-1}$): 1560, 1446, 1417, 1363, 1333, 1275, 1184, 989, 787.

EXAMPLE 16

N-(4-Phenoxyphenyl)-4-(1-phenyl-4-1H-pyrazolo[3, 4-d]pyrimidinyl)-1-piperazinecarboxamide (Compound 16)

The target compound was produced in the same manner as in Example 13, except that 1-methyl-4-(1-piperazinyl)-1H-pyrazolo[3,4-d]pyrimidine was replaced with 1-phenyl-4-(1-piperazinyl)-1H-pyrazolo[3,4-d]pyrimidine produced in Reference Example 6

Yield: 91%

FAB-Mass: 492 ((M+1)$^+$)

EXAMPLE 17

4-(1-Phenyl-4-1H-pyrazolo[3,4-d]pyrimidinyl)-N-(3-pyridylmethyl)-1-piperazinethiocarboxamide dihydrochloride (Compound 17)

A free form of the target compound was produced in the same manner as in Example 13, except that 1-methyl-4-(1-piperazinyl)-1H-pyrazolo[3,4-d]pyrimidine was replaced with 1-phenyl-4-(1-piperazinyl)-1H-pyrazolo[3,4-d] pyrimidine produced in Reference Example 6, and that 4-phenoxyphenyl isocyanate was replaced with 3-pyridylmethyl isocyanate. Then, the hydrochloride treatment was carried out in the same manner as in Example 4 to give the target compound.

Yield: 56%

Melting point (hydrochloride): 160–163° C.

$^1$H-NMR (free form, DMSO-d$_6$) δ (ppm): 8.58–8.56 (2H, s), 8.45–8.42 (2H, m), 8.32 (1H, s), 8.20 (2H, d, J=7.6 Hz), 7.74 (1H, m), 7.59–7.53 (2H, m), 7.39–7.32 (2H, m), 4.84 (2H, d, J=5.0 Hz), 4.13 (8H, m).

FAB-Mass: 431 ((M+1)$^+$)

IR (hydrochloride, KBr tablet method) ν (cm$^{-1}$) 1645, 1593, 1537, 1500, 1410, 1221, 974, 770, 681.

In the following Examples 18 and 19, the target compounds were produced in the same manner as in Example 13, except that 1-methyl-4-(1-piperazinyl)-1H-pyrazolo[3, 4-d]pyrimidine was replaced with 4-(1-piperazinyl)-5,6-tetramethylenethieno[2,3-d]pyrimidine produced in Reference Example 7, and that 4-phenoxyphenyl isocyanate was replaced with a corresponding isocyanate or isothiocyanate.

EXAMPLE 18

N-(4-Phenoxyphenyl)-4-(5,6-tetramethylene-4-thieno[2,3-d]-pyrimidinyl )-1-piperazinecarboxamide (Compound 18)

Yield: 94%

Melting point: 183–184° C.

$^1$H-NMR (CDCl$_3$ ) δ (ppm): 8.55 (1H, s), 7.35–7.26 (4H, m), 7.07 (1H, m), 6.99–6.96 (4H, m), 6.50 (1H, brs) , 3.70–3.67 (4H, m), 3.49–3.45 (4H, m), 2.96–2.88 (4H, m), 2.00–1.92 (2H, m), 1.89–1.81 (2H, m).

FAB-Mass: 486 ((M+1)$^+$)

IR (KBr tablet method) ν (cm$^{-1}$): 1643, 1531, 1506, 1489, 1416, 1225, 991.

EXAMPLE 19

N-(4-Chlorobenzyl)-4-(5,6-tetramethylene-4-thieno [2,3-d]pyrimidinyl)-1-piperazinecarboxamide (Compound 19)

Yield: quantitative

Melting point: 185–186° C.

$^1$H-NMR (CDCl$_3$) δ (ppm): 8.42 (1H, s), 7.23 (4H, s), 6.72 (1H, brt, J=5.0 Hz), 4.86 (2H, d, J=5.0 Hz), 4.10–4.02 (4H, m), 3.49–3.45 (4H, m), 2.90–2.85 (4H, m), 1.93–1.92 (2H, m), 1.81–1.80 (2H, m).

FAB-Mass: 458 ((M+1)$^+$)

IR (KBr tablet method) ν (cm$^{-1}$): 1531, 1498, 1435, 1381, 1325, 1269, 1250, 1206, 984, 972.

In the following Examples 20 and 21, the target compounds were produced in the same manner as in Example 2, except that 4-(6-purinyl)-piperazinecarboxylic acid tert-butyl ester was replaced with 4-(4-pyrido[2,3-d] pyrimidinyl)-1-piperazinecarboxylic acid tert-butyl ester produced in Reference Example 8, and that 4-nitrophenyl isocyanate was replaced with a corresponding isocyanate or isothiocyanate.

EXAMPLE 20

N-(4-Phenoxyphenyl)-4-(4-pyrido[2,3-d]
pyrimidinyl)-1-piperazinecarboxamide (Compound
20)

Yield: 76%

Melting point: 104–106° C.

$^1$H-NMR (CDCl$_3$) δ (ppm): 9.06 (1H, dd, J=4.3 Hz, 1.3 Hz), 8.86 (1H, s), 8.26 (1H, dd, J=8.3 Hz, 1.3 Hz), 7.42 (1H, dd, J=8.3 Hz, 4.3 Hz), 7.37–7.13 (4H, m), 7.09–6.92 (6H, m), 3.96–3.92 (4H, m), 3.80–3.76 (4H, m).

FAB-Mass: 427 ((M+1)$^+$)

IR (KBr tablet method) ν (cm$^{-1}$): 1664, 1595, 1570, 1541, 1508, 1491, 1414, 1329, 1228, 993, 792, 756.

EXAMPLE 21

N-Benzyl-4-(4-pyrido[2,3-d]pyrimidinyl)-1-
piperazinethiocarboxamide (Compound 21)

Yield: 59%

Melting point: 169–170° C.

$^1$H-NMR (CDCl$_3$) δ (ppm): 9.03 (1H, dd, J=4.3 Hz, 1.7 Hz), 8.80 (1H, s), 8.27 (1H, dd, J=8.2 Hz, 1.7 Hz), 7.42–7.29 (6H, m), 6.04 (1H, brt, J=5.0 Hz), 4.90 (2H, d, J=5.0 Hz), 4.18–4.14 (4H, m), 4.08–4.06 (4H, m).

FAB-Mass: 365 ((M+1)$^+$)

IR (KBr tablet method) ν (cm$^{-1}$): 1568, 1541, 1498, 1444, 1338, 1273.

EXAMPLE 22

N-(4-Phenoxyphenyl)-4-(6-fluoro-4-pyrido[3,4-d]
pyrimidinyl)-1-piperazinecarboxamide (Compound
22)

The target compound was produced in the same manner as in Example 2, except that 4-(6-purinyl)-1-piperazinecarboxylic acid tert-butyl ester was replaced with 4-(6-fluoro-4-pyrido[3,4-d]pyrimidinyl)-1-piperazinecarboxylic acid tert-butyl ester produced in Reference Example 9, and 4-nitrophenyl isocyanate was replaced with 4-phenoxyphenyl isocyanate.

Yield: 86%

$^1$H-NMR (CDCl$_3$) δ (ppm): 9.05 (1H, s), 8.78 (1H, s), 7.35–7.27 (5H, m), 7.07 (1H, m), 7.01–6.96 (4H, m), 6.51 (1H, brs), 3.99–3.95 (4H, m), 3.79–3.75 (4H, m).

FAB-Mass: 445 ((M+1)$^+$)

EXAMPLE 23

N-(4-Phenoxyphenyl)-4-[3-amino-1-(2,6-
naphthyridinyl)]-1-piperazinecarboxamide
(Compound 23)

The target compound was produced in the same manner as in Example 1, except that 6-chloropurine was replaced with 3-amino-1-bromo-2,6-naphthyridine.

Yield: 8%

$^1$H-NMR (CDCl$_3$) δ (ppm): 8.95 (1H, s), 8.27 (1H, d, J=5.9 Hz), 7.58 (1H, d, J=5.9 Hz), 7.36–7.29 (4H, m), 7.07 (1H, m), 7.01–6.97 (4H, m), 6.40 (1H, s), 6.39 (1H, brs), 4.43 (2H, br), 3.76–3.72 (4H, m), 3.54–3.49 (4H, m).

FAB-Mass: 441 ((M+1)$^+$)

In the following Examples 24 to 27, the target compounds were produced in the same manner as in Example 2, except that 4-nitrophenyl isocyanate was replaced with a corresponding isocyanate or isothiocyanate.

EXAMPLE 24

N-(4-Cyanophenyl)-4-(6-purinyl)-1-
piperazinecarboxamide (Compound 24)

Yield: 64%

$^1$H-NMR (DMSO-d$_6$) δ (ppm): 9.11 (1H, brs), 8.25 (1H, s), 8.16 (1H, s), 7.69 (4H, s), 4.28 (4H, br), 3.63 (4H, m).

FAB-Mass: 349 ((M+1)$^+$)

EXAMPLE 25

N-(4-Isopropoxyphenyl)-4-(6-purinyl)-1-
piperazinecarboxamide (Compound 25)

Yield: 66%

$^1$H-NMR (DMSO-d$_6$) δ (ppm): 8.44 (1H, brs), 8.25 (1H, s), 8.16 (1H, s), 7.33 (2H, d, J=8.9 Hz), 6.81 (2H, d, J=8.9 Hz), 4.50 (1H, m), 4.26 (4H, m), 3.58 (4H, m), 1.24 (6H, d, J=5.9 Hz).

FAB-Mass: 382 ((M+1)$^+$)

EXAMPLE 26

N-(3,4-Methylenedioxybenzyl)-4-(6-purinyl)-1-
piperazinethiocarboxamide (Compound 26)

Yield: 96%

$^1$H-NMR (DMSO-d$_6$) δ (ppm): 8.24 (1H, s), 8.24 (1H, brt, J=5.3 Hz), 8.15 (1H, s), 6.91 (1H, s), 6.86–6.77 (2H, m), 5.97 (2H, s), 4.72 (2H, d, J=5.3 Hz), 4.26 (4H, m), 3.99 (4H, m).

FAB-Mass: 398 ((M+1)$^+$)

EXAMPLE 27

N-(4-Methoxybenzyl)-4-(6-purinyl)-1-
piperazinethiocarboxamide (Compound 27)

Yield: 55%

$^1$H-NMR (DMSO-d$_6$) δ (ppm): 13.06 (1H, br), 8.25 (1H, s), 8.25 (1H, br), 8.16 (1H, s), 7.26 (2H, d, J=8.3 Hz), 6.88 (2H, d, J=8.3 Hz), 4.76 (2H, d, J=5.3 Hz), 4.26 (4H, br), 3.99 (4H, br), 3.73 (3H, s).

FAB-Mass: 384 ((M+1)$^+$)

EXAMPLE 28

N-Benzyl-N'-cyano-4-(6,7-dimethoxy-4-
quinazolinyl)-1-piperazinecarboxamidine
(Compound 28)

The target compound was produced in the same manner as in Example 41 described later, except that piperonylamine was replaced with benzylamine.

Yield: 64%

$^1$H-NMR (CDCl$_3$) δ (ppm): 8.65 (1H, s), 7.39–7.19 (6H, m), 7.04 (1H, s), 5.76 (1H, brt, J=5.6 Hz), 4.59 (2H, d, J=5.6 Hz), 4.02 (3H, s), 3.97 (3H, s), 3.79–3.69 (8H, m).

FAB-Mass: 432 (M$^+$+1)

EXAMPLE 29

N-(2-Chlorobenzyl)-N'-cyano-4-(6,7-dimethoxy-4-
quinazolinyl)-1-piperazinecarboxamidine
(Compound 29)

To an ethanol solution (10 mL) of Compound 65 produced in Example 65 described later (0.60 g, 1.61 mmol), 2-chlorobenzylamine (0.97 mL, 8.04 mmol) was added, followed by heating under reflux for 10 hours. 2-Chlorobenzylamine (0.97 mL, 8.04 mmol) was further added thereto, followed by heating under reflux for 6.5 hours. The reaction solution was concentrated, and the resulting residue was purified by silica gel column chromatography to give the target compound (0.85 g, 1.83 mmol).

Yield: quantitative $^1$H-NMR (DMSO-$d_6$) δ (ppm): 8.65 (1H, s), 7.47–7.15 (5H, m), 7.04 (1H, s), 5.78 (1H, brt, J=5.6 Hz), 4.68 (2H, d, J=5.6 Hz), 4.02 (3H, s), 3.98 (3H, s), 3.77–3.70 (8H, m).

FAB-Mass: 468 ((M+3)$^+$), 466 ((M+1)$^+$)

EXAMPLE 30

N-(3-Chlorobenzyl)-N'-cyano-4-(6,7-dimethoxy-4-quinazolinyl)-1-piperazinecarboxamidine (Compound 30)

To an isopropanol solution (10 mL) of Compound 67 produced in Example 67 described later (0.50 g, 1.20 mmol), 3-chlorobenzylamine (0.44 mL, 3.60 mmol) was added, followed by heating under reflux for 6 hours. The reaction solution was concentrated and the resulting residue was purified by silica gel column chromatography to give the target compound (0.66 g, 1.42 mmol).

Yield: quantitative $^1$H-NMR (DMSO-$d_6$) δ (ppm): 8.56 (1H, s), 7.93 (1H, brt, J=4.6 Hz), 7.39–7.28 (4H, m), 7.24 (1H, s), 7.1.9 (1H, s), 4.52 (2H, d, J=4.6 Hz), 3.93 (3H, s), 3.93 (3H, s), 3.74 (8H, m).

FAB-Mass: 468 ((M+3)$^+$), 466 ((M+1)$^+$)

EXAMPLE 31

N-(4-Chlorobenzyl)-N'-cyano-4-(6,7-dimethoxy-4-quinazolinyl)-1-piperazinecarboxamidine (Compound 31)

To an ethanol solution (10 mL) of Compound 67 produced in Example 67 described later (438 mg, 1.05 mmol), 4-chlorobenzylamine (0.64 mL, 5.26 mmol) was added, followed by heating under reflux for 7.5 hours. The reaction solution was concentrated and the resulting residue was purified by silica gel column chromatography to give the target compound (0.58 g, 1.25 mmol).

Yield: quantitative $^1$H-NMR (CDCl$_3$) δ (ppm): 8.65 (1H, s), 7.35–7.18 (5H, m), 7.05 (1H, s), 5.49 (1H, brt, J=5.6 Hz), 4.57 (2H, d, J=5.6 Hz), 4.02 (3H, s), 3.98 (3H, s), 3.78–3.71 (8H, m).

FAB-Mass: 468 ((M+3)$^+$), 466 ((M+1)$^+$)

EXAMPLE 32

N'-Cyano-4-(6,7-dimethoxy-4-quinazolinyl)-N-(4-fluorobenzyl)-1-piperazinecarboxamidine (Compound 32)

The target compound was produced in the same manner as in Example 30, except that 3-chlorobenzylamine was replaced with 4-fluorobenzylamine.

Yield: 80%

$^1$H-NMR (DMSO-$d_6$) δ (ppm): 8.56 (1H, s), 7.93 (1H, brs), 7.40–7.34 (2H, m), 7.24 (1H, s), 7.22–7.14 (3H, m), 4.50 (2H, br), 3.93 (3H, s), 3.93 (3H, s), 3.72 (8H, m).

FAB-Mass: 450 ((M+1)$^+$)

EXAMPLE 33

N-(4-Bromobenzyl)-N'-cyano-4-(6,7-dimethoxy-4-quinazolinyl)-1-piperazinecarboxamidine (Compound 33)

The target compound was produced in the same manner as in Example 30, except that 3-chlorobenzylamine was replaced with 4-bromobenzylamine hydrochloride, and that the reaction was carried out after producing a free form of the hydrochloride in the system using triethylamine.

Yield: 68%

$^1$H-NMR (DMSO-$d_6$) δ (ppm): 8.56 (1H, s), 7.95 (1H, brt, J=5.3 Hz), 7.55 (2H, d, J=8.3 Hz), 7.29 (2H, d, J=8.3 Hz), 7.24 (1H, s), 7.19 (1H, s), 4.49 (2H, d, J=5.3 Hz), 3.93 (3H, s), 3.93 (3H, s), 3.73 (8H, m).

FAB-Mass: 512 ((M+3)$^+$), 510 ((M+1)$^+$)

In the following Examples 34 to 37, the target compounds were produced in the same manner as in Example 30, except that 3-chlorobenzylamine was replaced with a corresponding amine.

EXAMPLE 34

N'-Cyano-4-(6,7-dimethoxy-4-quinazolinyl)-N-(4-methylbenzyl)-1-piperazinecarboxamidine (Compound 34)

Yield: 81%

$^1$H-NMR (DMSO-$d_6$) δ (ppm): 8.56 (1H, s), 7.90 (1H, brs), 7.23–7.14 (6H, m), 4.49 (2H, s), 3.93 (3H, s), 3.93 (3H, s), 3.72 (8H, br), 2.29 (3H, s).

FAB-Mass: 446 ((M+1)$^+$)

EXAMPLE 35

N'-Cyano-4-(6,7-dimethoxy-4-quinazolinyl)-N-(4-isopropylbenzyl)-1-piperazinecarboxamidine (Compound 35)

Yield: 69%

$^1$H-NMR (CDCl$_3$) δ (ppm): 8.66 (1H, s), 7.26 (4H, s), 7.26 (1H, s), 7.05 (1H, s), 5.10 (1H, brt, J=5.3 Hz), 4.58 (2H, d, J=5.3 Hz), 4.02 (3H, s), 3.99 (3H, s), 3.79–3.70 (8H, m), 2.91 (1H, m), 1.24 (6H, d, J=6.9 Hz).

FAB-Mass: 474 ((M+1)$^+$)

EXAMPLE 36

N'-Cyano-4-(6,7-dimethoxy-4-quinazolinyl)-N-(4-methoxybenzyl)-1-piperazinecarboxamidine (Compound 36)

Yield: 91%

$^1$H-NMR (CDCl$_3$) δ (ppm): 8.63 (1H, s), 7.25 (2H, d, J=8.6 Hz), 7.23 (1H, s), 7.04 (1H, s), 6.85 (2H, d, J=8.6 Hz), 5.94 (1H, brt, J=5.6 Hz), 4.53 (2H, d, J=5.6 Hz), 4.01 (3H, s), 3.97 (3H, s), 3.76 (3H, s), 3.72 (8H, m).

FAB-Mass: 462 ((M+1)$^+$)

EXAMPLE 37

N'-Cyano-4-(6,7-dimethoxy-4-quinazolinyl)-N-(4-methylthiobenzyl)-1-piperazinecarboxamidine (Compound 37)

Yield: 87%

$^1$H-NMR (DMSO-$d_6$) δ (ppm): 8.56 (1H, s), 7.91 (1H, brs), 7.26–7.24 (5H, m), 7.19 (1H, s), 4.48 (2H, s), 3.93 (3H, s), 3.93 (3H, s), 3.72 (8H, br), 2.46 (3H, s).

FAB-Mass: 478 ((M+1)$^+$)

EXAMPLE 38

N'-Cyano-4-(6,7-dimethoxy-4-quinazolinyl)-N-(4-mesylbenzyl)-1-piperazinecarboxamidine (Compound 38)

The target compound was produced in the same manner as in Example 30, except that 3-chlorobenzylamine was replaced with 4-mesylbenzylamine hydrochloride, and that the reaction was carried out after producing a free form of the hydrochloride in the system using triethylamine.

Yield: 67%

$^1$H-NMR (DMSO-$d_6$) δ (ppm): 8.57 (1H, s), 8.04 (1H, brt, J=5.3 Hz), 7.91 (2H, d, J=8.6 Hz), 7.58 (2H, d, J=8.6 Hz), 7.24 (1H, s), 7.20 (1H, s), 4.61 (2H, d, J=5.3 Hz), 3.94 (3H, s), 3.93 (3H, s), 3.76 (8H, m), 3.21 (3H, s).

FAB-Mass: 510 ((M+1)$^+$)

EXAMPLE 39

N-(1-Butyl)-N'-cyano-4-(6,7-dimethoxy-4-quinazolinyl)-1-piperazinecarboxamidine (Compound 39)

The target compound was produced in the same manner as in Example 30, except that 3-chlorobenzylamine was replaced with 1-butylamine.

Yield: 91%

$^1$H-NMR (CDCl$_3$) δ (ppm): 8.67 (1H, s), 7.28 (1H, s), 7.07 (1H, s), 5.21 (1H, brt, J=5.6 Hz), 4.03 (3H, s), 3.99 (3H, s), 3.79–3.70 (8H, m), 3.45 (2H, dt, J=7.3 Hz, 5.6 Hz), 1.61 (2H, tt, J=7.3 Hz, 7.3 Hz), 1.40 (2H, tq, J=7.6 Hz, 7.3 Hz), 0.95 (3H, t, J=7.6 Hz).

FAB-Mass: 398 ((M+1)$^+$)

EXAMPLE 40

N'-Cyano-N-cyclohexyl-4-(6,7-dimethoxy-4-quinazolinyl)-1-piperazinecarboxamidine (Compound 40)

The target compound was produced in the same manner as in Example 30, except that 3-chlorobenzylamine was replaced with cyclohexylamine.

Yield: 75%

$^1$H-NMR (CDCl$_3$) δ (ppm): 8.67 (1H, s), 7.26 (1H, s), 7.07 (1H, s), 4.90 (1H, d, J=8.3 Hz), 4.03 (3H, s), 3.99 (3H, s), 3.80–3.70 (9H, m), 2.04–1.17 (10H, m).

FAB-Mass: 424 ((M+1)$^+$)

EXAMPLE 41

N'-Cyano-4-(6,7-dimethoxy-4-quinazolinyl)-N-(3,4-methylenedioxybenzyl)-1-piperazinecarboxamidine (Compound 41)

To a dimethylformamide solution (20 mL) of Compound 65 produced in Example 65 described later (1.63 g, 4.38 mmol), piperonylamine (2.98 mL, 23.9 mmol) was added, followed by stirring under heating at 80° C. for 13 hours. Piperonylamine (2.98 mL, 23.9 mmol) was further added thereto, followed by stirring at the same temperature for 3.5 hours. After the reaction solution was allowed to stand for cooling, the reaction solution was poured into water, sodium chloride was added thereto, and the precipitated crystals were recovered by filtration, washed with water, dried, and then purified by silica gel column chromatography to give the target compound (0.53 g, 1.12 mmol).

Yield: 25%

$^1$H-NMR (CDCl$_3$) δ (ppm): 8.66 (1H, s), 7.25 (1H, s), 7.06 (1H, s), 6.82–6.72 (3H, m), 5.96 (2H, s), 5.26 (1H, brt, J=5.0 Hz), 4.51 (2H, d, J=5.0 Hz), 4.02 (3H, s), 3.98 (3H, s), 3.78–3.70 (8H, m).

FAB-Mass: 476(M$^+$+1)

EXAMPLE 42

N'-Cyano-4-(6,7-dimethoxy-4-quinazolinyl)-N-[2-(3,4-methylenedioxyphenyl)ethyl]-1-piperazinecarboxamidine (Compound 42)

The target compound was produced in the same manner as in Example 30, except that 3-chlorobenzylamine was replaced with 2-(3,4-methylenedioxyphenyl)ethylamine hydrochloride, and that the reaction was carried out after producing a free form of the hydrochloride in the system using triethylamine.

Yield: 68%

$^1$H-NMR (DMSO-$d_6$) δ (ppm): 8.56 (1H, s), 7.41 (1H, br), 7.24 (1H, s), 7.18 (1H, s), 6.85 (1H, s), 6.84 (1H, d, J=7.9 Hz), 6.70 (1H, d, J=7.9 Hz), 5.97 (2H, s), 3.94 (3H, s), 3.93 (3H, s), 3.66–3.64 (8H, m), 3.54 (2H, m), 2.77 (2H, t, J=6.9 Hz).

FAB-Mass: 490 ((M+1)$^+$)

In the following Examples 43 to 49, the target compounds were produced in the same manner as in Example 30, except that 3-chlorobenzylamine was replaced with a corresponding amine.

EXAMPLE 43

N'-Cyano-4-(6,7-dimethoxy-4-quinazolinyl)-N-(2-pyridylmethyl)-1-piperazinecarboxamidine (Compound 43)

Yield: 86%

$^1$H-NMR (CDCl$_3$) δ (ppm): 8.67 (1H, s), 8.54 (1H, dd, J=5.0 Hz, 1.7 Hz), 7.73 (1H, ddd, J=7.9 Hz, 7.6 Hz, 1.7 Hz), 7.35–7.24 (3H, m), 7.10 (1H, s), 7.06 (1H, brt, J=4.3 Hz), 4.85 (2H, d, J=4.3 Hz), 4.03 (3H, s), 4.00 (3H, s), 3.83 (8H, m).

FAB-Mass: 433 ((M+1)$^+$)

EXAMPLE 44

N'-Cyano-4-(6,7-dimethoxy-4-quinazolinyl)-N-(3-pyridylmethyl)-1-piperazinecarboxamidine (Compound 44)

Yield: 75%

$^1$H-NMR (CDCl$_3$) δ (ppm): 8.61 (1H, s), 8.52 (1H, d, J=2.0 Hz), 8.43 (1H, dd, J=5.0 Hz, 1.7 Hz), 7.70 (1H, ddd, J=7.9 Hz, 2.0 Hz, 1.7 Hz), 7.26–7.22 (3H,m), 7.21 (1H,s), 7.05 (1H,s), 4.58 (2H, d, J=5.6 Hz), 4.00 (3H, s), 3.96 (3H, s), 3.75 (8H, m).

FAB-Mass: 433 ((M+1)$^+$)

EXAMPLE 45

N'-Cyano-4-(6,7-dimethoxy-4-quinazolinyl)-N-(4-pyridylmethyl)-1-piperazinecarboxamidine (Compound 45)

Yield: quantitative $^1$H-NMR (DMSO-$d_6$) δ (ppm): 8.57 (1H, s), 8.53 (2H, d, J=5.9 Hz), 7.98 (1H, brt, J=4.6 Hz), 7.31 (2H, d, J=5.9 Hz), 7.24 (1H, s), 7.20 (1H, s), 4.54 (2H, d, J=4.6 Hz), 3.94 (3H, s), 3.94 (3H, s), 3.77 (8H, m).

FAB-Mass: 433 ((M+1)$^+$)

EXAMPLE 46

N'-Cyano-4-(6,7-dimethoxy-4-quinazolinyl)-N-[2-(3-pyridyl)-ethyl]-1-piperazinecarboxamidine (Compound 46)

Yield: 81%

$^1$H-NMR (CDCl$_3$) δ (ppm): 8.64 (1H, s), 8.47–8.45 (2H, m), 7.62 (1H, ddd, J=7.9 Hz, 2.0 Hz, 1.7 Hz), 7.27 (1H, dd, J=7.9 Hz, 5.0 Hz), 7.24 (1H, s), 7.05 (1H, s), 5.84 (1H, brt, J=5.6 Hz), 4.02 (3H, s), 3.98 (3H, s), 3.78–3.65 (10H, m), 2.98 (2H, t, J=6.9 Hz).

FAB-Mass: 447 ((M+1)$^+$)

EXAMPLE 47

N'-Cyano-4-(6,7-dimethoxy-4-quinazolinyl)-N-[2-(4-pyridyl)-ethyl]-1-piperazinecarboxamidine (Compound 47)

Yield: 64%

$^1$H-NMR (CDCl$_3$) δ (ppm): 8.60 (1H, s), 8.44 (2H, d, J=4.3 Hz), 7.22 (1H, s), 7.18 (2H, d, J=4.3 Hz), 7.04 (1H, s), 6.61 (1H, br), 4.01 (3H, s), 3.97 (3H, s), 3.74–3.67 (10H, m), 2.96 (2H, t, J=6.9 Hz).

FAB-Mass: 447 ((M+1)$^+$)

EXAMPLE 48

N'-Cyano-4-(6,7-dimethoxy-4-quinazolinyl)-N-(5-methyl-2-pyrazinyl)-1-piperazinecarboxamidine 1-piperazinecarboxamidine (Compound 48)

Yield: quantitative $^1$H-NMR (CDCl$_3$) δ (ppm): 8.66 (1H, s), 8.54 (1H, s), 8.39 (1H, s), 7.26 (1H, s), 7.08 (1H, s), 6.69 (1H, brt, J=4.0 Hz), 4.81 (2H, d, J=4.0 Hz), 4.03 (3H, s), 4.00 (3H, s), 3.82 (8H, m), 2.58 (3H, s).

FAB-Mass: 448 ((M+1)$^+$)

EXAMPLE 49

N'-Cyano-4-(6,7-dimethoxy-4-quinazolinyl)-N-furfuryl-1-piperazinecarboxamidine (Compound 49)

Yield: 59%

$^1$H-NMR (CDCl$_3$) δ (ppm): 8.64 (1H, s), 7.35 (1H, m), 7.24 (1H, s), 7.05 (1H, s), 6.31–6.12 (3H, m), 4.61 (2H, d, J=5.6 Hz), 4.01 (3H, s), 3.98 (3H, s), 3.75 (8H, m).

FAB-Mass: 422 ((M+1)$^+$)

EXAMPLE 50

4-{4-[1-(2-Chlorobenzylamino)-2,2-dicyanovinyl]-1-piperazinyl}-6,7-dimethoxyquinazoline (Compound 50)

To an acetonitrile solution (10 mL) of Compound 64 produced in Example 64 described later (0.50 g, 1.26 mmol), 2-chlorobenzylamine (0.76 mL, 6.30 mmol) was added, followed by heating under reflux for 5.5 hours. After the reaction solution was allowed to stand for cooling, the precipitated crystals were recovered by filtration, washed with acetonitrile, and then dried to give the target compound (0.81 g, 1.66 mmol).

Yield: quantitative $^1$H-NMR (DMSO-d$_6$) δ (ppm): 8.82 (1H, s), 8.14 (1H, brt, J=5.0 Hz), 7.54–7.49 (2H, m), 7.44 (1H, s), 7.41–7.37 (3H, m), 4.59 (2H, d, J=5.0 Hz), 4.26 (4H, m), 3.98 (3H, s), 3.96 (3H, s), 3.78 (4H, m).

FAB-Mass: 492 ((M+3)$^+$), 490 ((M+1)$^+$)

In the following Examples 51 to 57, the target compounds were produced in the same manner as in Example 50, except that 2-chlorobenzylamine was replaced with a corresponding amine.

EXAMPLE 51

4-{4-[1-(3-Chlorobenzylamino)-2,2-dicyanovinyl]-1-piperazinyl}-6,7-dimethoxyquinazoline (Compound 51)

Yield: 45%

$^1$H-NMR (DMSO-d$_6$) δ (ppm): 8.58 (1H, s), 8.09 (1H, brt, J=5.0 Hz), 7.48–7.33 (4H, m), 7.24 (1H, s), 7.20 (1H, s), 4.52 (2H, d, J=5.0 Hz), 3.94 (3H, s), 3.94 (3H, s), 3.75–3.70 (8H, m).

FAB-Mass: 492 ((M+3)$^+$), 490 ((M+1)$^+$)

EXAMPLE 52

4-{4-[1-(4-Chlorobenzylamino)-2,2-dicyanovinyl]-1-piperazinyl}-6,7-dimethoxyquinazoline (Compound 52)

Yield: 62%

$^1$H-NMR (CDCl$_3$) δ (ppm): 8.66 (1H, s), 7.38 (2H, d, J=8.6 Hz), 7.27 (1H, s), 7.25 (2H, d, J=8.6 Hz), 7.04 (1H, s), 5.46 (1H, brt, J=5.6 Hz), 4.44 (2H, d, J=5.6 Hz), 4.03 (3H, s), 3.99 (3H, s), 3.82–3.78 (4H, m), 3.66–3.64 (4H, m).

FAB-Mass: 492 ((M+3)$^+$), 490 ((M+1)$^+$)

EXAMPLE 53

4-{4-[2,2-Dicyano-1-(4-methoxybenzylamino)vinyl]-1-piperazinyl}-6,7-dimethoxyquinazoline (Compound 53)

Yield: 48%

$^1$H-NMR (DMSO-d$_6$) δ (ppm): 8.57 (1H, s), 8.02 (1H, brs), 7.31 (2H, d, J=8.6 Hz), 7.24 (1H, s), 7.19 (1H, s), 6.95 (2H, d, J=8.6 Hz), 4.43 (2H, s), 3.93 (3H, s), 3.93 (3H, s), 3.76–3.68 (8H, m), 3.33 (3H, s).

FAB-Mass: 486 ((M+1)$^+$)

EXAMPLE 54

4-{4-[2,2-Dicyano-1-(3,4-methylenedioxybenzylamino)vinyl]-1-piperazinyl}-6,7-dimethoxyquinazoline (Compound 54)

Yield: 48%

$^1$H-NMR (DMSO-d$_6$) δ (ppm): 8.57 (1H, s), 7.99 (1H, brs), 7.24 (1H, s), 7.19 (1H, s), 6.97 (1H, s), 6.93–6.87 (2H, m), 6.02 (2H, s), 4.40 (2H, s), 3.93 (3H, s), 3.93 (3H, s), 3.72–3.68 (8H, m).

FAB-Mass: 500 ((M+1)$^+$)

EXAMPLE 55

4-{4-[2,2-Dicyano-1-(2-pyridylmethylamino)vinyl]-1-piperazinyl}-6,7-dimethoxyquinazoline (Compound 55)

Yield: 60%

$^1$H-NMR (DMSO-d$_6$) δ (ppm): 8.60 (1H, s), 8.57 (1H, dd, J=5.0 Hz, 2.0 Hz), 8.07 (1H, brt, J=5.3 Hz), 7.83 (1H, ddd, J=7.9 Hz, 7.6 Hz, 2.0 Hz), 7.45 (1H, d, J=7.9 Hz), 7.33 (1H, dd, J=7.6 Hz, 5.0 Hz), 7.25 (1H, s), 7.23 (1H, s), 4.64 (2H, d, J=5.3 Hz), 3.94 (3H, s), 3.94 (3H, s), 3.80–3.78 (8H, m).

FAB-Mass: 457 ((M+1)$^+$)

EXAMPLE 56

4-{4-[2,2-Dicyano-1-(3-pyridylmethylamino)vinyl]-1-piperazinyl}-6,7-dimethoxyquinazoline (Compound 56)

Yield: 77%

$^1$H-NMR (DMSO-d$_6$) δ (ppm): 8.61 (1H, s), 8.60 (1H, s), 8.53 (1H, dd, J=5.0 Hz, 1.7 Hz), 8.10 (1H, brt, J=4.9 Hz), 7.82 (1H, dd, J=7.9 Hz, 1.7 Hz), 7.42 (1H, dd, J=7.9 Hz,. 5.0 Hz), 7.24 (1H, s), 7.22 (1H, s), 4.55 (2H, d, J=4.9 Hz), 3.94 (3H, s), 3.93 (3H, s), 3.80 (4H, m), 3.71 (4H, m).

FAB-Mass: 457 ((M+1)$^+$)

EXAMPLE 57

4-{4-[2,2-Dicyano-1-(4-pyridylmethylamino)vinyl]-1-piperazinyl}-6,7-dimethoxyquinazoline (Compound 57)

Yield: 72%

$^1$H-NMR (DMSO-d$_6$) δ (ppm): 8.67 (1H, s), 8.58 (2H, d, J=4.6 Hz), 8.22 (1H, brt, J=5.6 Hz), 7.42 (2H, d, J=4.6 Hz), 7.30 (1H, s), 7.28 (1H, s), 4.59 (2H, d, J=5.6 Hz), 4.02–3.95 (10H, m), 3.75 (4H, m).

FAB-Mass: 457 ((M+1)$^+$)

EXAMPLE 58

6,7-Dimethoxy-4-[4-(1-methylthio-2-nitrovinyl)-1-piperazinyl]quinazoline (Compound 58)

To an ethanol solution (30 mL) of 6,7-dimethoxy-4-(1-piperazinyl)quinazoline described in South African Patent 67 06512 (1968) (Compound (i); 6.00 g, 21.9 mmol), commercially available 1,1-bis(methylthio)-2-nitroethylene (4.27 g, 25.8 mol) was added, followed by stirring under heating at 50 C for 9 hours and then heating under reflux for 2.5 hours. After the reaction solution was allowed to stand for cooling, the solvent was evaporated and then the resulting residue was purified by silica gel column chromatography to give the target compound (2.65 g, 6.78 mmol).

Yield: 31%

$^1$H-NMR (CDCl$_3$) δ (ppm): 8.61 (1H, s), 7.20 (1H, s), 7.02 (1H, s), 6.64 (1H, s), 3.96 (3H, s), 3.93 (3H, s), 3.74 (8H, m), 2.42 (3H, s), FAB-Mass: 392 ((M+1)$^+$)

EXAMPLE 59

6,7-Dimethoxy-4-{4-[2-nitro-1-(4-pyridylmethylamino)vinyl]-1-piperazinyl}quinazoline (Compound 59)

To a pyridine solution (10 mL) of Compound 58 produced in Example 58 (730 mg, 1.87 mmol), 4-aminomethylpyridine (0.57 mL, 5.61 mmol) was added, followed by stirring in argon atmosphere under heating at 80° C. for 5 hours. After the reaction solution was allowed to stand for cooling, the solvent was evaporated, and the resulting residue was purified by silica gel column chromatography to give the target compound (130 mg, 0.29 mmol).

Yield: 15%

$^1$H-NMR (DMSO-d$_6$) δ (ppm): 9.01 (1H, br), 8.57 (2H, d, J=5.9 Hz), 8.57 (1H, s), 7.36 (2H, d, J=5.9 Hz), 7.24 (1H, s), 7.18 (1H, s), 6.40 (1H, br), 4.56 (2H, d, J=5.3 Hz), 3.94 (3H, s), 3.93 (3H, s), 3.76 (4H, m), 3.54 (4H, m).

FAB-Mass: 452 ((M+1)$^+$)

EXAMPLE 60

6,7-Dimethoxy-4-{4-[1-(3,4-methylenedioxybenzylamino)-2-nitrovinyl]-1-piperazinyl}quinazoline (Compound 60)

The target compound was produced in the same manner as in Example 59, except that 4-aminomethylpyridine was replaced with 3,4-methylenedioxybenzylamine.

Yield: 8%

$^1$H-NMR (CDCl$_3$) δ (ppm): 9.79 (1H, br), 8.71 (1H, s), 7.29 (1H, s), 7.06 (1H, s), 6.82–6.73 (3H, m), 6.56 (1H, s), 5.98 (2H, s), 4.46 (2H, d, J=5.6 Hz), 4.04 (3H, s), 4.00 (3H, s), 3.75–3.71 (4H, m), 3.44–3.41 (4H, m).

FAB-Mass: 495 ((M+1)$^+$)

EXAMPLE 61

N,N'-Dicyclohexyl-4-(6,7-dimethoxy-4-quinazolinyl)-1-piperazinecarboxamidine (Compound 61)

To an acetonitrile solution (10 mL) of Compound (i) (500 mg, 1.82 mmol), N,N'-Dicyclohexylcarbodiimide (DCC) (376 mg, 1.82 mmol) was added, followed by stirring at room temperature overnight. DCC (376 mg, 1.82 mmol) was further added thereto, followed by heating under reflux for 3 days, and then chloroform (10 mL) was added thereto, followed by further heating under reflux for 3 days. DCC (376 mg, 1.82 mmol) was further added thereto, followed by refluxing for 2 days, and then the residue obtained by evaporating the solvent was purified by silica gel column chromatography and further purified by preparative thin layer chromatography to give the target compound (73 mg, 0.15 mmol).

Yield: 8%

$^1$H-NMR (DMSO-d$_6$) δ (ppm): 8.62 (1H, s), 7.65 (1H, br), 7.28 (1H, s), 7.21 (1H, s), 3.94 (3H, s), 3.94 (3H, s), 3.81 (4H, br), 3.62 (4H, br), 3.32 (2H, m), 1.87–1.72 (8H, m), 1.62–1.57.(2H, m), 1.43–1.07 (10H, m).

FAB-Mass: 481 ((M+1)$^+$)

EXAMPLE 62

4-(6,7-Dimethoxy-4-quinazolinyl)-N-tosyl-1-piperazinecarboximidic thioacid methyl ester (Compound 62)

To an isopropanol solution (20 mL) of Compound (i) (1.00 g, 3.65 mmol), commercially available N-[bis(methylthio)methylene]-p-toluenesulfonamide (1.10 g, 3.99 mmol) was added, followed by heating under reflux for 2 days. After the reaction solution was allowed to stand for cooling, the precipitated crystals were recovered by filtration and washed with isopropanol to give the target compound (1.06 g, 2.12 mmol).

Yield: 58%

$^1$H-NMR (CDCl$_3$) δ (ppm): 8.68 (1H, s), 7.83 (2H, d, J=8.2 Hz), 7.27 (1H, s), 7.27 (2H, d, J=8.2 Hz), 7.06 (1H, s), 4.03 (3H, s), 4.03–4.01 (4H, m), 3.99 (3H, s), 3.82–3.78 (4H, m) , 2.43 (3H, s) , 2.41 (3H, s).

FAB-Mass: 502 ((M+1)$^+$)

EXAMPLE 63

4-(6,7-Dimethoxy-4-quinazolinyl)-N'-(3,4-methylenedioxybenzyl)-N-tosyl-1-piperazinecarboxamidine (Compound 63)

To a pyridine solution (5 mL) of Compound 62 produced in Example 62 (599 mg, 1.20 mmol), piperonylamine (0.74 mL, 5.94 mmol) was added, followed by heating under reflux in argon atmosphere for 5 hours. After the reaction solution was allowed to stand for cooling, water and sodium chloride were added thereto, and the thus precipitated crystals were recovered by filtration, washed with water, dried and then purified by silica gel column chromatography to give the target compound (248 mg, 0.41 mmol).

Yield: 34%

$^1$H-NMR (CDCl$_3$) δ (ppm): 8.66 (1H, s), 7.66 (2H, d, J=8.3 Hz), 7.28–7.26 (2H, m), 7.21 (2H, d, J=8.3 Hz), 7.06 (1H, s), 6.76–6.60 (3H, m), 5.98 (2H, s), 4.23 (2H, d, J=5.3 Hz), 4.03 (3H, s), 3.99 (3H, s), 3.72–3.71 (4H, m), 3.61–3.60 (4H, m), 2.40 (3H, s).

FAB-Mass: 605 ((M+1)$^+$)

EXAMPLE 64

4-[4-(2,2-Dicyano-1-methylthiovinyl)-1-piperazinyl]-6,7-dimethoxyquinazoline (Compound 64)

Commercially available [bis(methylthio)methylene]-propanedinitrile (3.40 g, 20.0 mmol) was added to an acetonitrile solution (50 mL) of Compound (i) (5.00 g, 18.2 mmol), and the mixture was heated under reflux for 4.5 hours. After there action solution was allowed to stand for cooling, the precipitated crystals were recovered by filtration, washed with acetonitrile, and dried to give the target compound (6.17 g, 15.6 mmol).

Yield: 85%

$^1$H-NMR (CDCl$_3$) 67 (ppm): 8.71 (1H, s), 7.29 (1H, s), 7.06 (1H, s), 4.06–3.94 (4H, m), 4.04 (3H, s), 4.01 (3H, s), 3.87–3.83 (4H, m), 2.65 (3H, s).

FAB-Mass: 397 ((M+1)$^+$)

EXAMPLE 65

N-Cyano-4-(6,7-dimethoxy-4-quinazolinyl)-1-piperazinecarboximidic thioacid methyl ester (Compound 65)

To an ethanol solution (30 mL) of Compound (i) (5.00 g, 18.2 mmol), commercially available S,S'-dimethyl-N-cyanodithioimide carbonate (3.26 g, purity 90%, 20.1 mmol) was added, followed by heating under reflux for 14.5 hours. After the reaction solution was allowed to stand for cooling, the precipitated crystals were recovered by filtration, washed with ethanol, and then dried to give the target compound (5.69 g, 15.3 mmol).

Yield: 84%

$^1$H-NMR (CDCl$_3$) δ (ppm): 8.70 (1H, s), 7.28 (1H, s), 7.06 (1H, s), 4.09–4.05 (4H, m), 4.04 (3H, s), 4.00 (3H, s), 3.78–3.75 (4H, m), 2.83 (3H, s).

FAB-Mass: 373 ((M+1)$^+$)

EXAMPLE 66

N-Cyano-4-(6,7-dimethoxy-4-quinazolinyl)-1-piperazinecarboximidic acid ethyl ester (Compound 66)

The target compound (66.7 mg, 0.18 mmol) was produced together with Compound 31 under the reaction conditions of Example 31.

Yield: 17%

$^1$H-NMR (CDCl$_3$) δ (ppm): 8.70 (1H, s), 7.28 (1H, s), 7.06 (1H, s), 4.50 (2H, q, J=7.3 Hz), 4.04 (3H, s), 4.00 (3H, s), 3.95–3.92 (4H, m), 3.75–3.71 (4H, m), 1.38 (3H, t, J=7.3 Hz).

FAB-Mass: 371 ((M+1)$^+$)

EXAMPLE 67

N-Cyano-4-(6,7-dimethoxy-4-quinazolinyl)-1-piperazinecarboximidic acid phenyl ester (Compound 67)

To an isopropanol solution (25 mL) of Compound (i) (1.00 g, 3.65 mmol), commercially available cyanocarbonimic acid phenyl ester (0.96 g, 4.03 mmol) was added, followed by heating under reflux for 12 hours. After the reaction solution was allowed to stand for cooling, the precipitated crystals were recovered by filtration and washed with isopropanol to give the target compound (0.70 g, 1.67 mmol).

Yield: 46%

$^1$H-NMR (CDCl$_3$) δ (ppm): 8.72 (1H, s), 7.46–7.40 (2H, m), 7.31–7.25 (2H, m), 7.13 (2H, d, J=8.6 Hz), 7.07 (1H, s), 4.04 (3H, s), 4.00 (3H, s), 3.96 (4H, m), 3.79–3.76 (4H, m).

FAB-Mass: 419 ((M+1)$^+$)

EXAMPLE 68

N'-Cyano-N-(3,4-dimethoxyphenyl)-4-(6,7-dimethoxy-4-quinazolinyl)-1-piperazinecarboxamidine (Compound 68)

To an acetonitrile solution (15 mL) of N-(3,4-dimethoxyphenyl)-4-(6,7-dimethoxy-4-quinazolinyl)-1-piperazinethiocarboxamide (499 mg, 1.07 mmol) described in WO 98/14431, DCC (4397 mg, 2.13 mmol), N,N-diisopropylethylamine (Hünig base) (0.19 mL, 1.09 mmol) and cyanamide (224 mg, 5.32 mmol) were added, followed by heating under reflux in argon atmosphere for 2 days. DCC (439 mg, 2.13 mmol), Hünig base (0.19 mL, 1.09 mmol) and cyanamide (224 mg, 5.32 mmol) were further added thereto, followed by heating under reflux for 2 days. After the reaction solution was concentrated, the resulting residue was purified by silica gel column chromatography to give the target compound (167 mg, 0.35 mmol).

Yield: 33%

$^1$H-NMR (CDCl$_3$) δ (ppm): 8.66 (1H, s), 7.40 (1H, brs), 7.26 (1H, s), 7.02 (1H, s), 6.83 (1H, d, J=9.2 Hz), 6.68–6.64 (2H, m), 4.02 (3H, s), 3.97 (3H, s), 3.87 (3H, s), 3.87 (3H, s), 3.64–3.58 (8H, m).

FAB-Mass: 478 ((M+1)$^+$)

EXAMPLE 69

N-(4-Phenoxyphenyl)-4-(4-pyrazolo[3,4-d]pyrimidinyl)-1-piperazinecarboxamide (Compound 69)

The target compound was produced in the same manner as in Example 2, except that 4-(6-purinyl)-1-piperazinecarboxylic acid tert-butyl ester was replaced with 4-(4-pyrazolo[3,4-d]pyrimidinyl )-1-piperazinecarboxylic acid tert-butyl ester produced in Reference Example 10, and that 4-nitrophenyl isocyanate was replaced with 4-phenoxyphenyl isocyanate.

Yield: 48%

$^1$H-NMR (CDCl$_3$) δ (ppm): 8.43 (1H, s), 8.04 (1H, s), 7.36–7.29 (4H, m), 7.09 (1H, m), 7.01–6.97 (4H, m), 6.32 (1H, brs), 4.20–4.16 (4H, m), 3.82–3.80 (4H, m).

FAB-Mass: 41.6 ((M+1)$^+$)

EXAMPLE 70

N-(4-Phenoxyphenyl)-4-( 6-hydroxy-4-imidazo[4,5-d]-pyrimidinyl)-1-piperazinecarboxamide (Compound 70)

The target compound was produced in the same manner as in Example 2, except that 4-(6-purinyl)-1- piperazinecarboxylic acid tert-butyl ester was replaced with 4-(6-hydroxy-4-imidazo[4,5-d]pyrimidinyl)-1-piperazinecarboxylic acid tert-butyl ester produced in Reference Example 11, and that 4-nitrophenyl isocyanate was replaced with 4-phenoxyphenyl isocyanate.

Yield: 52%

$^1$H-NMR (DMSO-d$_6$) δ (ppm): 11.50 (1H, br), 10.85 (1H, br), 8.64(1H, brs), 8.13 (1H, s), 7.49 (2H, d, J=8.9 Hz), 7.39–7.33 (2H, m), 7.08 (1H, m), 6..96–6.93 (4H, m), 3.57 (8H, m).

FAB-Mass: 432 ((M+1)$^+$)

Reference Example 1

4-[N-(4-Phenoxyphenyl)carbamoyl]-1-piperazinecarboxylic acid tert-butyl ester

To a methylene chloride solution (25 mL) of N-tert-butoxycarbonylpiperazine (2.50 g, 13.4 mmol), 4-phenoxyphenyl isocyanate (2.83 mL, 13.4 mmol) was added, followed by stirring at room temperature overnight. Methanol was added to the reaction solution, and the solvent was evaporated to give the target compound (5.71 g, 14.4 mmol).

Yield: quantitative $^1$H-NMR (CDCl$_3$) δ (ppm): 7.35–7.26 (4H, m), 7.07 (1H, m), 6.99–6.95 (4H, m), 6.35 (1H, brs), 3.49 (8H, m), 1.48 (9H, s).

FAB-Mass: 398 ((M+1)$^+$)

Reference Example 2

4-(2-Amino-6-purinyl)-1-piperazinecarboxylic acid tert-butyl ester

To a dimethylformamide suspension (20 mL) of commercially available 2-amino-6-chloropurine (3.00 g, 17.7 mmol), triethylamine (12.3 mL, 88.2 mmol) and N-tert-butoxycarbonylpiperazine (3.62 g, 19.4mmol) were added, followed by stirring at room temperature for 4 hours and then stirring under heating at 60° C. for 6 hours. After the reaction solution was allowed to stand for cooling, it was poured into water, sodium chloride was added thereto, and then the precipitated crystals were recovered by filtration, washed with water, and dried to give the target compound (2.50 g, 7.84 mmol).

Yield: 44%

$^1$H-NMR (DMSO-d$_6$) δ (ppm): 12.20 (1H, br), 7.70 (1H, s), 5.77 (2H, brs), 4.11 (4H, m), 3.43–3.39 (4H, m), 1.43 (9H, s).

FAB-Mass: 320 ((M+1)$^+$)

IR (KBr tablet method) ν (cm$^{-1}$): 1695, 1610,1568, 1487,1421,1261, 1171, 1009.

Reference Example 3

6-(1-Piperazinyl)purine

To an isopropanol solution (50 mL) of piperazine (5.57 g, 64.7 mmol), 6-chloropurine (1.00 g, 6.47 mmol) was added, followed by stirring at room temperature for 1.5 hours and then heating under reflux for 2.5 hours. The reaction solution was concentrated, saturated brine was added thereto, the mixture was extracted with chloroform and THF in that order, the extract was dried over anhydrous sodium sulfate, and then the solvent was evaporated to give the target compound. Thereafter, the water layer after extraction was allowed to stand, and then the precipitated crystals were recovered by filtration to give the target compound (1.07 g in total, 5.25 mmol).

Yield: 81%

Reference Example 4

4-(5-Carbamoyl-1,3-dimethyl-4-1H-pyrazolo[3,4-b] pyridyl)-1-piperazinecarboxylic acid tert-butyl ester The target compound was produced in the same manner as in Reference Example 2, except that 2-amino-6-chloropurine was replaced with commercially available 4-chloro-1,3-dimethyl-1H-pyrazolo[3,4-b]pyridine-5-carboxamide.

Yield: 97%

$^1$H-NMR (CDCl$_3$) δ (ppm): 8.45 (1H, s), 6.56 (1H, br), 6.39 (1H, br), 4.01 (3H, s), 3.64–3.60 (4H, m), 3.33–3.29 (4H, m), 2.67 (3H, s), 1.48 (9H, s).

FAB-Mass: 375 ((M+1)$^+$)

IR (KBr tablet method) ν (cm$^{-1}$): 1672, 1576, 1431, 1367, 1255, 1176.

Reference Example 5

1-Methyl-4-(1-piperazinyl)-1H-pyrazolo[3,4-d] pyrimidine

According to the method described in *J. Org. Chem.*, 21: 1240–1256 (1956), 4-chloro-1-methyl-1H-pyrazolo[3,4-d] pyrimidine was derived from 4-hydroxy-1-methyl-1H-pyrazolo[3,4-d]pyrimidine (1.20 g, 8.03 mmol). To this partially purified product, an isopropanol solution (50 mL) of piperazine (5.55 g, 64.4 mmol) was added, followed by stirring at room temperature for 1 hour and then heating under reflux for 1 hour. The reaction solution was concentrated, saturated brine was added thereto, the mixture was extracted with chloroform, the extract was washed with saturated brine and dried over anhydrous sodium sulfate, and then the solvent was evaporated to give the target compound (1.44 g, 6.61 mmol).

Yield: 83%

Reference Example 6

1-Phenyl-4-(1-piperazinyl)-1H-pyrazolo[3,4-d] pyrimidine

To an isopropanol solution (10 mL) of piperazine (3.74 g, 43.4 mmol), 4-chloro-1-phenylpyrazolo[3,4-d]pyrimidine (100 g, 4.34 mmol) described in *J. Org. Chem.*, 21: 1240–1256 (1956) was added, followed by heating under reflux for 6 hours. The reaction solution was concentrated, saturated brine was added thereto, the mixture was extracted with chloroform, the extract was washed with saturated brine and dried over anhydrous sodium sulfate, and then the solvent was evaporated to give the target compound (1.07 g, 3.82 mmol).

Yield: 88%

$^1$H-NMR (CDCl$_3$+DMSO-d$_6$) δ (ppm): 8.43 (1H, s), 8.15–8.11 (3H, m), 7.55–7.49 (2H, m), 7.34 (1H, m), 4.02–3.99 (4H, m), 3.07–3.03 (4H, m).

FAB-Mass: 281 ((M+1)$^+$)

Reference Example 7

4-(1-Piperazinyl)-5,6-tetramethylenethieno[2,3-d] pyrimidine

The target compound was produced in the same manner as in Reference Example 6, except that 4-chloro-1- phenylpyrazolo[3,4-d]pyrimidine was replaced with 4-chloro-5,6-tetramethylenethieno[2,3-d]pyrimidine described in Heterocycles, 42: 691–699 (1996).

Yield: 74%

$^1$H-NMR (DMSO-d$_6$) δ (ppm): 8.46 (1H, s), 3.35 (4H, m), 3.26–3.24 (4H, m), 2.85 (4H, m), 1.88–1.86 (2H, m), 1.75–1.73 (2H, m).

FAB-Mass: 275 ((M+1)$^+$)

Reference Example 8

4-(4-Pyrido[2,3-d]pyrimidinyl)-1-piperazinecarboxylic acid tert-butyl ester

To a dimethylformamide solution (10 ml) of 4-mercaptopyrido[2,3-d]pyrimidine (742 mg, 4.55 mmol) described in J. Am. Chem. Soc., 77: 2256–2260 (1955), potassium carbonate(755 mg, 5.47 mmol) and methyl iodide (0.34 mL, 5.47 mmol) were added, followed by stirring in argon atmosphere at room temperature overnight. Triethylamine (3.17 ml, 22.7 mmol) and N-tert-butoxycarbonylpiperazine (1.67 g, 8.97 mmol) were added thereto, followed by stirring at room temperature overnight, and then a N-tert-butoxycarbonylpiperazine (0.90 g, 4.83 mmol) was further added thereto, followed by stirring for 3.5 hours under heating at 110° C. The reaction solution was allowed to stand for cooling, water was added thereto, the mixture was extracted with methylene chloride, the extract was washed with saturated brine and dried over anhydrous sodium sulfate, then the solvent was evaporated and the resulting residue was purified by silica gel column chromatography to give the target compound (1.05 g, 3.33 mmol).

Yield: 73%

$^1$H-NMR (CDCl$_3$) δ (ppm): 9.05 (1H, dd, J=4.3 Hz, 2.0 Hz), 8.86 (1H, s), 8.26 (1H, dd, J=8.2 Hz, 2.0 Hz), 7.40 (1H, dd, J=8.2 Hz, 4.3 Hz), 3.86–3.82 (4H, m), 3.68–3.65 (4H, m), 1.50 (9H, s).

FAB-Mass: 316 ((M+1)$^+$)

IR (KBr tablet method) ν (cm$^{-1}$): 1686, 1560, 1497, 1421, 1365, 1333, 1244, 1163, 1005, 808.

Reference Example 9

4-(6-Fluoro-4-pyrido[3,4-d]pyrimidinyl)-1-piperazinecarboxylic acid tert-butyl ester According to the method described in J. Med. Chem., 39:1823–1835 (1996), 4-chloro-6-fluoropyrido[3,4-d]pyrimidine was derived from 6-fluoropyrido[3,4-d]pyrimidine-4(3H)-one (1.48 g, 8.96 mmol). Triethylamine (3.75 mL, 26.9 mmol) and N-tert-butoxycarbonylpiperazine (2.00 g, 10.7 mmol) were added to a methylene chloride solution (25 mL) of this partially purified product, followed by stirring at room temperature overnight. Saturated brine was added to the reaction solution, the mixture ma was extracted with chloroform, the extract was dried over anhydrous sodium sulfate, then the solvent was evaporated and the resulting residue was purified by silica gel column chromatography to give the target compound (1.73 g, 5.20 mmol).

Yield: 58%

$^1$H-NMR (CDCl$_3$) δ (ppm): 9.03 (1H, s), 8.76 (1H, s), 7.28 (1H, d, J=2.0 Hz), 3.87–3.83 (4H, m), 3.69–3.65 (4H, m), 1.51 (9H, s).

FAB-Mass: 334 ((M+1)$^+$)

Reference Example 10

4-(4-Pyrazolo[3,4-d]pyrimidinyl)-1-piperazinecarboxylic acid tert-butyl ester

A dibromomethane suspension (5 mL) of commercially available 4-aminopyrazolo[3,4-d]pyrimidine (420.8 mg, 3.11 mmol) was heated to 80° C., and isoamyl nitrite (0.43 mL, 3.20 mmol) was added thereto, followed by stirring at the same temperature for 3 hours. Isoamyl nitrite (0.43 mL, 3.20 mmol) was further added thereto, followed by heating under reflux for 3.5 hours, and then the insoluble matter was removed by filtration. The filtrate was concentrated, the resulting residue was dissolved in dimethylformamide (5 mL), and then triethylamine (2.00 mL, 14.3 mmol) and N-tert-butoxycarbonylpiperazine (1.00 g, 5.37 mmol) were added thereto, followed by stirring at room temperature overnight. After the reaction solution was concentrated, the resulting residue was purified by silica gel column chromatography to give the target compound (20.4 mg, 0.07 mmol).

Yield: 2%

$^1$H-NMR (CDCl$_3$) δ (ppm): 8.43 (1H, s), 8.03 (1H, s), 4.05–4.02 (4H, m), 3.68–3.64 (4H, m), 1.51 (9H, s).

FAB-Mass: 305 ((M+1)$^+$)

Reference Example 11

4-(6-Hydroxy-4-imidazo[4,5-d]pyrimidinyl)-1-piperazinecarboxylic acid tert-butyl ester (1) To a methylene chloride solution (50 mL) saturated with ammonia, commercially available 4,6-dichloro-5-nitropyrimidine (1.00 g, 5.44 mmol) was added, followed by stirring at room temperature for 1 hour. The reaction solution was concentrated, the resulting residue was dissolved in dimethylformamide (10 mL), and then N-tert-butoxycarbonylpiperazine (1.15 g, 6.17 mmol) and triethylamine (3.59 mL, 25.8 mmol) were added thereto, followed by stirring under heating at 80° C. for 4 hours. After the reaction solution was allowed to stand for cooling, it was poured into water, sodium chloride was added thereto, and the precipitated crystals were recovered by filtration, washed with water, and dried to give 4-(6-amino-5-nitro-4-pyrimidinyl)-1-piperazinecarboxylic acid tert-butyl ester (888 mg, 2.74 mmol).

Yield: 50%

$^1$H-NMR (DMSO-d$_6$) δ (ppm): 8.47–8.42 (2H, br), 7.99 (1H, s), 3.45 (8H, m), 1.42 (9H, s).

FAB-Mass: 325 ((M+1)$^+$)

(2) To an ethanol solution (10 mL) of the compound produced in (1) (888 mg, 2.74 mmol), 10% palladium-carbon (200 mg, 50% aqueous) was added thereto, followed by stirring in a hydrogen stream at room temperature for 2 hours. Chloroform was added to the reaction solution, the catalyst was removed by filtration using a filter aid, and then the filtrate was concentrated under reduced pressure. The resulting residue was dissolved in dimethylformamide (10 mL), and triethylamine (1.91 mL, 13.7 mmol) and 1,1'-carbonyldiimidazole (888 mg, 5.48 mmol) were added thereto, followed by stirring under heating at 80° C. for 4.5 hours. After the reaction solution was allowed to stand for cooling, it was poured into water, sodium chloride was. added thereto, and the precipitated crystals were recovered by filtration, washed with water, and dried to give the target compound (161 mg, 0.50 mmol).

Yield: 18%

$^1$H-NMR (DMSO-d$_6$) δ (ppm): 11.49 (1H, br), 10.83 (1H, br), 8.10 (1H, s), 3.50–3.48 (4H, m), 3.43–3.42 (4H, m), 1.42 (9H, s).

FAB-Mass: 321 ((M+1)$^+$)

Formulation Example 1

Tablets

Tablets comprising the following composition are prepared in a usual method.

| | |
|---|---|
| Compound 5 | 100 mg |
| Lactose | 60 mg |
| Potato starch | 30 mg |
| Polyvinyl alcohol | 2 mg |
| Magnesium stearate | 1 mg |
| Tar dye | trace amount |

Formulation Example 2

Powders

Powders comprising the following composition are prepared in a usual method.

| | |
|---|---|
| Compound 1 | 150 mg |
| Lactose | 280 mg |

Formulation Example 3

Syrups

Syrups comprising the following composition are prepared in a usual method.

| | |
|---|---|
| Compound 41 | 100 mg |
| Purified sucrose | 40 g |
| Ethyl p-hydroxybenzoate | 40 mg |
| Propyl p-hydroxybenzoate | 10 mg |
| Strawberry flavor | 0.1 cc |

The total volume is adjusted to 100 cc by adding water.

Industrial Applicability

According to the present invention, nitrogen-containing heterocyclic compounds or pharmaceutically acceptable salts thereof can be provided, which are useful for the prevention or treatment of cell proliferative diseases such as arteriosclerosis, vascular re-obstruction disease, cancers, glomerulonephritis and the like, by inhibiting abnormal cell proliferation and wandering through the inhibition of phosphorylation of PDGF receptors.

What is claimed is:

1. A nitrogen-containing heterocyclic compound represented by formula (I):

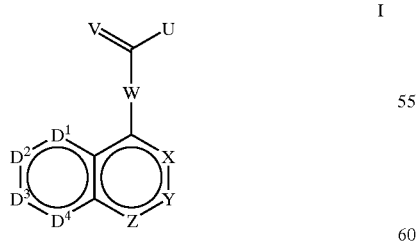

I wherein W represents 1,4-piperazinediyl or 1,4-homopiperazinediyl in which carbon atoms on the ring may be substituted with 1 to 4 alkyl groups which are the same or different;

U represents $NR^1R^2$ (wherein $R^1$ represents a hydrogen atom, a substituted or unsubstituted alkyl group, a substituted or unsubstituted alicyclic alkyl group (said alicyclic alkyl group is selected from the group consisting of monocyclic groups having from 3 to 12 carbon atoms, pinanyl, 1,7,7-trimethylbicyclo[2.2.1]heptyl, adamantyl, hexahydro-4,7-methano-1H-indenyl and 4-hexylbicyclo[2.2.2]octyl), an optionally substituted alicyclic heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group; and $R^2$ represents a hydrogen atom, a substituted alkyl group, a substituted or unsubstituted alicyclic alkyl group (said alicyclic alkyl group is selected from the group consisting of monocyclic groups having from 3 to 12 carbon atoms, pinanyl, 1,7,7-trimethylbicyclo[2.2.1]heptyl, adamantyl, hexahydro-4,7-methano-1H-indenyl and 4-hexylbicyclo[2.2.2]octyl), an optionally substituted alicyclic heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, a substituted or unsubstituted heteroarylalkyl group, $CQR^{1A}$ (wherein Q represents an oxygen atom or a sulfur atom; and $R^{1A}$ has the same meaning as $R^1$), or $SO_2R^3$ (wherein $R^3$ represents a substituted or unsubstituted alkyl group, a substituted or unsubstituted alicyclic alkyl group (said alicyclic alkyl group is selected from the group consisting of monocyclic groups having from 3 to 12 carbon atoms, pinanyl, 1,7,7-trimethylbicyclo[2.2.1]heptyl, adamantyl, hexahydro-4.7-methano-1H-indenyl and 4-hexylbicyclo[2.2.2]octyl), an optionally substituted alicyclic heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group)), $OR^4$ (wherein $R^4$ has the same meaning as $R^3$), or $SR^5$ (wherein $R^5$ has the same meaning as $R^3$);

V represents an oxygen atom, a sulfur atom, $N—R^6$ (wherein $R^6$ has the same meaning as $R^1$ or represents a cyano group, a hydroxyl group, a nitro group, a carbamoyl group, $COOR^{3A}$ (wherein $R^{3A}$ has the same meaning as $R^3$), $CQ^AR^{1B}$ (wherein $Q^A$ has the same meaning as Q, and $R^{1B}$ has the same meaning as $R^1$), or $SO_2R^{3B}$ (wherein $R^{3B}$ has the same meaning as $R^3$)), or $CR^7R^8$ (wherein $R^7$ and $R^8$ are the same or different and each represents a hydrogen atom, a cyano group, a nitro group, $COOR^{3C}$ (wherein $R^{3C}$ has the same meaning as $R^3$), or $SO_2R^{3D}$ (wherein $R^{3D}$ has the same meaning as $R^3$)), with the proviso that, when $R^1$ is hydrogen, $R^6$ and $R^2$ may be exchanged, V may represent $N—R^2$, or $—R^6$, and when U is $OR^4$ or $SR^5$, V represents $N—R^6$ or $CR^7R^8$, at least one of X, Y and Z represents a nitrogen atom, and the others are the same or different, and each represents a nitrogen atom or C—$R^A$ <wherein $R^A$ has the same meaning as $R^1$, or represents a halogen atom, a cyano group, a nitro group, $NR^9R^{10}$ {wherein $R^9$ and $R^{10}$ are the same or different, and each has the same meaning as $R^1$, or represents $SO_2R^{3E}$ (wherein $R^{3E}$ has the same meaning as $R^3$) or $CQ^BR^{11}$ (wherein $Q^B$ has the same meaning as Q; and $R^{11}$ has the same meaning as $R^1$, or represents $OR^{3F}$ (wherein $R^{3F}$ has the same meaning as $R^3$) or $NR^{1C}R^{1D}$ (wherein $R^{1C}$ and $R^{1D}$ are the same or different, and each has the same meaning as $R^1$, or $R^{1C}$ and $R^{1D}$ are combined to represent a substituted or unsubstituted nitrogen-containing heterocyclic group)), or $R^9$ and $R^{10}$ are combined to represent a substituted or unsubstituted nitrogen-containing heterocyclic group}, $CQ^CR^{11A}$ (wherein $Q^C$ has the same meaning as Q; and $R^{11A}$ has the same meaning as $R^{11}$), $OR^{12}$ {wherein $R^{12}$ has the same meaning as $R^1$, or represents $CQ^DR^{13}$ (wherein $Q^D$ has the same meaning as Q; and $R^{13}$ has the same meaning as $R^1$, or represents $OR^{3G}$ (wherein $R^{3G}$ has the same meaning as $R^3$), $SR^{3H}$ (wherein $R^{3H}$ has the same meaning as $R^3$), or $NR^{1E}R^{1F}$ (wherein $R^{1E}$ and $R^{1F}$ are the same or different, and each has the same meaning as $R^1$, or $R^{1E}$ and $R^{1F}$ are combined to represent a substituted or unsubstituted nitrogen-containing heterocyclic group)), or $SO_2R^{3I}$ (wherein $R^{3I}$ has the same meaning as $R^3$)}, $SR^{1G}$ (wherein $R^{1G}$ has the same meaning as $R^1$), $SOR^{3J}$ (wherein $R^{3J}$ has the same meaning as $R^3$) or $SO_2R^{14}$ (wherein $R^{14}$ has the same meaning as $R^3$, or represents $OR^{1H}$ (wherein $R^{1H}$ has the same meaning as $R^1$) or $NR^{1I}R^{1J}$ (wherein $R^{1I}$ and $R^{1J}$ are the same or different, and each has the same meaning as $R^1$, or $R^{1I}$ and $R^{1J}$ are combined to represent a substituted or unsubstituted nitrogen-containing heterocyclic group)) >, and (1) when V represents N—$R^6$ or $CR^7R^8$, and U represents $NR^1R^2$, $OR^4$, or $SR^5$, $D^1$, $D^2$, $D^3$ and $D^4$ each independently represent C—$R^B$ (wherein $R^B$ has the same meaning as $R^A$), a nitrogen atom, an oxygen atom, or a sulfur atom; or optional adjoining two among $D^1$ to $D^4$ may be combined to represent a nitrogen atom, N—$R^{2A}$ (wherein $R^{2A}$ has the same meaning as $R^2$, or represents an alkyl group or $CQ^ENHR^{3K}$ (wherein $Q^E$ has the same meaning as Q; and $R^{3K}$ has the same meaning as $R^3$)), an oxygen atom, or a sulfur atom, and the remains among $D^1$ to $D^4$ may represent C—$R^{B'}$ (wherein $R^{B'}$ has the same meaning as $R^A$), N—$R^{2A}$ (wherein $R^{2A}$ has the same meaning as $R^{2A}$, or a nitrogen atom; and in these two cases, the optional adjoining two selected from $D^1$ to $D^4$ may represent C—$R^{B''}$ (wherein two $R^{B''}$s, together with the two adjoining carbon atoms, represent an optionally substituted alicyclic alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted thiophene, substituted or unsubstituted oxazole, substituted or unsubstituted oxadiazole, substituted or unsubstituted isoxazole, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), and (2) when V represents an oxygen atom or a sulfur atom, and U represents $NR^1R^2$ (2-1)

at least one of $D^1$ to $D^4$ represents a nitrogen atom, an oxygen atom or a sulfur atom; optional adjoining two among $D^1$ to $D^4$ are combined to represent a nitrogen atom, N—$R^{2B}$ (wherein $R^{2B}$ has the same meaning as $R^2$), or an oxygen atom; or $D^2$ and $D^3$ are combined to represent a sulfur atom; and in these three cases, the remains among $D^1$ to $D^4$ represent a nitrogen atom, N—$R^{2B'}$ (wherein $R^{2B'}$ has the same meaning as $R^2$), an oxygen atom, a sulfur atom, or C—$R^C$ (wherein the $R^C$s each independently have the same meaning as $R^A$, or optional two $R^C$s' adjoining adjacent carbon atoms, together with the two adjoining carbon atoms, may represent an optionally substituted alicyclic alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted oxazole, substituted or unsubstituted oxadiazole, substituted or unsubstituted isoxazole, substituted or unsubstituted thiophene, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), (2-2)

$D^1$ and $D^2$ are combined to represent a sulfur atom; $D^3$ represents C—$R^{C'}$ (wherein $R^{C'}$ has the same meaning as $R^A$); and $D^4$ represents a nitrogen atom, or $D^3$ and $D^4$ represent C—$R^{C''}$ (wherein $R^{C''}$s, together with two adjoining carbon atoms, represent an optionally substituted alicyclic alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted oxazole, substituted or unsubstituted oxadiazole, substituted or unsubstituted isoxazole, substituted or unsubstituted thiophene, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), (2-3)

D$^3$ and D$^4$ are combined to represent a sulfur atom; D$^2$ represents C—R$^{C'''}$ (wherein R$^{C'''}$ has the same meaning as R$^A$); and D$^1$ represents a nitrogen atom, or D$^1$ and D$^2$ represent C—R$^{C'''}$ (wherein R$^{C'''}$ has the same meaning as R$^{C'}$), or (2-4)

D$^1$, D$^2$, D$^3$ and D$^4$ represent C—R$^D$ (wherein in R$^D$s, optional two R$^D$s' adjoining adjacent carbon atoms, together with the two adjoining carbon atoms, represent an optionally substituted alicyclic alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted furan, substituted or unsubstituted thiophene, substituted or unsubstituted oxadiazole, substituted or unsubstituted isoxazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, or substituted or unsubstituted tetrazine, and each of the remaining R$^D$s independently represents the same meaning as R$^A$), or a pharmaceutically acceptable salt thereof.

2. The nitrogen-containing heterocyclic compound according to claim 1, wherein W represents 1,4-piperazinediyl, or a pharmaceutically acceptable salt thereof.

3. The nitrogen-containing heterocyclic compound according to claim 2, wherein at least one of X and Z represents a nitrogen atom; and Y represents C—R$^A$ or a pharmaceutically acceptable salt thereof.

4. The nitrogen-containing heterocyclic compound according to claim 3, wherein X and Z each represent a nitrogen atom; and R$^A$ represents a hydrogen atom or NR$^9$R$^{10}$, or a pharmaceutically acceptable salt thereof.

5. The nitrogen-containing heterocyclic compound according to claim 4, wherein U represents NR$^1$R$^2$, or a pharmaceutically acceptable salt thereof.

6. The nitrogen-containing heterocyclic compound according to claim 5, wherein R$^1$ represents a hydrogen atom; and R$^2$ represents a hydrogen atom, a substituted alkyl group, a substituted or unsubstituted alicyclic alkyl group (said alicyclic alkyl group is selected from the group consisting of monocyclic groups having from 3 to 12 carbon atoms, pinanyl, 1,7,7-trimethylbicyclo[2.2.1]heptyl, adamantyl, hexahydro-4,7-methano-1H-indenyl and 4-hexylbicyclo[2.2.2]octyl), an optionally substituted alicyclic heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group, or a pharmaceutically acceptable salt thereof.

7. The nitrogen-containing heterocyclic compound according to claim 6, wherein R$^2$ represents a substituted or unsubstituted aryl group, a substituted or unsubstituted aralkyl group, a substituted or unsubstituted heteroaryl group, or a substituted or unsubstituted heteroarylalkyl group, or a pharmaceutically acceptable salt thereof.

8. The nitrogen-containing heterocyclic compound according to claim 7, wherein V represents N—R$^6$; and 1) D$^1$ and D$^2$ are combined to represent N—R$^{2A}$; and D$^3$ and D$^4$ each independently represent C—R$^{B'}$, 2) D$^1$ and D$^2$ each independently represent C—R$^{B'}$; and D$^3$ and D$^4$ are combined to represent N—R$^{2A}$, 3) D$^1$ and D$^4$ each independently represent C—R$^{B'}$; and D$^2$ and D$^3$ are combined to represent N—R$^{2A}$, 4) D$^1$ represents C—R$^{B'}$; D$^2$ and D$^3$ are combined to represent a nitrogen atom; and D$^4$ represents N—R$^{2A'}$, 5) D$^4$ represents C—R$^{B'}$; D$^2$ and D$^3$ are combined to represent a nitrogen atom; and D$^1$ represents N—R$^{2A'}$, 6) D$^1$ and D$^2$ are combined to represent N—R$^{2A}$; D$^3$ represents C—R$^{B'}$; and D$^4$ represents a nitrogen atom, 7) D$^1$ and D$^2$ are combined to represent a nitrogen atom; D$^3$ represents C—R$^{B'}$; and D$^4$ represents N—R$^{2A}$, 8) D$^1$, D$^2$ and D$^3$ each independently represent C—R$^B$; and D$^4$ represents a nitrogen atom, 9) D$^1$, D$^2$ and D$^4$ each independently represent C—R$^B$; and D$^3$ represents a nitrogen atom, 10) D$^1$, D$^3$ and D$^4$ each independently represent C—R$^B$; and D$^2$ represents a nitrogen atom, 11) D$^1$, D$^3$ and D$^4$ each independently represent C—R$^B$; and D$^1$ represents a nitrogen atom, 12) D$^1$ and D$^3$ represent nitrogen atoms; and D$^2$ and D$^4$ each independently represent C—R$^B$, 13) D$^1$ and D$^3$ each independently represent C—R$^B$; and D$^2$ and D$^4$ represent nitrogen atoms, 14) D$^1$ and D$^2$ each independently represent C—R$^B$; and D$^3$ and D$^4$ represent nitrogen atoms, 15) D$^1$ and D$^4$ each independently represent C—R$^B$; and D$^2$ and D$^3$ represent nitrogen atoms, 16) D$^3$ and D$^4$ each independently represent C—R$^B$; and D$^1$ and D$^2$ represent nitrogen atoms, 17) D$^2$ and D$^3$ each independently represent C—R$^B$; and D$^1$ and D$^4$ represent nitrogen atoms, 18) D$^1$, D$^2$, D$^3$ and D$^4$ each independently represent C—R$^B$, 19) D$^1$ and D$^2$ each independently represent C—R$^{B'}$; and D$^3$ and D$^4$ are combined to represent a sulfur atom, 20) D$^1$ and D$^4$ each independently represent C—R$^{B'}$; and D$^2$ and D$^3$ are combined to represent a sulfur atom, or 21) D$^3$ and D$^4$ each independently represent C—R$^{B'}$; and D$^1$ and D$^2$ are combined to represent a sulfur atom, or a pharmaceutically acceptable salt thereof.

9. The nitrogen-containing heterocyclic compound according to claim 7, wherein V represents an oxygen atom or a sulfur atom; and 1) D$^1$ and D$^2$ are combined to represent N—R$^{2B}$; and D$^3$ and D$^4$ each independently represent C—R$^C$, 2) D$^1$ and D$^2$ each independently represent C—R$^C$; and D$^3$ and D$^4$ are combined to represent N—R$^{2B}$, 3) D$^1$ and D$^4$ each independently represent C—R$^C$; and D$^2$ and D$^3$ are combined to represent N—R$^{2B}$, 4) D$^1$ represents C—R$^C$; D$^2$ and D$^3$ are combined to represent a nitrogen atom; and D$^4$ represents N—R$^{2B'}$, 5) D$^4$ represents C—R$^C$; D$^2$ and D$^3$ are combined to represent a nitrogen atom; and D$^1$ represents N—R$^{2B'}$, 6) D$^1$ and D$^2$ are combined to represent N—R$^{2B}$; D$^3$ represents C—R$^C$; and D$^4$ represents a nitrogen atom, 7) D$^1$ and D$^2$ are combined to represent a nitrogen atom; D$^3$ represents C—R$^C$; and D$^4$ represents N—R$^{2B'}$, 8) $D^1$, $D^2$ and $D^3$ each independently represent C—$R^C$; and $D^4$ represents a nitrogen atom, 9) $D^1$, $D^2$ and $D^4$ each independently represent C—$R^C$; and $D^3$ represents a nitrogen atom, 10) $D^1$, $D^3$ and $D^4$ each independently represent C—$R^C$; and $D^2$ represents a nitrogen atom, 11) $D^2$, $D^3$ and $D^4$ each independently represent C—$R^C$; and $D^1$ represents a nitrogen atom, 12) $D^1$ and $D^3$ represent nitrogen atoms; and $D^2$ and $D^4$ each independently represent C—$R^C$, 13) $D^1$ and $D^3$ each independently represent C—$R^C$; and $D^2$ and $D^4$ are nitrogen atoms, 14) $D^1$ and $D^2$ each independently represent C—$R^C$; and $D^3$ and $D^4$ are nitrogen atoms, 15) $D^1$ and $D^4$ each independently represent C—$R^C$; and $D^2$ and $D^3$ are nitrogen atoms, 16) $D^3$ and $D^4$ each independently represent C—$R^C$; and $D^1$ and $D^2$ are nitrogen atoms, 17) $D^2$ and $D^3$ each independently represent C—$R^C$; and $D^1$ and $D^4$ are nitrogen atoms, 18) $D^1$, $D^2$, $D^3$ and $D^4$ each independently represent C—$R^D$, 19) $D^1$ and $D^2$ each independently represent C—$R^{C'''}$; and $D^2$ and $D^3$ are combined to represent a sulfur atom, 20) $D^1$ and $D^4$ each independently represent C—$R^C$; and $D^2$ and $D^3$ are combined to represent a sulfur atom, or 21) $D^3$ and $D^4$ each independently represent C—$R^C$; and $D^1$ and $D^2$ are combined to represent a sulfur atom, or a pharmaceutically acceptable salt thereof.

10. The nitrogen-containing heterocyclic compound according to claim 8, wherein $R^6$ represents CN; and 1) $D^1$ and $D^2$ are combined to represent a nitrogen atom; $D^3$ represents C—$R^B$; and $D^4$ represents N—$R^{2A'}$, 2) $D^1$, $D^2$ and $D^4$ each independently represent C—$R^B$; and $D^3$ represents a nitrogen atom, or 3) $D^1$, $D^2$, $D^3$ and $D^4$ each independently represent C—$R^B$, or a pharmaceutically acceptable salt thereof.

11. The nitrogen-containing heterocyclic compound according to claim 9,

1) $D^1$ and $D^2$ are combined to represent a nitrogen atom; $D^3$ represents C—$R^C$; and $D^4$ represents N—$R^{2B'}$, 2) $D^1$, $D^2$ and $D^4$ each independently represent C—$R^C$; and $D^1$ represents a nitrogen atom, or 3) $D^1$, $D^2$, $D^3$ and $D^4$ each independently represent C—$R^D$, or a pharmaceutically acceptable salt thereof.

12. The nitrogen-containing heterocyclic compound according to claim 7, wherein V represents an oxygen atom or a sulfur atom; $D^1$, $D^2$, $D^3$ and $D^4$ represent C—$R^D$; and optional two $R^D$s' adjoining adjacent carbon atoms, together with the two adjoining carbon atoms, represent substituted or unsubstituted pyrrole, substituted or unsubstituted pyrazole, substituted or unsubstituted pyridine, substituted or unsubstituted pyrimidine, substituted or unsubstituted pyridazine, or substituted or unsubstituted pyrazine, or a pharmaceutically acceptable salt thereof.

13. A nitrogen-containing heterocyclic compound represented by formula (I):

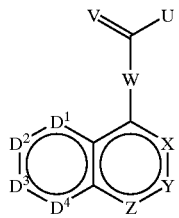

wherein W represents 1,4-piperazinediyl or 1,4-homopiperazinediyl in which carbon atoms on the ring may be substituted with 1 to 4 alkyl groups which are the same or different;

U represents $NR^1R^2$ (wherein $R^1$ represents a hydrogen atom a substituted or unsubstituted alkyl group, a substituted or unsubstituted group being selected from monocyclic groups having from 3 to 12 carbon atoms, pinanyl, 1,7,7-trimethylbicyclo[2.2.1]heptyl, adamantly, hexahydro-4,7-methano-1H-indenyl and 4-hexylbicyclo[2.2.2]octyl, an optionally substituted heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group; and $R^2$ represents a hydrogen atom, a substituted alkyl group, a substituted or unsubstituted group being selected from monocyclic groups having from 3 to 12 carbon atoms, pinanyl, 1,7,7-trimethylbicyclo[2.2.1]heptyl, adamantly, hexahydro-4,7-methano-1H-indenyl and 4-hexylbicyclo[2.2.2] octyl, an optionally substituted heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, a substituted or unsubstituted heteroarylalkyl group, $CQR^{1A}$ (wherein Q represents an oxygen atom or a sulfur atom; and $R^{1A}$ has the same meaning as $R^1$), or $SO_2R^3$ (wherein $R^3$ represents a substituted or unsubstituted alkyl group, a substituted or unsubstituted group (said group being selected from monocyclic groups having from 3 to 12 carbon atoms, pinanyl, 1,7,7-trimethylbicyclo[2.2.1]heptyl, adamantly, hexahydro-4,7-methano-1H-indenyl and 4-hexybicyclo[2.2.2] octyl), an optionally substituted heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group)), $OR^4$ (wherein $R^4$ has the same meaning as $R^3$), or $SR^5$ (wherein $R^5$ has the same meaning as $R^3$);

V represents an oxygen atom, a sulfur atom, N—$R^6$ (wherein $R^6$ has the same meaning as $R^1$ or represents a cyano group, a hydroxyl group, a nitro group, a carbamoyl group, COOR$^{3A}$ (wherein R$^{3A}$ has the same meaning as R$^3$), CQ$^A$R$^{1B}$ (wherein Q$^A$ has the same meaning as Q, and R$^{1B}$ has the same meaning as R$^1$), or SO$_2$R$^{3B}$ (wherein R$^{3B}$ has the same meaning as R$^3$)), or CR$^7$R$^8$ (wherein R$^7$ and R$^8$ are the same or different and each represents a hydrogen atom, a cyano group, a nitro group, COOR$^{3C}$ (wherein R$^{3C}$ has the same meaning as R$^3$), or SO$_2$R$^{3D}$ (wherein R$^{3D}$ has the same meaning as R$^3$)), with the proviso that, when R$^1$ is hydrogen, R$^6$ and R$^2$ may be exchanged, V may represent N—R$^2$, or N—R$^6$, and when U is OR$^4$ or SR$^5$, V represents N—R$^6$ or CR$^7$R$^8$, at least one of X, Y and Z represents a nitrogen atom, and the others are the same or different, and each represents a nitrogen atom or C—R$^A$ <wherein R$^A$ has the same meaning as R$^1$, or represents a halogen atom, a cyano group, a nitro group, NR$^9$R$^{10}$ {wherein R$^9$ and R$^{10}$ are the same or different, and each has the same meaning as R$^1$, or represents SO$_2$R$^{3E}$ (wherein R$^{3E}$ has the same meaning as R$^3$) or CQ$^B$BR$^{11}$ (wherein Q$^B$ has the same meaning as Q; and R$^{11}$ has the same meaning as R$^1$, or represents OR$^{3F}$ (wherein R$^{3F}$ has the same meaning as R$^3$) or NR$^{1C}$R$^{1D}$ (wherein R$^{1C}$ and R$^{1D}$ are the same or different, and each has the same meaning as R$^1$, or R$^{1C}$ and R$^{1D}$ are combined to represent a substituted or unsubstituted nitrogen-containing heterocyclic group)), or R$^9$ and R$^{10}$ are combined to represent a substituted or unsubstituted nitrogen-containing heterocyclic group}, CQ$^C$R$^{11A}$ (wherein Q$^C$ has the same meaning as Q; and R$^{11A}$ has the same meaning as R$^{11}$), OR$^{12}$ {wherein R$^{12}$ has the same meaning as R$^1$, or represents CQ$^D$R$^{13}$ (wherein Q$^D$ has the same meaning as Q; and R$^{13}$ has the same meaning as R$^1$, or represents OR$^{3G}$ (wherein R$^{3G}$ has the same meaning as R$^3$), SR$^{3H}$ (wherein R$^{3H}$ has the same meaning as R$^3$), or NR$^{1E}$R$^{1F}$ (wherein R$^{1E}$ and R$^{1F}$ are the same or different, and each has the same meaning as R$^1$, or R$^{1E}$ and R$^{1F}$ are combined to represent a substituted or unsubstituted nitrogen-containing heterocyclic group)), or SO$^2$R$^{3I}$ (wherein R$^{3I}$ has the same meaning as R$^3$)}, SR$^{1G}$ (wherein R$^{1G}$ has the same meaning as R$^1$), SOR$^{3J}$ (wherein R$^{3J}$ has the same meaning as R$^3$) or SO$_2$R$^{14}$ (wherein R$^{14}$ has the same meaning as R$^3$, or represents OR$^{1H}$ (wherein R$^{1H}$ has the same meaning as R$^1$) or NR$^{1I}$R$^{1J}$ (wherein R$^{1I}$ and R$^{1J}$ are the same or different, and each has the same meaning as R$^1$, or R$^{1I}$ and R$^{1J}$ are combined to represent a substituted or unsubstituted nitrogen-containing heterocyclic group))>, and (1) when V represents N—R$^6$ or CR$^7$R$^8$, and U represents NR$^1$R$^2$, OR$^4$, or SR$^5$ D$^1$, D$^2$, D$^3$ and D$^4$ each independently represent C—R$^B$ (wherein R$^B$ has the same meaning as R$^A$), a nitrogen atom, an oxygen atom, or a sulfur atom: or optional adjoining two among D$^1$ to D$^4$ maybe combined to represent a nitrogen atom, N—R$^{2A}$ (wherein R$^{2A}$ has the same meaning as R$^2$ described above, or represents an alkyl group or CQ$^E$NHR$^{3K}$ (wherein Q$^E$ has the same meaning as Q and R$^{3K}$ has the same meaning as R$^3$), an oxygen atom, or a sulfur atom, and the remains among D$^1$ to D$^4$ may represent C—R$^{B'}$ (wherein R$^{B'}$ has the same meaning as R$^A$), N—R$^{2A'}$ (wherein R$^{2A'}$ has the same meaning as R$^{2A}$), or a nitrogen atom; and in these two cases, the optional adjoining two selected from D$^1$ to D$^4$ may represent C—R$^{B''}$ (wherein two R$^{B''}$s, together with the two adjoining carbon atoms, represent an optionally substituted alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted thiophene, substituted or unsubstituted oxazole, substituted or unsubstituted oxadiazole, substituted or unsubstituted isoxazole, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), and (2) when V represents an oxygen atom or a sulfur atom, and U represents NR$^1$R$^2$, (2-1)

at least one of D$^1$ to D$^4$ represents a nitrogen atom, an oxygen atom or a sulfur atom; optional adjoining two among D$^1$ to D$^4$ are combined to represent a nitrogen atom, N—R$^{2B}$ (wherein R$^{2B}$ has the same meaning as R$^2$), or an oxygen atom; or D$^2$ and D$^3$ are combined to represent a sulfur atom; and in these three cases, the remains among D$^1$ to D$^4$ represent a nitrogen atom, N—R$^{2B'}$ (wherein R$^{2B'}$ has the same meaning as R$^2$), an oxygen atom, a sulfur atom, or C—R$^C$ (wherein the R$^C$s each independently have the same meaning as R$^A$, or optional two R$^C$s' adjoining adjacent carbon atoms, together with the two adjoining carbon atoms, may represent an optionally substituted alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted oxazole, substituted or unsubstituted oxadiazole, substituted or unsubstituted isoxazole, substituted or unsubstituted thiophene, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene, (2-2)

D$^1$ and D$^2$ are combined to represent a sulfur atom; D$^3$ represents C—R$^C$ (wherein R$^{C'}$ has the same meaning as R$^A$); and D$^4$ represents a nitrogen atom, or D$^3$ and D$^4$ represent C—R$^{C''}$ (wherein R$^{C''}$s, together with two adjoining carbon atoms, represent an optionally substituted alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted imidazole, substituted or unsubstituted imidazol-2-one, substituted or unsubstituted imidazole-2-thione, substituted or unsubstituted triazole, substituted or unsubstituted furan, substituted or unsubstituted 1,3-dioxole, substituted or unsubstituted 1,4-dioxene, substituted or unsubstituted oxazole, substituted or unsubstituted oxadiazole, substituted or unsubstituted isoxazole, substituted or unsubstituted thiophene, substituted or unsubstituted thiazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, substituted or unsubstituted tetrazine, or substituted or unsubstituted benzene), (2-3)

$D^3$ and $D^4$ are combined to represent a sulfur atom; $D^2$ represents C—$R^{C'''}$ (wherein $R^{C'''}$ has the same meaning as $R^A$); and $D^1$ represents a nitrogen atom, or $D^1$ and $D^2$ represent C—$R^{C''''}$ (wherein $R^{C''''}$ has the same meaning as $R^{C''}$), or (2-4)

$D^1$, $D^2$, $D^3$ and $D^4$ represent C—$R^D$ (wherein in $R^D$s, optional two $R^D$s' adjoining adjacent carbon atoms, together with the two adjoining carbon atoms, represent an optionally substituted alkene selected from the group consisting of cyclobutene, cyclopentene, cyclohexene, cycloheptene, cyclooctene and cyclododecene, substituted or unsubstituted pyrrole, substituted or unsubstituted pyrazole, substituted or unsubstituted furan, substituted or unsubstituted thiophene, substituted or unsubstituted oxadiazole, substituted or unsubstituted isoxazole, substituted or unsubstituted isothiazole, substituted or unsubstituted thiadiazole, substituted or unsubstituted pyridine, substituted or unsubstituted pyrazine, substituted or unsubstituted pyrimidine, substituted or unsubstituted pyridazine, substituted or unsubstituted triazine, or substituted or unsubstituted tetrazine, and each of the remaining $R^D$s independently represents the same meaning as $R^A$), or a pharmaceutically acceptable salt thereof.

14. The nitrogen-containing heterocyclic compound according to claim 13, wherein W represents 1,4 piperazinediyl, or a pharmaceutically acceptable salt thereof.

15. The nitrogen-containing heterocyclic compound according to claim 14, wherein at least one of X and Z represents a nitrogen atom; and Y represents C—$R^A$, or a pharmaceutically acceptable salt thereof.

16. The nitrogen-containing heterocyclic compound according to claim 15, wherein X and Z each represent a nitrogen atom; and $R^A$ represents a hydrogen atom or $NR^9R^{10}$, or a pharmaceutically acceptable salt thereof.

17. The nitrogen-containing heterocyclic compound according to claim 16, wherein U represents $NR^1R^2$, or a pharmaceutically acceptable salt thereof.

18. The nitrogen-containing heterocyclic compound according to claim 17, wherein $R^1$ represents a hydrogen atom; and $R^2$ represents a hydrogen atom, a substituted alkyl group, a substituted or unsubstituted group (said group being selected from monocyclic groups having from 3 to 12 carbon atoms, pinanyl, 1,7,7-trimethylbicyclo[2.2.1]heptyl, adamantyl, hexahydro-4,7-methano-1H-indenyl and 4-hexylbicyclo[2.2.2]octyl), an optionally substituted heterocyclic group selected from the group consisting of tetrahydrofuryl, tetrahydropyranyl, pyrrolidinyl, piperidyl, piperazinyl, morpholinyl and thiomorpholinyl, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group, or a pharmaceutically acceptable salt thereof.

19. The nitrogen-containing heterocyclic compound according to claim 18, wherein $R^2$ represents a substituted or unsubstituted aryl group, a substituted or unsubstituted aralkyl group, a substituted or unsubstituted heteroaryl group, or a substituted or unsubstituted heteroarylalkyl group, or a pharmaceutically acceptable salt thereof.

20. The nitrogen-containing heterocyclic compound according to claim 19, wherein V represents N—$R^6$; and 1) $D^1$ and $D^2$ are combined to represent N—$R^{2A}$; and $D^3$ and $D^4$ each independently represent C—$R^{B'}$, 2) $D^1$ and $D^2$ each independently represent C—$R^{B'}$; and $D^3$ and $D^4$ are combined to represent N—$R^{2A}$, 3) $D^1$ and $D^4$ each independently represent C—$R^{B'}$; and $D^2$ and $D^3$ are combined to represent N—$R^{2A}$, 4) $D^1$ represents C—$R^{B'}$; $D^2$ and $D^3$ are combined to represent a nitrogen atom; and $D^4$ represents N—$R^{2A'}$, 5) $D^4$ represents C—$R^{B'}$; $D^2$ and $D^3$ are combined to represent a nitrogen atom; and $D^1$ represents N—$R^{2A'}$, 6) $D^1$ and $D^2$ are combined to represent N—$R^{2A}$; $D^3$ represents C—$R^{B'}$; and $D^4$ represents a nitrogen atom, 7) $D^1$ and $D^2$ are combined to represent a nitrogen atom; $D^3$ represents C—$R^{B'}$; and $D^4$ represents N—$R^{2A'}$, 8) $D^1$, $D^2$ and $D^3$ each independently represent C—$R^B$; and $D^4$ represents a nitrogen atom, 9) $D^1$, $D^2$ and $D^4$ each independently represent C—$R^B$; and $D^3$ represents a nitrogen atom, 10) $D^1$, $D^3$ and $D^4$ each independently represent C—$R^B$; and $D^2$ represents a nitrogen atom, 11) $D^2$, $D^3$ and $D^4$ each independently represent C—$R^B$; and $D^1$ represents a nitrogen atom, 12) $D^1$ and $D^3$ represent nitrogen atoms; and $D^2$ and $D^4$ each independently represent C—$R^B$, 13) $D^1$ and $D^3$ each independently represent C—$R^8$; and $D^2$ and $D^2$ represent nitrogen atoms, 14) $D^1$ and $D^2$ each independently represent C—$R^B$; and $D^2$ and $D^4$ represent nitrogen atoms, 15) $D^1$ and $D^2$ each independently represent C—$R^B$; and $D^2$ and $D^3$ represent nitrogen atoms, 16) $D^3$ and $D^4$ each independently represent C—$R^B$; and $D^1$ and $D^2$ represent nitrogen atoms, 17) $D^2$ and $D^3$ each independently represent C—$R^B$; and $D^1$ and $D^4$ represent nitrogen atoms, 18) $D^1$, $D^2$, $D^3$ and $D^4$ each independently represent C—$R^B$, 19) $D^1$ and $D^2$ each independently represent C—$R^{B'}$; and $D^3$ and $D^4$ are combined to represent a sulfur atom, 20) $D^1$ and $D^4$ each independently represent C—$R^{B'}$; and $D^2$ and $D^3$ are combined to represent a sulfur atom, or 21) $D^3$ and $D^4$ each independently represent C—$R^{B'}$; and $D^1$ and $D^2$ are combined to represent a sulfur atom, or a pharmaceutically acceptable salt thereof.

21. The nitrogen-containing heterocyclic compound according to claim 19, wherein V represents an oxygen atom or a sulfur atom; and 1) $D^1$ and $D^2$ are combined to represent N—$R^{2B}$; and $D^3$ and $D^4$ each independently represent C—$R^C$, 2) $D^1$ and $D^2$ each independently represent C—$R^C$, and $D^3$ and $D^4$ are combined to represent N—$R^{2B}$, 3) $D^1$ and $D^4$ each independently represent C—$R^C$ and $D^2$ and $D^3$ are combined to represent N—$R^{2B}$, 4) $D^1$ represents C—$R^C$; $D^2$ and $D^3$ are combined to represent a nitrogen atom; and $D^4$ represents N—$R^{2B'}$, 5) $D^4$ represents C—$R^C$; $D^2$ and $D^3$ are combined to represent a nitrogen atom; and $D^1$ represents N—$R^{2B'}$, 6) $D^1$ and $D^2$ are combined to represent N—$R^{2B}$; $D^3$ represents C—$R^C$; and $D^4$ represents a nitrogen atom, 7) $D^1$ and $D^2$ are combined to represent a nitrogen atom; $D^3$ represents C—$R^C$; and $D^4$ represents N—$R^{2B'}$, 8) $D^1$, $D^2$ and $D^3$ each independently represent C—$R^C$; and $D^4$ represents a nitrogen atom, 9) $D^1$, $D^2$ and $D^4$ each independently represent C—$R^C$; and $D^3$ represents a nitrogen atom, 10) $D^1$, $D^3$ and $D^4$ each independently represent C—$R^C$; and $D^2$ represents a nitrogen atom, 11) $D^2$, $D^3$ and $D^4$ each independently represent C—$R^C$; and $D^1$ represents a nitrogen atom, 12) $D^1$ and $D^3$ represent nitrogen atoms; and $D^2$ and $D^4$ each independently represent C—$R^C$, 13) $D^1$ and $D^3$ each independently represent C—$R^C$; and $D^2$ and $D^4$ are nitrogen atoms, 14) $D^1$ and $D^2$ each independently represent C—$R^C$; and $D^3$ and $D^4$ are nitrogen atoms, 15) $D^1$ and $D^4$ each independently represent C—$R^C$; and $D^2$ and $D^3$ are nitrogen atoms, 16) $D^3$ and $D^4$ each independently represent C—$R^C$ and $D^1$ and $D^2$ are nitrogen atoms, 17) $D^2$ and $D^3$ each independently represent C—$R^C$; and $D^1$ and $D^4$ are nitrogen atoms, 18) $D^1$, $D^2$, $D^3$ and $D^4$ each independently represent C—$R^D$, 19) $D^1$ and $D^4$ each independently represent C—$R^{C''}$; and $D^3$ and $D^4$ are combined to represent a sulfur atom, 20) $D^1$ and $D^4$ each independently represent C—$R^C$; and $D^2$ and $D^3$ are combined to represent a sulfur atom, or 21) $D^3$ and $D^4$ each independently represent C—$R^{C''}$; and $D^1$ and $D^2$ are combined to represent a sulfur atom, or a pharmaceutically acceptable salt thereof.

22. The nitrogen-containing heterocyclic compound according to claim 20, wherein $R^6$ represents CN; and 1) $D^1$ and $D^2$ are combined to represent a nitrogen atom; $D^3$ represents C—$R^{B'}$; and $D^4$ represents N—$R^{2A'}$, 2) $D^1$, $D^2$ and $D^4$ each independently represent C—$R^B$; and $D^3$ represents a nitrogen atom, or 3) $D^1$, $D^2$, $D^3$ and $D^4$ each independently represent C—$R^B$, or a pharmaceutically acceptable salt thereof.

23. The nitrogen-containing heterocyclic compound according to claim 21,

1) $D^1$ and $D^2$ are combined to represent a nitrogen atom; $D^3$ represents C—$R^C$; and $D^4$ represents N—$R^{2B'}$, 2) $D^1$, $D^2$ and $D^4$ each independently represent C—$R^C$; and $D^3$ represents a nitrogen atom, or 3) $D^1$, $D^2$, $D^3$ and $D^4$ each independently represent C—$R^D$, or a pharmaceutically acceptable salt thereof.

24. The nitrogen-containing heterocyclic compound according to claim 19, wherein V represents an oxygen atom or a sulfur atom; $D^1$, $D^2$, $D^3$ and $D^4$ represent C—$R^D$; and optional two $R^D$s' adjoining adjacent carbon atoms, together with the two adjoining carbon atoms, represent substituted or unsubstituted pyrrole, substituted or unsubstituted pyrazole, substituted or unsubstituted pyridine, substituted or unsubstituted pyrimidine, substituted or unsubstituted pyridazine, or substituted or unsubstituted pyrazine, or a pharmaceutically acceptable salt thereof.

* * * * *

UNITED STATES PATENT AND TRADEMARK OFFICE
CERTIFICATE OF CORRECTION

PATENT NO. : 6,423,716 B1
DATED : July 23, 2002
INVENTOR(S) : Kenji Matsuno et al.

It is certified that error appears in the above-identified patent and that said Letters Patent is hereby corrected as shown below:

Title page,
Item [57], ABSTRACT,
Line 18, "etc.;" should read -- etc.); --.

Column 5,
Line 44, "$R^D S$" should read -- $R^D s$ --.

Column 7,
Line 42, "comb" should read -- combined to represent a --.

Column 8,
Line 60, "alicyclic heteroring" should read -- alicyclic alkylsulfonyl group, alicyclic heteroring --.

Column 9,
Line 4, "the," should read -- the --.

Column 10,
Line 27, "(Wherein" should read -- (wherein) --; and
Line 51, "represent" should read -- represents --.

Column 11,
Line 11, "$R_C$" should read -- $R^C$ --.

Column 13,
Line 14, "Also" should read -- Also, --;
Line 59, "atoms" should read -- atoms, --; and
Line 60, ", which" should read -- which --.

Column 16,
Line 37, "1823- 1835" should read -- 1823-1835 --.

Column 19,
Line 65, "dimethylaminopropyl)carbodiimide" should read -- dimethylaminopropyl)-carbodiimide --.

UNITED STATES PATENT AND TRADEMARK OFFICE
CERTIFICATE OF CORRECTION

PATENT NO. : 6,423,716 B1
DATED : July 23, 2002
INVENTOR(S) : Kenji Matsuno et al.

It is certified that error appears in the above-identified patent and that said Letters Patent is hereby corrected as shown below:

Column 20,
Line 39, "ordinary" should read -- ordinarily --.

Column 34,
Line 23, "kinase" (first occurrence) should read -- kinases --; and
Line 61, "for2.5 hours." should read -- for 2.5 hours. --.

Column 37,
Line 56, "(d1 )" should read -- (d1) --.

Column 40,
Line 12, "s)," (first occurrence) should read -- m), --.

Column 47,
Line 22, "1-" (second occurrence) should be deleted; and
Line 23, "piperazinecarboxamidine" should be deleted.

Column 51,
Line 30, "67 (ppm):" should read -- δ (ppm): --.

Column 53,
Line 7, "11. 50 (1H, br), 10. 85" should read -- 11.50 (1H, br), 10.85 --.

Column 55,
Line 50, "ma" should be deleted.

Column 56,
Line 59, "was." should read -- was --.

Column 59,
Line 49, "$R^{2A}$," should read -- $R^2$), --.

Column 62,
Line 24, "$D^1$," should read -- $D^2$, --.

UNITED STATES PATENT AND TRADEMARK OFFICE
CERTIFICATE OF CORRECTION

PATENT NO. : 6,423,716 B1
DATED : July 23, 2002
INVENTOR(S) : Kenji Matsuno et al.

It is certified that error appears in the above-identified patent and that said Letters Patent is hereby corrected as shown below:

Column 63,
Line 46, "claim 9," should read -- claim 9, wherein --.

Column 64,
Line 17, "atom a" should read -- atom, a --; and
Line 53, "4-hexybicyclo[2.2.2]" should read -- 4-hexylbicyclo[2.2.2] --.

Column 65,
Line 55, "maybe" should read -- may be --.

Column 66,
Line 59, "$C-R^C$" should read -- $C-R^{C'}$ --.

Column 67,
Line 63, "1,7,7-trimethylbicyclof[2.2.1]heptyl," should read -- 1,7,7-trimethylbicyclo[2.2.1]heptyl, --.

Column 68,
Line 41, "$C-R^8$;" should read -- $C-R^B$; --; and
Line 42, "$D^2$ and $D^2$" should read -- $D^2$ and $D^4$ --.

Column 70,
Line 11, "represents $C-R^{B'}$;" should read -- $D^3$ represents $C-R^{B'}$; --; and
Line 19, "claim 21," should read -- claim 21, wherein --.

Signed and Sealed this

Twenty-second Day of April, 2003

JAMES E. ROGAN
*Director of the United States Patent and Trademark Office*